(12) United States Patent
DuMontelle et al.

(10) Patent No.: US 11,793,628 B2
(45) Date of Patent: Oct. 24, 2023

(54) TRANSCATHETER BIO-PROSTHESIS MEMBER AND SUPPORT STRUCTURE

(71) Applicant: VALCARE, INC., Irvine, CA (US)

(72) Inventors: Jeffrey DuMontelle, Irvine, CA (US); Samuel Shaolian, Newport Bearch, CA (US); Nadav Yellin, Aven Yehuda (IL); Aviad Galler, Tel Aviv (IL); Shuki Porath, St. Haifa (IL)

(73) Assignee: VALCARE, INC., Herzelyia Pituach (IL)

( * ) Notice: Subject to any disclaimer, the term of this patent is extended or adjusted under 35 U.S.C. 154(b) by 0 days.

(21) Appl. No.: 16/930,225

(22) Filed: Jul. 15, 2020

(65) Prior Publication Data

US 2021/0015609 A1    Jan. 21, 2021

Related U.S. Application Data

(60) Provisional application No. 62/874,296, filed on Jul. 15, 2019.

(51) Int. Cl.
*A61F 2/24* (2006.01)

(52) U.S. Cl.
CPC .......... *A61F 2/2409* (2013.01); *A61F 2/2418* (2013.01); *A61F 2/2427* (2013.01);
(Continued)

(58) Field of Classification Search
CPC .... A61F 2/2409; A61F 2/2466; A61F 2/2448; A61F 2/2427; A61F 2/2418;
(Continued)

(56) References Cited

U.S. PATENT DOCUMENTS

| 4,602,911 A | 7/1986 | Ahmadi et al. |
| 5,236,440 A | 8/1993 | Hlavacek |

(Continued)

FOREIGN PATENT DOCUMENTS

| EP | 2600799 A2 | 6/2013 |
| KR | 1020040095482 | 11/2004 |

(Continued)

OTHER PUBLICATIONS

European Search Report in EP 17155803.4 dated Aug. 9, 2017.
(Continued)

*Primary Examiner* — Bruce E Snow
(74) *Attorney, Agent, or Firm* — Dorsey & Whitney LLP

(57) ABSTRACT

An implantable valve replacement system for a cardiovascular valve may include an adjustable stabilizing ring. The stabilizing ring may be composed of a body member that is transitionable from an elongate insertion geometry to an annular operable geometry. The stabilizing ring may further include a plurality of anchors deployable in the annular operable geometry to engage the annulus of the cardiovascular valve. The ring may be used in conjunction with an implantable valve frame. The valve frame may be located within the ring and the ring, in turn, may be stabilized through the anchors engaging the valve annulus. The valve replacement system may be applied by engaging the ring in its annular operable geometry with the valve annulus through the anchors. The valve frame may be inserted through the opening of the ring, thereby forming a stabilizing mechanical contact between the frame and the annulus.

11 Claims, 61 Drawing Sheets

(52) U.S. Cl.
CPC .......... *A61F 2/2448* (2013.01); *A61F 2/2466* (2013.01); *A61F 2210/0014* (2013.01); *A61F 2220/0016* (2013.01); *A61F 2250/001* (2013.01)

(58) Field of Classification Search
CPC ...... A61F 2210/0014; A61F 2220/0016; A61F 2250/001; A61F 2/2436
See application file for complete search history.

(56) References Cited

U.S. PATENT DOCUMENTS

| | | |
|---|---|---|
| 5,306,296 A | 4/1994 | Wright et al. |
| 5,695,518 A | 12/1997 | Laerum |
| 5,716,370 A | 2/1998 | Williamson, IV et al. |
| 5,855,614 A | 1/1999 | Stevens et al. |
| 6,113,611 A | 9/2000 | Allen et al. |
| 6,231,602 B1 | 5/2001 | Carpentier et al. |
| 6,619,291 B2 | 9/2003 | Hlavka et al. |
| 6,629,534 B1 | 10/2003 | St. Goar et al. |
| 6,669,687 B1 | 12/2003 | Saadat |
| 6,689,048 B2 | 2/2004 | Vanden Hoek et al. |
| 6,726,704 B1 | 4/2004 | Loshakove et al. |
| 6,776,784 B2 | 8/2004 | Ginn |
| 6,790,229 B1 | 9/2004 | Berreklouw |
| 6,797,002 B2 | 9/2004 | Spence et al. |
| 6,805,711 B2 | 10/2004 | Quijano et al. |
| 6,893,459 B1 | 5/2005 | Macoviak |
| 7,101,395 B2 | 9/2006 | Tremulis et al. |
| 7,114,953 B1 | 10/2006 | Wagner |
| 7,175,660 B2 | 2/2007 | Cartledge et al. |
| 7,238,191 B2 | 7/2007 | Bachmann |
| 7,285,087 B2 | 10/2007 | Moaddeb et al. |
| 7,297,150 B2 | 11/2007 | Cartledge et al. |
| 7,569,072 B2 | 8/2009 | Berg et al. |
| 7,594,887 B2 | 9/2009 | Moaddeb et al. |
| 7,635,329 B2 | 12/2009 | Goldfarb et al. |
| 7,655,040 B2 | 2/2010 | Douk et al. |
| 7,717,954 B2 | 5/2010 | Solem et al. |
| 7,722,668 B2 | 5/2010 | Moaddeb et al. |
| 7,758,637 B2 | 7/2010 | Starksen et al. |
| 7,837,729 B2 | 11/2010 | Gordon et al. |
| 7,988,725 B2 | 8/2011 | Gross et al. |
| 8,163,014 B2 | 4/2012 | Lane et al. |
| 8,182,529 B2 | 5/2012 | Gordon et al. |
| 8,236,049 B2 | 8/2012 | Rowe et al. |
| 8,287,591 B2 | 10/2012 | Keidar et al. |
| 8,518,107 B2 | 8/2013 | Tsukashima et al. |
| 8,579,968 B1 | 11/2013 | Shannon et al. |
| 9,180,008 B2 | 11/2015 | Yellin et al. |
| 2002/0151961 A1 | 10/2002 | Lashinski et al. |
| 2002/0151970 A1 | 10/2002 | Garrison et al. |
| 2002/0188170 A1 | 12/2002 | Santamore et al. |
| 2002/0198526 A1 | 12/2002 | Shaolian et al. |
| 2003/0050693 A1 | 3/2003 | Quijano et al. |
| 2003/0078465 A1 | 4/2003 | Pai et al. |
| 2003/0078671 A1 | 4/2003 | Lesniak et al. |
| 2003/0191528 A1 | 10/2003 | Quijano et al. |
| 2003/0198605 A1 | 10/2003 | Montgomery |
| 2003/0199974 A1 | 10/2003 | Lee et al. |
| 2004/0044364 A1 | 3/2004 | DeVries et al. |
| 2004/0068276 A1 | 4/2004 | Golden et al. |
| 2004/0122514 A1 | 6/2004 | Fogarty et al. |
| 2004/0138744 A1 | 7/2004 | Lashinski et al. |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0249391 A1 | 12/2004 | Cummins |
| 2004/0260393 A1 | 12/2004 | Rahdert et al. |
| 2004/0260394 A1 | 12/2004 | Douk et al. |
| 2005/0020696 A1 | 1/2005 | Montgomery et al. |
| 2005/0033325 A1 | 2/2005 | May et al. |
| 2005/0065550 A1 | 3/2005 | Starksen et al. |
| 2005/0090846 A1 | 4/2005 | Pedersen et al. |
| 2005/0096740 A1 | 5/2005 | Langberg et al. |
| 2005/0113910 A1 | 5/2005 | Paniagua et al. |
| 2005/0137692 A1 | 6/2005 | Haug et al. |
| 2005/0137695 A1 | 6/2005 | Salahieh et al. |
| 2005/0203549 A1 | 9/2005 | Realyvasquez |
| 2005/0222678 A1 | 10/2005 | Lashinski et al. |
| 2005/0240200 A1 | 10/2005 | Bergheim |
| 2005/0267572 A1 | 12/2005 | Schoon et al. |
| 2005/0283190 A1 | 12/2005 | Huitema et al. |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0020327 A1 | 1/2006 | Lashinski et al. |
| 2006/0122633 A1 | 6/2006 | To et al. |
| 2006/0129025 A1 | 6/2006 | Levine et al. |
| 2006/0155165 A1 | 7/2006 | Vanden Hoek et al. |
| 2006/0161169 A1 | 7/2006 | Nieminen et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0195183 A1 | 8/2006 | Navia et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk |
| 2007/0038296 A1 | 2/2007 | Navia et al. |
| 2007/0051377 A1 | 3/2007 | Douk et al. |
| 2007/0067027 A1 | 3/2007 | Moaddeb et al. |
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1 | 9/2007 | Webler et al. |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0306586 A1 | 12/2008 | Cartledge et al. |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0191327 A1* | 7/2010 | Lane .................... A61F 2/2409 623/2.36 |
| 2010/0211166 A1 | 8/2010 | Miller et al. |
| 2010/0249920 A1 | 9/2010 | Bolling et al. |
| 2010/0266989 A1 | 10/2010 | Piergallini et al. |
| 2010/0280605 A1 | 11/2010 | Hammer et al. |
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0034999 A1 | 2/2011 | Carpentier et al. |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |

(56) References Cited

U.S. PATENT DOCUMENTS

| | | |
|---|---|---|
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2012/0022557 A1 | 1/2012 | Cabiri et al. |
| 2012/0022644 A1 | 1/2012 | Reich et al. |
| 2012/0059458 A1 | 3/2012 | Buchbinder et al. |
| 2012/0083880 A1 | 4/2012 | Rankin et al. |
| 2012/0095455 A1 | 4/2012 | Rodmond et al. |
| 2012/0123531 A1* | 5/2012 | Tsukashima .......... A61F 2/2448 623/2.37 |
| 2012/0136436 A1 | 5/2012 | Cabiri et al. |
| 2012/0165930 A1 | 6/2012 | Gifford, III et al. |
| 2012/0245604 A1 | 9/2012 | Tegzes |
| 2012/0310330 A1 | 12/2012 | Buchbinder et al. |
| 2013/0087598 A1 | 4/2013 | Surti |
| 2013/0116780 A1 | 5/2013 | Miller et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0289718 A1 | 10/2013 | Tsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0046433 A1 | 2/2014 | Kovalsky |
| 2014/0058505 A1 | 2/2014 | Bielefeld |
| 2014/0214157 A1* | 7/2014 | Bortlein .................. A61F 2/243 623/2.11 |
| 2015/0173897 A1 | 6/2015 | Raanani et al. |
| 2015/0351903 A1 | 12/2015 | Morriss et al. |
| 2016/0038286 A1 | 2/2016 | Yellin et al. |
| 2016/0089235 A1 | 3/2016 | Yellin |
| 2016/0106420 A1 | 4/2016 | Foerster et al. |
| 2016/0120642 A1 | 5/2016 | Shaolian et al. |
| 2016/0120645 A1 | 5/2016 | Alon |
| 2016/0220371 A1* | 8/2016 | Keane .................. A61F 2/2442 |
| 2017/0042670 A1 | 2/2017 | Shaolian et al. |
| 2017/0231763 A1 | 8/2017 | Yellin |
| 2017/0325948 A1* | 11/2017 | Wallace ................ A61F 2/2409 |
| 2018/0042723 A1 | 2/2018 | Yellin et al. |
| 2019/0091022 A1 | 3/2019 | Yellin et al. |

FOREIGN PATENT DOCUMENTS

| | | |
|---|---|---|
| RU | 125062 | 2/2013 |
| WO | 9009153 A1 | 8/1990 |
| WO | 03017874 A1 | 3/2003 |
| WO | 03047467 A1 | 6/2003 |
| WO | 2005046488 A2 | 5/2005 |
| WO | 2009052427 A1 | 4/2009 |
| WO | 2009120764 A2 | 10/2009 |
| WO | 2010004546 A1 | 1/2010 |
| WO | 2010085659 A1 | 7/2010 |
| WO | 2011011443 A2 | 1/2011 |
| WO | 2011097355 A2 | 8/2011 |
| WO | 2012004679 A2 | 1/2012 |
| WO | 2012019052 A2 | 2/2012 |
| WO | 2012063228 A1 | 5/2012 |
| WO | 2012095159 A2 | 7/2012 |
| WO | 2012106354 A1 | 8/2012 |
| WO | 2012167095 A2 | 12/2012 |
| WO | 2013095816 A1 | 6/2013 |
| WO | 2013128436 A1 | 9/2013 |
| WO | 2013130641 A1 | 9/2013 |
| WO | 2013175468 A2 | 11/2013 |
| WO | 2014145399 A1 | 9/2014 |
| WO | 2014189509 A1 | 11/2014 |
| WO | 2014190329 A1 | 11/2014 |
| WO | 2014210600 A2 | 12/2014 |

OTHER PUBLICATIONS

International Search Report and Written Opinion for PCT/US2011/046659 dated Jun. 4, 2012.
International Search Report and Written Opinion for PCT/US2012/040481 dated Dec. 6, 2012.
International Search Report and Written Opinion for PCT/US2013/042275 dated Feb. 20, 2014.
International Search Report and Written Opinion for PCT/US2013/073552 dated Mar. 6, 2014.
International Search Report and Written Opinion for PCT/US2014/030163 dated Aug. 27, 2014.
International Search Report and Written Opinion for PCT/US2014/039454 dated Oct. 22, 2014.
Supplementary Partial European Search Report for EP 13755441 dated Nov. 3, 2015.
International Search Report and Written Opinion for PCT/US2017/046933 dated Dec. 21, 2017.
International Search Report and Written Opinion for PCT2019/064289 dated Feb. 5, 2020.
International Search Report for PCT/US2013/028065 dated Jun. 27, 2013.
International Search Report for PCT/US2013/058102 dated Apr. 21, 2014.
International Search Report for PCT/US2014/044920 dated Dec. 24, 2014.
Lendlein et al., Biodegradable, Elastic Shape-Memory Polymers for Potential Biomedical Applications, Science, vol. 296 (May 31, 2002), pp. 1673-1676.
Supplemental European Search Report and Written Opinion for EP 12793292.9 dated Dec. 1, 2014.
Supplemental European Search Report and Written Opinion for EP 14762806.9 dated Jul. 29, 2016.
20841346.8, Extended European Search Report, dated Jul. 21, 2023, 9 pages.

* cited by examiner

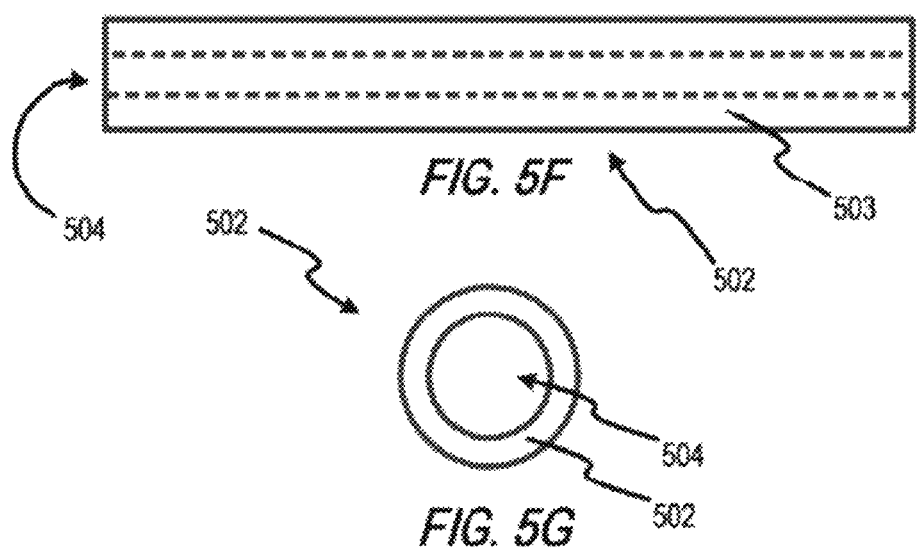
FIG. 5F
FIG. 5G
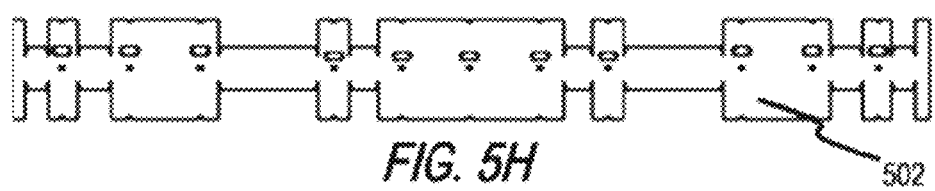
FIG. 5H
FIG. 5I
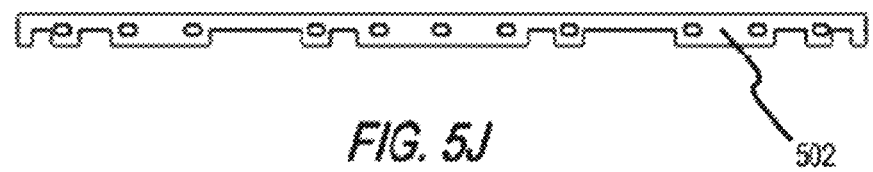
FIG. 5J

TRANSCATHETER BIO-PROSTHESIS MEMBER AND SUPPORT STRUCTURE

PRIORITY

This application claims benefit of and priority to U.S. Provisional Patent Application No. 62/874,296, entitled "HEART AND PERIPHERAL VASCULAR VALVE REPLACEMENT IN CONJUNCTION WITH A SUPPORT RING," filed Jul. 15, 2019, the disclosure of which is incorporated herein by reference in its entirety.

BACKGROUND

There are four valves in the heart that serve to direct blood flow through the two sides of the heart. On the left (systemic) side of the heart are the mitral valve, located between the left atrium and the left ventricle, and the aortic valve, located between the left ventricle and the aorta. These two valves may direct oxygenated blood from the lungs through the left side of the heart and into the aorta for distribution to the body. On the right (pulmonary) side of the heart are the tricuspid valve, located between the right atrium and the right ventricle, and the pulmonary valve, located between the right ventricle and the pulmonary artery. These two valves may direct de-oxygenated blood from the body through the right side of the heart and into the pulmonary artery for distribution to the lungs, where the blood becomes re-oxygenated. The cardiac valves are composed of moveable features, generally described as leaflets or cusps. The mitral valve has two leaflets, and the tricuspid valve has three leaflets. The aortic and pulmonary heart valves have leaflets that are shaped somewhat like half-moons and are typically described as cusps. Each of the aortic valve and the pulmonary valve has three cusps.

Other valves, such as venous valves, may be present in the vascular system to aid in directing the flow of blood through the body. Such peripheral vascular values typically have a single leaflet structure and act as gates to prevent blood from flowing backward. For example, as a leg muscle contracts, the venous vessels may be compressed, and the blood may be pushed through a valve. As the muscle relaxes, the blood may be prevented from flowing backwards as the valve closes. The one-way venous valves may ensure that the blood flows in one direction back towards the heart.

All heart and vascular valves are passive structures that simply open and close in response to differential pressures on either side of the valve. They do not, in general, expend energy and do not perform any active contractile function. The cardiovascular valves may exhibit abnormal anatomy and function as a result of congenital or acquired valve disease. Congenital valve abnormalities may be well-tolerated for many years only to develop a life-threatening problem in an elderly patient. Alternatively, such abnormalities may be so severe that emergency surgery may be required in-utero or within the first few hours of life. Acquired valve disease may result from such causes as rheumatic fever, degenerative disorders of the valve tissue, bacterial or fungal infections, and trauma.

Since the cardiovascular valves are passive structures, valve failure modes can be classified into two categories: stenosis, in which a valve does not open properly; and insufficiency (also called regurgitation), in which a valve does not close properly. Stenosis and insufficiency may occur at the same time in the same valve or in different valves. Both of these abnormalities may increase the workload placed on the heart as well as other organs of the body, such as the liver and kidneys. In particular, the severity of this increased stress on the heart, and the heart's ability to adapt to it, may determine whether an abnormal valve can be repaired or if valve removal and/or replacement is warranted.

SUMMARY

In an embodiment, an implantable valve system may include an adjustable stabilizing ring having a body member that is transitionable from an elongate insertion geometry to an annular operable geometry, and a plurality of anchors deployable in the annular operable geometry to engage the annulus of the cardiovascular valve. The elongate insertion geometry of the body member may be configured to allow percutaneous passage of the stabilizing ring, via a catheter, to a position adjacent to an annulus of a cardiovascular valve. The annular operable geometry of the body member may have a closed state to conform to the annulus of the cardiovascular valve. The implantable valve system may further include an implantable valve frame in mechanical communication with the adjustable stabilizing ring.

In an embodiment, a platform to stabilize an implantable valve frame may include an adjustable stabilizing ring having a body member that is transitionable from an elongate insertion geometry to an annular operable geometry, and a plurality of anchors deployable in the annular operable geometry to engage the annulus of the cardiovascular valve. The elongate insertion geometry of the body member may be configured to allow percutaneous passage of the stabilizing ring, via a catheter, to a position adjacent to an annulus of a cardiovascular valve. The annular operable geometry of the body member may have a closed state to conform to the annulus of the cardiovascular valve. The adjustable stabilizing ring in the closed state of the annular operable geometry may be configured to receive and stabilize the implantable valve frame at a position proximal to the annulus of the cardiovascular valve.

In an embodiment, a method of stabilizing a replacement of a cardiovascular valve may include inserting a distal end of a catheter comprising a delivery system into a cardiovascular valve, guiding, via the delivery system, an adjustable stabilizing ring in an elongate geometry from a proximal end of the catheter to the distal end of the catheter such that the adjustable stabilizing ring transitions to an annular operable geometry upon exiting the distal end of the catheter, deploying a number of anchors from the adjustable stabilizing ring to engage an annulus of the cardiovascular valve, guiding an implantable valve frame including the replacement of the cardiovascular valve through the cardiovascular valve and through a center of the adjustable stabilizing ring, and engaging at least a portion of the implantable valve frame with the adjustable stabilizing ring, thereby stabilizing a position of the implantable valve frame with respect to the cardiovascular valve.

In an embodiment, a method of replacing a cardiovascular valve may include inserting a distal end of a catheter comprising at least one delivery system into a cardiovascular valve, guiding, via the at least one delivery system, an implantable valve frame having the replacement of the cardiovascular valve through the cardiovascular valve, expanding the implantable valve frame, guiding, via the at least one delivery system, an adjustable stabilizing ring in an elongate geometry through the implantable valve frame and the replacement of the cardiovascular valve such that the adjustable stabilizing ring transitions to an annular operable geometry around an exterior of the implantable valve frame upon exiting the distal end of the catheter, engaging at least a portion of the implantable valve frame with the adjustable stabilizing ring, and deploying a number of anchors from the adjustable stabilizing ring to engage an annulus of the cardiovascular valve.

BRIEF DESCRIPTION OF THE DRAWINGS

FIGS. 5F and 5G depict a front view and a side view, respectively, of a tube-like polymeric element according to an embodiment.

FIGS. 5H, 5I, and 5J depict a top view, a first side view, and a second side view, respectively, of a polymeric element according to an embodiment.

DETAILED DESCRIPTION

Figure 1A:
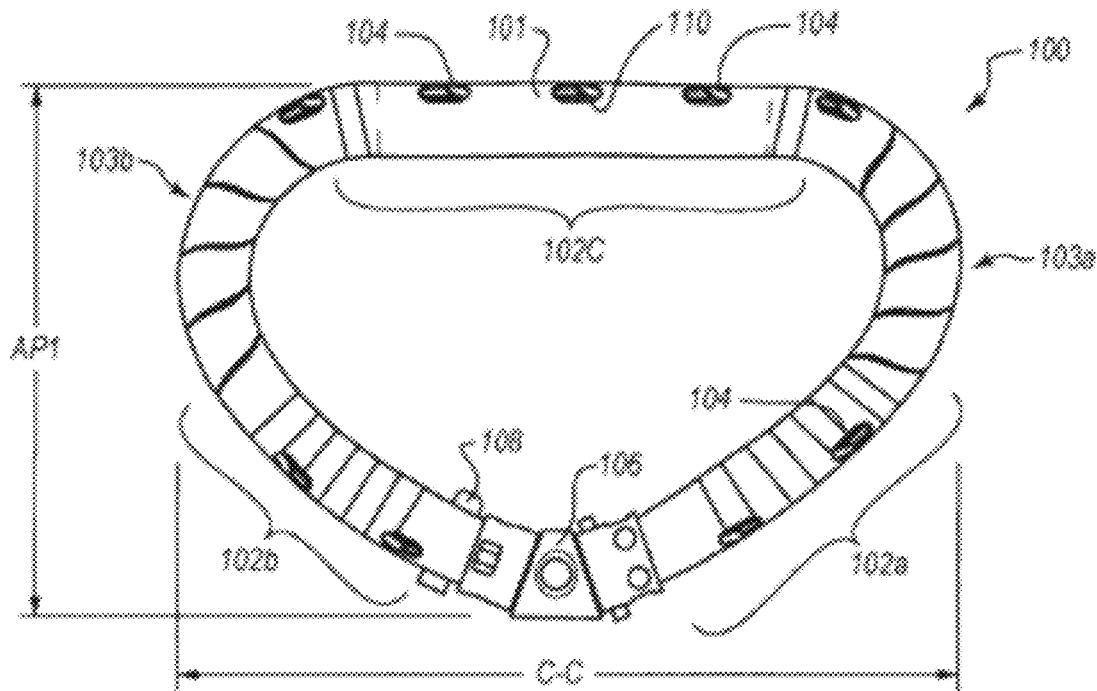
FIG. 1A depicts a perspective view of an illustrative adjustable annuloplasty ring in an annular (D-shaped) operable geometry and a contracted state according to an embodiment.

The valve structures in the heart and vascular system are not composed of rigid tissues but have some natural compliance. The natural compliance of a valve may aid in its natural functional performance. However, if the valve is diseased, the compliance may change significantly, and the function of the valve may be compromised. If the natural tissue structure surrounding the valve is weak, supplemental support of the surrounding tissue may be highly desirable. If the valve structure is not badly compromised, the supplemental support alone may be sufficient to restore the valve's normal function. However, supplemental support alone may not be sufficient to restore a valve's normal function, and the diseased valve may require replacement with a prosthesis.

Minimally invasive or percutaneous valve replacement surgery or valve function replacement is well known in the art, and a number of surgical options are available. However, currently available valve replacement procedures may be difficult to employ for valve implantation in some areas of the heart (e.g. mitral valve, tricuspid valve) or in peripheral (e.g. venous) vasculature where the tissue is naturally highly compliant or is highly compliant due to disease. While the rigid frames used to support the flexible leaflets in replacement valves may be able to hold the replacement prosthetic valve in position acutely, it is difficult for them to remain in place over a long period of time due to the dynamic and compliant nature of the surrounding tissue. Therefore, there is a need for an improvement to allow the prosthetic valve to be implanted within these more highly compliant structures. Through the use of a separate minimally or percutaneously delivered support ring, which may be delivered and secured to the surrounding tissue or annulus thereby reinforcing it, a replacement prosthetic valve may be implanted within the support ring and remain in position to provide the long-term benefit for which it is designed.

A rigid or semi-rigid support ring may be delivered to the valve area via a small bore delivery system or catheter using percutaneous methods. Such a support ring may be external to the replacement valve and could provide the support needed for the replacement prosthetic valve. The use of such a support ring may allow the replacement valve to remain permanently or semi-permanently in place.

A support ring that can be used in conjunction with a prosthetic valve may be fabricated from a biocompatible, durable, non-thrombogenic, sterilizable material and may further exhibit advantageous hemodynamic performance. As cardiovascular procedures become minimally invasive, a support ring or structure that can be delivered using percutaneous procedures and secured to allow for secondary implantation of a prosthetic valve is needed.

The following terms shall have, for the purposes of this application, the respective meanings set forth below.

A "heart valve" refers to any valve of a heart. In some embodiments, the heart may be a human heart. In other embodiments, the valve may be a non-human heart. The heart valves include atrioventricular valves (mitral valve and tricuspid valve) and semilunar valves (aortic valve and pulmonary valve). As used herein, the term "valve" is used to denote a heart valve, except where explicitly stated otherwise. Various portions of the heart, including the valves, may contain one or more fibrous rings there around. Such a fibrous ring is commonly known (and used herein) as an "annulus."

A "patient" refers to any human or non-human individual. The patient is generally any patient that has been diagnosed or will be diagnosed with a valve-related disorder, such as, for example, a heart valve-related disorder. In some embodiments, the patient may be an individual that would benefit from the apparatuses, systems, and methods described herein.

As used herein, "percutaneous" refers to a procedure that uses incisions through the skin of the abdomen for access to a surgical site, such as, for example, a patient's heart. Thus, as used herein, percutaneous surgery and laparoscopic surgery are mutually exclusive. In the preferred embodiment, the methods described herein are performed percutaneously, although laparoscopic methods are contemplated. As used herein, a percutaneous procedure may be a minimally invasive procedure or a highly invasive procedure. A percutaneous procedure may also include a trans-septal approach, a trans-apical approach, or a trans atrial approach.

The systems and methods described herein may generally be used to facilitate repair of a heart valve through percutaneous trans-catheter delivery and fixation of an annuloplasty ring to the heart valve. The embodiments of stabilizers and delivery systems can be configured in elongated insertion geometries that can be inserted into a catheter tube and deployed to an operable geometry providing a 3D geometry that corresponds to and attaches to an annuloplasty ring connected to a catheter delivery system.

Figure 1B:
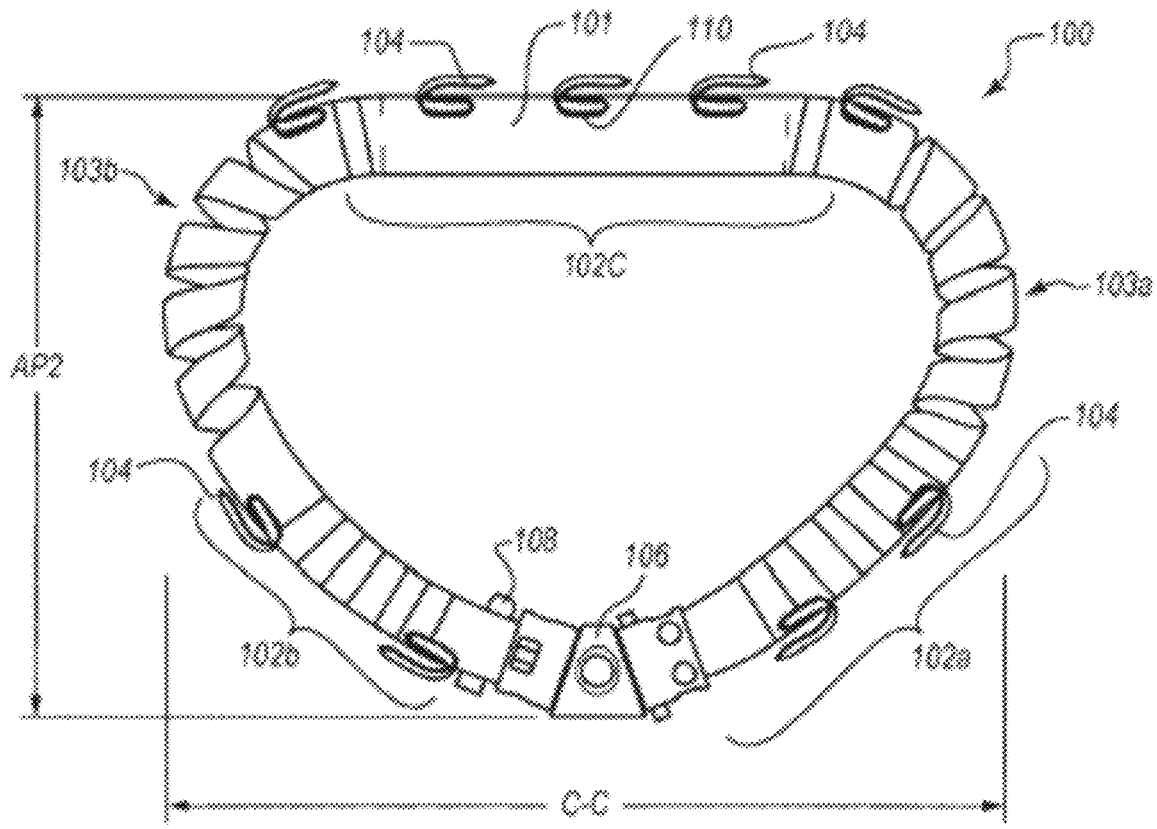
FIG. 1B depicts a perspective view of an illustrative adjustable annuloplasty ring in an expanded state according to an embodiment.

FIG. 1A depicts a schematic diagram of a perspective view of an illustrative adjustable annuloplasty ring, generally designated 100, according to an embodiment. As shown in FIG. 1A, the annuloplasty ring 100 may be in an annular (D-shaped) operable geometry in a contracted state. FIG. 1B depicts a schematic diagram of a perspective view of the adjustable annuloplasty ring 100 of FIG. 1A when in an expanded state. The annuloplasty ring 100 may be configured to enable percutaneous, transcatheter annuloplasty to repair a heart valve. The annuloplasty ring 100 may be fastened, percutaneously, to the annulus of a target heart valve while in the expanded state and reduced to the contracted state to decrease an A-P distance of the target valve and thereby improve leaflet coaptation of the target valve and reduce regurgitation through the target valve.

Referring collectively to FIGS. 1A and 1B, the annuloplasty ring 100 may include a body member 101 having a plurality of regions 102a, 102b, 102c (collectively 102), a plurality of biasing elements 103a, 103b (collectively 103), a plurality of anchors 104, a ring closure lock 106, and a pivot 108. In FIGS. 1A and 1B, as well as in other embodiments disclosed herein, the body member 101, including the plurality of regions 102, may be arranged in a "D-shape" in the operable geometry. The D-shaped annuloplasty ring 100 may have a particular geometric ratio that is in conformance (or approximate conformance) with the anatomical geometry of the human mitral valve annulus. For example, in certain embodiments, the ratio of the A-P distance to the commissure-commissure (C-C) distance of the annuloplasty ring 100 when implanted (for example, in the contracted state) may be about 0.55 to about 0.80, including about 0.55, about 0.60, about 0.65, about 0.70, about 0.75, about 0.80, or any value or range between any two of these values (including endpoints). In a particular embodiment, the implanted ratio of the A-P distance to the C-C distance may be about 0.73.

Although the illustrated embodiment of an annuloplasty ring 100 of FIGS. 1A and 1B is a D-shaped operable geometry, those having ordinary skill in the art will recognize that other annular-shaped operable geometries may also be used without departing from the present disclosure. For example, circular or oval operable geometries may be used.

In some embodiments, the body member 101 may include a hollow hypotube (or outer hollow member). The hypotube may be cut from, for example, a tube to form the plurality of regions 102. The cuts may define a shape and/or characteristics of the body member 101. For example, laser cuts may define the plurality of regions 102 (and define how the plurality of regions interact), anchor windows 110, and/or the biasing elements 103.

In various embodiments, the body member 101 may include a shape memory (such as, for example, nitinol) hypotube into which a plurality of cuts and/or segments may be laser cut to define a size, a shape, and/or characteristics of the plurality of regions 102. The shape memory hypotube may be heat set to a "memorized" annular shape (such as, for example, the D-shaped operable geometry). The shape memory hypotube may be superelastic such that applying sufficient stress may place the body member 101, including the plurality of regions 102, into an elongate insertion geometry and releasing the stress allows the body member 101, including the plurality of regions 102, to resume the D-shaped operable geometry. In some embodiments, laser cuts may define a flexibility of the body member 101. For example, the laser cuts may allow the body member 101 to be flexible when the annuloplasty ring 100 is in an elongate insertion geometry (as described herein) and/or rigid when the annuloplasty ring is in the operable geometry.

In addition to the operable geometry shown in FIGS. 1A and 1B, the body member 101 may be transitionable from an elongate insertion geometry (see, for example, FIG. 9C) to the annular operable geometry shown in FIGS. 1A and 1B. The elongate insertion geometry may allow the annuloplasty ring 100 to be inserted into and passed through a catheter for percutaneous passage into the heart of a patient, as described in greater detail herein. A transition from an elongate insertion geometry to an annular operable geometry is illustrated in FIGS. 9C-9F and discussed herein with reference to the same.

Once in an annular operable geometry as shown in FIGS. 1A and 1B, the annuloplasty ring 100 may have a contracted state as shown in FIG. 1A and an expanded state as shown in FIG. 1B. The biasing elements 103 may be configured to expand to increase the A-P distance of the annuloplasty ring 100 to an expanded state. The A-P distance AP1 of the contracted state of FIG. 1A is enlarged by a distance d such that the A-P distance AP2 of the expanded state FIG. 1B is larger (AP2=AP1+d). Expansion of the biasing elements 103 may allow the body member 101 to be expanded to an expanded state. In situ in the heart, expansion of the body member 101 to the expanded state may enlarge the annuloplasty ring 100 to a size conforming, or approximately conforming, to an annulus of a target heart valve to be repaired. Expansion of the body member 101 may be accomplished by an expansion tool, such as a balloon, a cage, or another tool such as is shown in FIGS. 10, 11, 12A-12E, 13A-13D, and 14A-14B, and described herein with reference to the same. In the illustrated embodiment of FIGS. 1A and 1B, a biasing element 103a disposed between a first posterior region 102a and an anterior region 102c and a biasing element 103b disposed between a second posterior region 102b and the anterior region 102c may enable a desired expansion from the contracted state shown in FIG. 1A to the expanded state shown in FIG. 1B.

The expanded state of FIG. 1B may be such that the annuloplasty ring 100 is disposed in abutment with, or in intimate contact with, the annulus of the target valve. Disposing the annuloplasty ring 100 in intimate contact with the annulus may enhance an anchoring process in which the plurality of anchors 104 are deployed to fasten the annuloplasty ring 100 to the annulus. Once the annuloplasty ring 100 is fastened to the annulus, it may be contracted from the expanded state of FIG. 1B back to the contracted state of FIG. 1A to reduce a diameter of the annulus of the target valve.

Contraction of the annuloplasty ring 100 from the expanded state to the contracted state may decrease the A-P distance of the annuloplasty ring and, with the plurality of anchors 104 securing the annuloplasty ring to the annulus, may also decrease an A-P distance of the target valve to improve leaflet coaptation and reduce regurgitation through the target valve. In the illustrated embodiment of FIGS. 1A and 1B, contraction of the annuloplasty ring 100 from the expanded state to the contracted state may be accomplished by the biasing elements 103. The biasing elements 103 may bias the annuloplasty ring 100 toward the contracted state such that expansion of the annuloplasty ring to the expanded state stores potential energy in the biasing elements 103. Releasing the biasing elements 103 (such as, for example, releasing or otherwise removing an expansion tool and/or expansion force) may release the stored potential energy, thereby forcing movement of the first posterior region 102a and the second posterior region 102b of the body member 101 toward the anterior region 102c of the body member to decrease the A-P distance of the annuloplasty ring 100 to the contracted state. In other words, the biasing elements 103, upon release, may actively transition the annuloplasty ring 100 from the expanded state to the contracted state.

A typical range for change of the A-P distance d (between the expanded state and the contracted state) may be about 3 mm to about 8 mm, including about 3 mm, about 3.5 mm, about 4 mm, about 4.5 mm, about 5 mm, about 5.5 mm, about 6 mm, about 6.5 mm, about 7 mm, about 7.5 mm, about 8 mm, or any value or range between any two of these values (including endpoints). In some embodiments, the range of d may depend on the overall size of the annuloplasty ring 100. For example, for a final geometry in which the A-P distance of the annuloplasty ring 100 is 26 mm, a change distance d of about 3 mm may be desired. As another example, for a final geometry in which the A-P distance of the annuloplasty ring 100 is 36 mm, a change distance d of about 5 mm may be desired.

The biasing elements 103 of the illustrated annuloplasty ring 100 of FIGS. 1A and 1B may be a spiral cut or helical portion of the body member 101 that is laser cut into the body member. The spiral cut or helical portion, because it is cut into the body member 101, is a biasing element 103 that is integral to the body member. The spiral cut portion of the body member 101, as shown in FIG. 1B, may form or otherwise define a spiral shape configured to expand to allow the anterior region 102c to move away from the first posterior region 102a and from the second posterior region 102b, thereby increasing the A-P distance of the annuloplasty ring 100. Also, the spiral cut or helical portion of the body member 101 may be biased toward a relaxed position, or the contracted state as shown in FIG. 1A, such that expansion of the spiral cut or helical portion stores potential energy and release of an expansion force results in a release of potential energy and contraction toward the contracted state.

In some embodiments, other integral biasing elements 103 may be used. For example, a diamond cut pattern cut into the body member 101 may allow desired expansion and biasing toward the contracted state. In another embodiment, a corrugated pattern (such as, for example, folds) may be formed in the body member 101. The corrugated pattern may allow desired expansion to increase the A-P distance of the annuloplasty ring 100 and may be biased toward the contracted state.

Figure 2A:
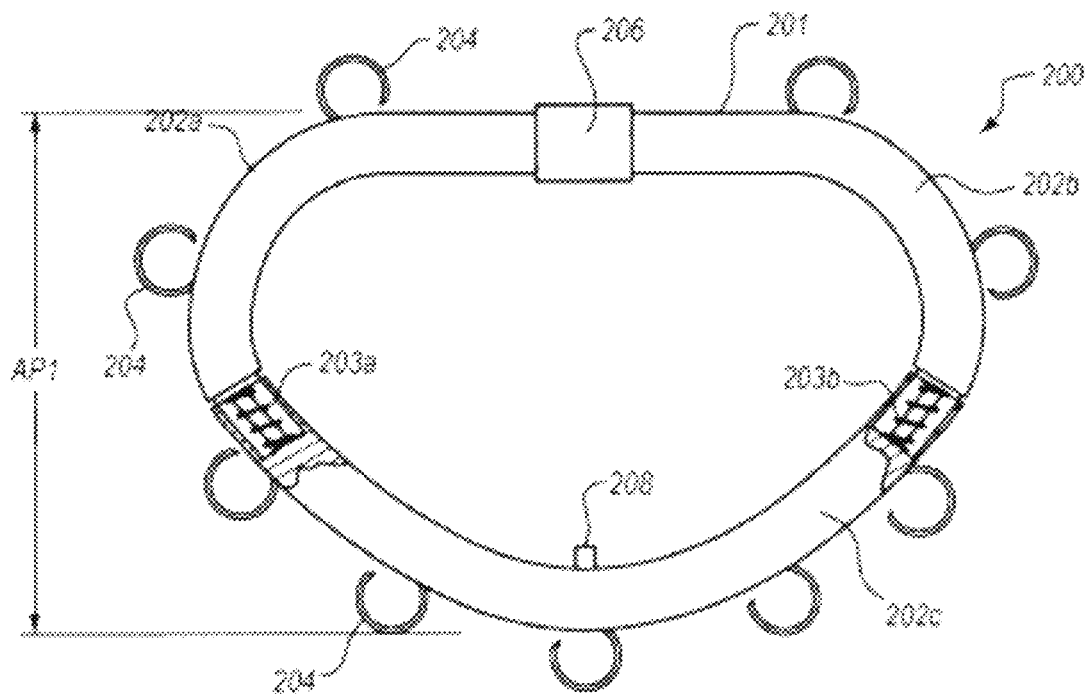
FIG. 2A depicts a schematic diagram of a perspective view of a second illustrative adjustable annuloplasty ring in an annular (D-shaped) operable geometry and a contracted state according to an embodiment.
Figure 2B:
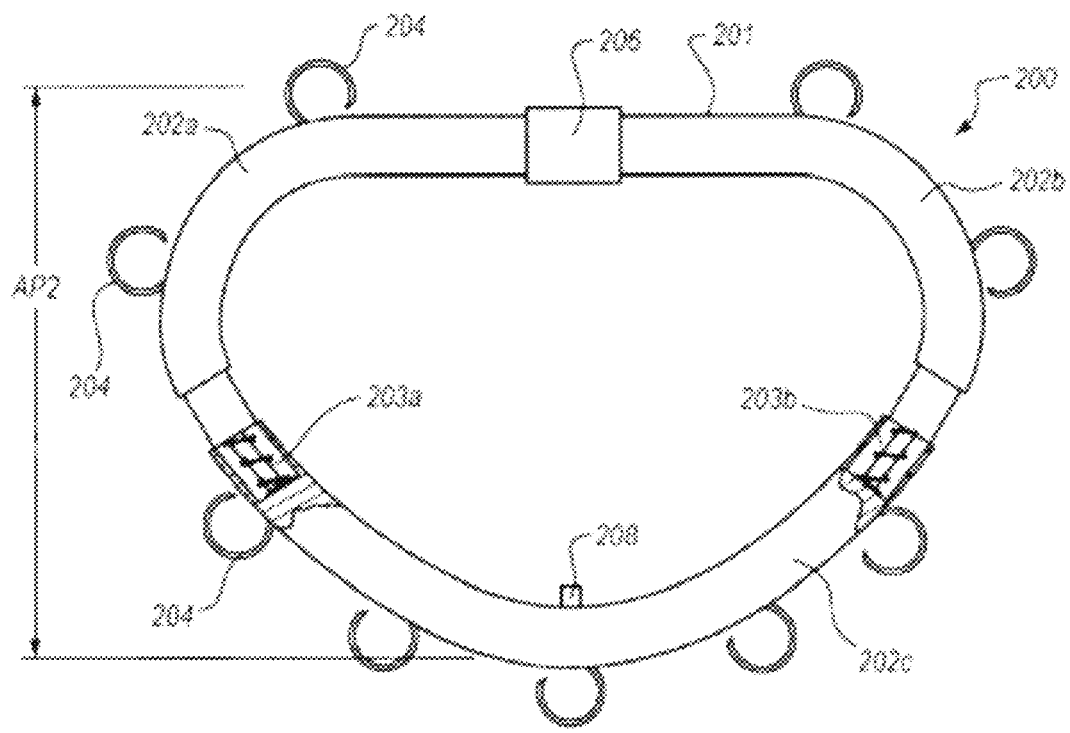
FIG. 2B depicts a schematic diagram of a perspective view of an illustrative adjustable annuloplasty ring in an expanded state according to an embodiment.

In addition to integral biasing elements 103 (formed integrally in the body member 101 of the annuloplasty ring 100), other biasing elements 103 may be used that are not integral to the body member. For example, FIGS. 2A and 2B illustrate an embodiment in which the biasing element 203 is a spring and not integral to the body member 201, as described herein. In still other embodiments, the biasing element 203 may include a non-integral biasing component (such as, for example, a spring) to complement or enhance operation of an integrally formed biasing element.

Referring back to FIGS. 1A and 1B, the plurality of anchors 104, as noted above, may be configured to secure the annuloplasty ring 100 to the annulus of the heart valve. In some embodiments, the anchors 104 may be barbs. As used herein, the terms "anchor" and "barb" may be used interchangeably. In certain embodiments, the anchors 104 are sufficient to secure the annuloplasty ring 100 to the annulus of the heart valve such that additional suturing of the annuloplasty ring to the valve annulus is not needed. As shown in FIG. 1A, the anchors 104 may be within the body member 101 in an insertion geometry. As shown in FIG. 1B, the anchors 104 may be curved in a deployed configuration. In other embodiments, the anchors 104 may have other shapes, such as linear or helical deployed configurations. In certain embodiments, the anchors 104 may include a shape memory material (such as, for example, nitinol) that is heat set to a deployed configuration (such as, for example, a curved configuration, a linear configuration, or a helical configuration). Those with ordinary skill in the art will recognize that combinations of different deployed anchor configurations may also be used without departing from the scope of the present disclosure.

The anchors 104 may be superelastic such that applying sufficient stress places the anchors into an introduction configuration and releasing the stress allows the anchors to resume their respective deployed configurations. In certain embodiments, the anchors 104 may lay flat against the body member 101 in the introduction configuration during insertion of the annuloplasty ring 100 through the catheter. As described in greater detail herein, in other embodiments, the anchors 104 may be retracted inside the hollow body member 101 of the annuloplasty ring 100 in the introduction configuration during insertion of the annuloplasty ring 100 through the catheter. In such embodiments, the anchors 104 may be selectively deployed at a desired time (such as, for example, after the annuloplasty ring 100 is properly positioned against, or in abutment with, the annulus of the heart valve). In certain embodiments, the superelastic property of the anchors 104 may be used to self-propel the anchors into the annulus of the heart valve. The anchors 104 may be configured to be deployed from within the body member 101 through the anchor windows 110.

The ring closure lock 106 may be used to secure two open ends of the annuloplasty ring 100 to form a closed ring of the operable geometry. In certain embodiments, the ring closure lock 106 may include a female snap and a male snap. As discussed in greater detail herein, the annuloplasty ring 100 may be "snap locked" using wires or sutures to pull a male snap into a female snap. The ring closure lock 106 of the illustrated annuloplasty ring 100 of FIGS. 1A and 1B may be disposed at a posterior side of the annuloplasty ring. The ring closure lock 106 may allow an angled coupling of the two ends, such as, for example, at an apex of a curved side of a D-shaped annular operable geometry.

The pivot 108 may be used to automatically rotate the annuloplasty ring 100 after it exits the catheter within the heart to align the plane of the annuloplasty ring 100 (in the annular operable geometry) with the plane of the heart valve. The annuloplasty ring 100 may be pushed from the catheter in a direction that is substantially perpendicular to the plane of the heart valve (such as, for example, parallel to the general direction of blood flow through the valve). Upon exiting the catheter, the annuloplasty ring 100 may be rotated at or about the pivot 108 to allow proper positioning of the annuloplasty ring 100 against the annulus. With the annuloplasty ring 100 properly oriented in alignment with the plane of the heart valve, the annuloplasty ring 100 may be expanded to the expanded state. For example, an expansion tool may be used to expand the annuloplasty ring 100, as shown in FIGS. 10, 11, 12A-12E, 13A-13D, and 14A-14B and described in greater detail herein. The annuloplasty ring 100 in the expanded state may be pressed against the valve annulus before deploying the anchors 104, and an act of deploying the anchors may drive the anchors into the adjacent tissue. A positioning tool may facilitate expansion and/or proper positioning/orientation of the annuloplasty ring 100 against the heart valve annulus. A stabilizer, such as a tripod tool or a bipod tool, shown for example in FIGS. 12A-12E, 13A-13D, and 14A-14B and described in greater detail herein, may be used to position the annuloplasty ring 100 in abutment against the annulus of the target heart valve, or otherwise in intimate contact with the annulus of the target heart valve. In addition, fluoroscopy, ultrasound, and/or other imaging techniques may be used to assist in properly positioning the annuloplasty ring 100 against the heart valve annulus.

Although not shown in FIGS. 1A and 1B, certain ring embodiments may include a selectively adjustable member for changing the size and/or shape of the annuloplasty ring 100 postoperatively to compensate for changes in the size of the heart and/or the treated heart valve. An illustrative example of an adjustable member may be a member made of a material that can be adjusted via the application of energy, such as, for example RF energy, light energy, or thermal energy.

Figure 1C:
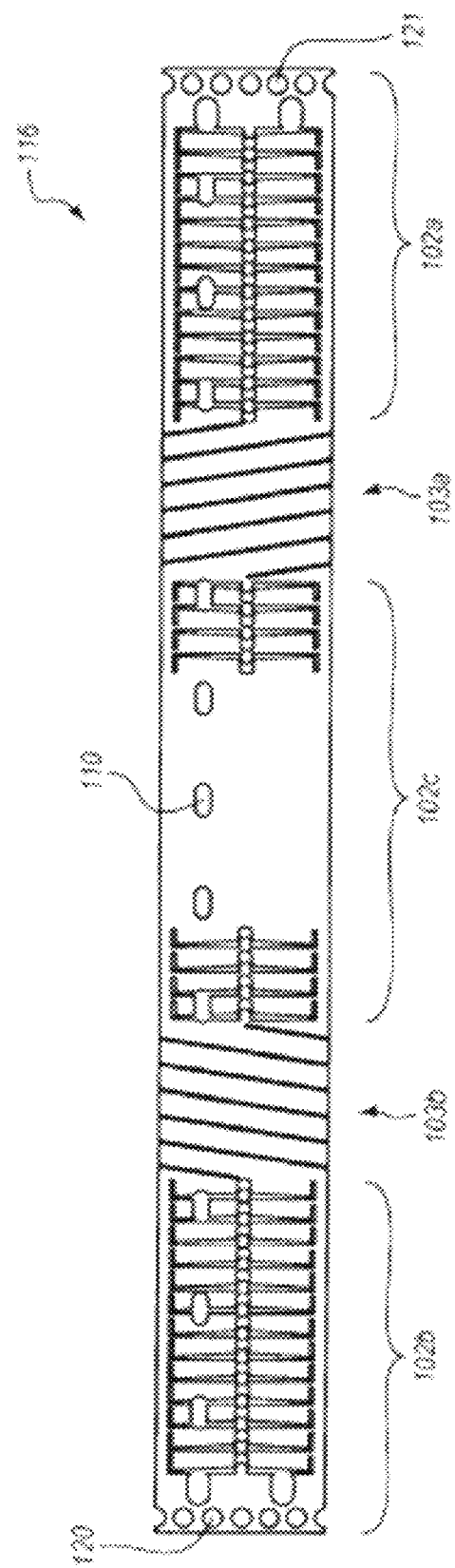
FIG. 1C depicts a schematic diagram of an illustrative cutting pattern used for laser processing a hypotube of an adjustable annuloplasty ring according to an embodiment.

FIG. 1C depicts a schematic diagram of an illustrative cutting pattern, generally designated 116, used for laser processing a hypotube to form a body member 101 of an adjustable annuloplasty ring 100 according to an embodiment. The pattern 116 may enable a hypotube or outer tube (also referred to herein as an "outer hollow member") to be cut for use as a body member 101 of an annuloplasty ring 100 according to an embodiment. The cutting pattern 116 may correspond to the entire body member 101 as if the body member were cut along a longitudinal axis and unrolled. The cutting pattern 116 may enable cutting the hypotube to form the plurality of regions 102 and the integral biasing 101 elements 103. The cutting pattern 116 shown in FIG. 1C may define the configuration of the plurality of regions 102 and how the regions 102 interact with adjacent regions as the body member 101 transitions from the elongate insertion geometry shown to the annular operable geometry.

The cutting pattern 116 may also enable cutting the hypotube to form one or more holes 120, 121 at each end to allow one or more pins (not shown) to couple male and/or female components of the ring closure lock 106 to respective ends of the body member 101. The cutting pattern 116 may also enable cutting the hypotube to form anchor windows 110 through which the plurality of anchors 104 may be deployed.

FIG. 2A depicts a schematic diagram of a perspective view of an illustrative adjustable annuloplasty ring, generally designated 200, according to an embodiment. The annuloplasty ring 200 may be in an annular (D-shaped) operable geometry and a contracted state. FIG. 2B depicts a schematic diagram of a perspective view of an illustrative adjustable annuloplasty ring 200 in an expanded state. The annuloplasty ring 200 may be configured to enable percutaneous, transcatheter annuloplasty to repair a heart valve.

Referring collectively to FIGS. 2A and 2B, the annuloplasty ring 200 may include a body member 201 having a plurality of regions 202a, 202b, 202c (collectively 202), a plurality of biasing elements 203a, 203b (collectively 203), a plurality of anchors 204, a ring closure lock 206, and a pivot 208. The body member 201 may be a "D-shape" in the operable geometry, but those having ordinary skill in the art will recognize that other annular-shaped operable geometries may also be used without departing from the scope of the present disclosure. For example, circular or oval operable geometries may be used. Different from the annuloplasty ring 100 of FIGS. 1A-1B, the ring closure lock 206 may be disposed on the anterior side of the annuloplasty ring 200 (rather than the posterior side).

In addition to the operable geometry shown in FIGS. 2A and 2B, the body member 201 may be transitionable from an elongate insertion geometry (see, for example, FIG. 9C) to the annular operable geometry shown in FIGS. 2A and 2B. The elongate insertion geometry may allow the annuloplasty ring 200 to be inserted into and passed through a catheter for percutaneous passage of the annuloplasty ring into the heart of a patient. A transition from an elongate insertion geometry to an annular operable geometry is illustrated in FIGS. 9C-9F, and discussed herein with reference to the same.

Once in an annular operable geometry, the annuloplasty ring 200 may have a contracted state as shown in FIG. 2A and an expanded state as shown in FIG. 2B. The biasing elements 203 may be configured to allow expansion of the body member 201 to increase the A-P distance of the annuloplasty ring 200 to an expanded state. In situ within the heart, expansion of the body member 201 to the expanded state may enlarge the annuloplasty ring 200 to a size conforming, or approximately conforming, to an annulus of a target heart valve to be repaired. Expansion of the body member 201 may be accomplished by an expansion tool, such as a balloon, a cage, or another expansion tool, such as is shown in FIGS. 10, 11, 12A-12E, 13A-13D, and 14A-14B, and described in greater detail herein. In the illustrated embodiment of FIGS. 2A and 2B, a biasing element 203a disposed between a first anterior region 202a and a posterior region 202c and a biasing element 203b disposed between a second anterior region 202b and the posterior region 202c may enable a desired expansion from the contracted state shown in FIG. 2A to the expanded state shown in FIG. 2B.

The expanded state of FIG. 2B may be such that the annuloplasty ring 200 is disposed in abutment with, or in intimate contact with, the annulus of the target valve. Disposing the annuloplasty ring 200 in intimate contact with the annulus may enhance an anchoring process in which the plurality of anchors 204 is deployed to fasten the annuloplasty ring 200 to the annulus.

Once the annuloplasty ring 200 is fastened to the annulus, it may be contracted from the expanded state of FIG. 2B back to the contracted state of FIG. 2A to reduce a diameter of the annulus of the target valve. Contraction of the annuloplasty ring 200 may include the first and second anterior regions 202a, 202b of the body member 201 moving in a telescopic manner into the posterior region 202c as the biasing members 203 force movement of the first and second anterior regions of the body member toward the posterior region. Contraction of the annuloplasty ring 200 from the expanded state to the contracted state may decrease the A-P distance of the annuloplasty ring and, with the plurality of anchors 204 securing the annuloplasty ring to the annulus, may also decrease the A-P distance of the target valve to improve leaflet coaptation and reduce regurgitation through the target valve.

In the illustrated embodiment of FIGS. 2A and 2B, contraction of the annuloplasty ring 200 from the expanded state to the contracted state may be accomplished by the biasing elements 203. The biasing elements 203 may bias the annuloplasty ring 200 toward the contracted state such that expansion of the annuloplasty ring 200 to the expanded state stores potential energy in the biasing elements. Releasing the biasing elements 203 (for example, releasing or otherwise removing an expansion tool and/or expansion force) releases the stored potential energy and thereby forces movement of the first anterior region 202a and the second anterior region 202b of the body member 201 toward the anterior region 202c of the body member to decrease the A-P distance of the annuloplasty ring 200 to the contracted state. In other words, the biasing elements 203, upon release, may actively transition the annuloplasty ring 200 from an expanded state to the contracted state.

The biasing elements 203 of the illustrated annuloplasty ring 200 of FIGS. 2A and 2B may include springs or another similar element that is non-integral to the body member. The springs of the biasing elements 203 may allow the anterior regions 202a, 202b to move away from the first posterior region 202c, thereby increasing the A-P distance of the annuloplasty ring 200.

The A-P distance AP1 of the contracted state of FIG. 2A may be enlarged a distance d upon expansion of the annuloplasty ring 200 such that the A-P distance AP2 of the expanded state FIG. 2B is larger (AP2=AP1+d). The springs of the biasing elements 203 may be biased toward a relaxed position, or the contracted state as shown in FIG. 2A, such that expansion of the springs stores potential energy and release of the springs results in a release of potential energy and contraction toward the contracted state.

In various embodiments, the plurality of anchors 204 may be configured to secure the annuloplasty ring 200 to the annulus of the heart valve. In FIGS. 2A and 2B, the anchors 204 may be curved in the illustrated deployed configuration. The anchors 204 in other embodiments may include other shapes, such as, for example, linear or helical deployed configurations. In certain embodiments, the anchors 204 may include a shape memory material (such as, for example, nitinol) that is heat set to a deployed configuration (for example, curved configuration, linear configuration, or helical configuration). Those with ordinary skill in the art will recognize that combinations of different deployed anchor configurations may also be used without departing from the scope of the present disclosure.

The anchors 204 may be superelastic such that applying sufficient stress places the anchors into an introduction configuration and releasing the stress allows the anchors to resume their respective deployed configurations. In certain embodiments, the anchors 204 may lay flat against the body member 201 in the introduction configuration during insertion of the annuloplasty ring 200 through the catheter. As discussed below, in other embodiments, the anchors 204 may retract inside a hollow body member 201 of the annuloplasty ring 200 in the introduction configuration during insertion of the annuloplasty ring through the catheter. In such embodiments, the anchors 204 may be selectively deployed at a desired time (for example, after the annuloplasty ring 200 is properly positioned against, or in abutment with, the annulus of the heart valve). In certain embodiments, the superelastic property of the anchors 204 may be used to self-propel the anchors into the annulus of the heart valve.

The ring closure lock 206 may be used to secure two open ends of the annuloplasty ring 200 to form a closed ring of the operable geometry. Different from the annuloplasty ring 100 of FIGS. 1A-1B, the ring closure lock 206 may be disposed on the anterior side of the annuloplasty ring 200 (rather than the posterior side). In certain embodiments, the ring closure lock 206 may include a female snap and a male snap. The annuloplasty ring 100 may be "snap locked" using wires or sutures to pull a male snap into a female snap.

The pivot 208 may facilitate rotation of the annuloplasty ring 200 after it exits the catheter within the heart to align the plane of the annuloplasty ring (in the annular operable geometry) with the plane of the heart valve, as previously described herein.

Figure 3A:
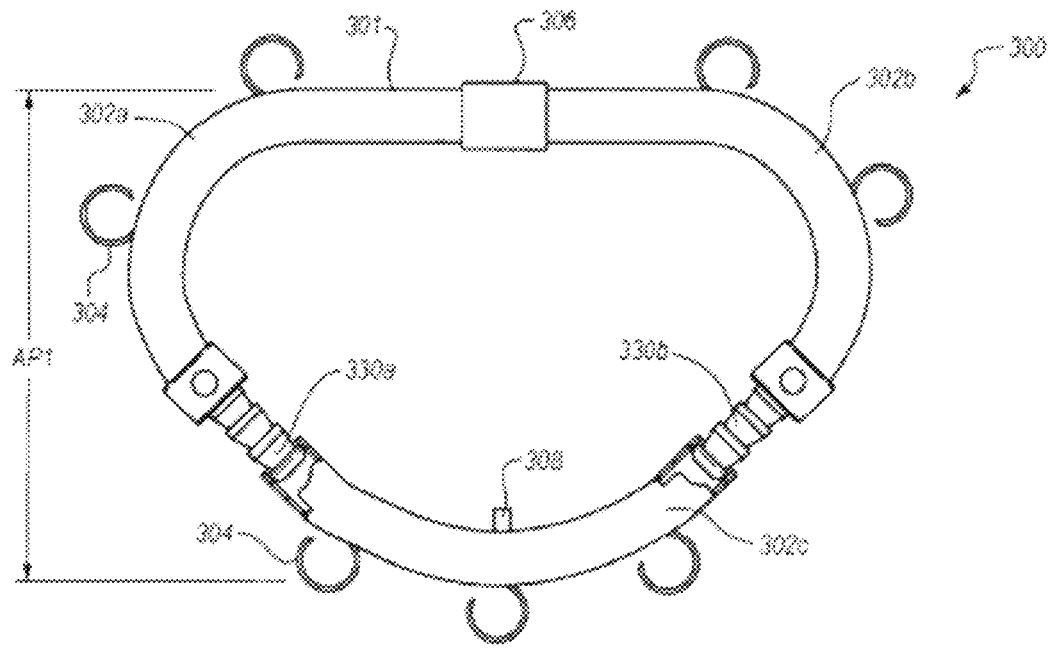
FIG. 3A depicts a schematic diagram of a perspective view of a second illustrative adjustable annuloplasty ring in an annular (D-shaped) operable geometry and in an expanded state according to an embodiment.
Figure 3B:
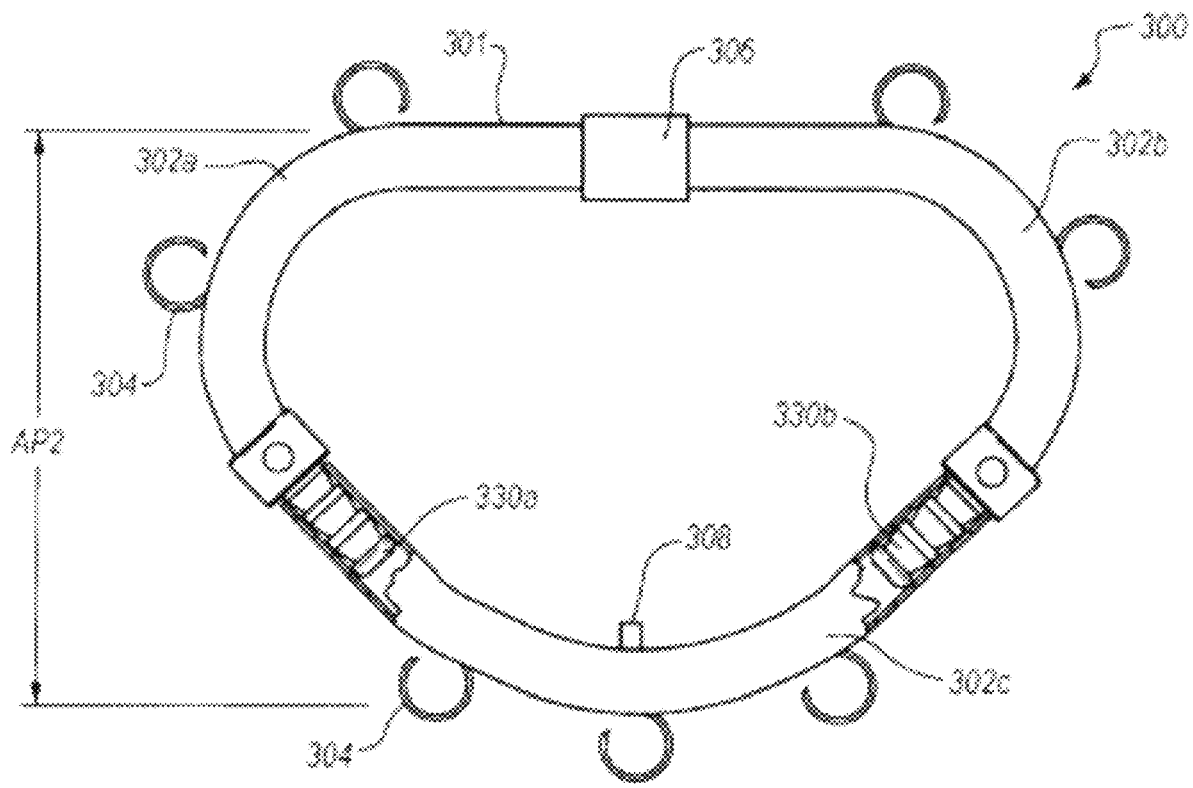
FIG. 3B depicts a schematic diagram of a perspective view of a second illustrative adjustable annuloplasty ring in a contracted state according to an embodiment.

FIG. 3A depicts a schematic diagram of a perspective view of an illustrative adjustable annuloplasty ring 300 according to another embodiment. The annuloplasty ring 300 may be in an annular (D-shaped) operable geometry and an expanded state. FIG. 3B depicts a schematic diagram of a perspective view of the adjustable annuloplasty ring 300 of FIG. 3A in a contracted state. The annuloplasty ring 300 may be configured to enable percutaneous, transcatheter annuloplasty to repair a heart valve.

Referring collectively to FIGS. 3A and 3B, the annuloplasty ring 300 may include a body member 301 having a plurality of regions 302a, 302b, 302c (collectively 302), a plurality of anchors 304, a ring closure lock 306, and a pivot 308, similar to previously described embodiments. The annuloplasty ring 300 may be transitionable from an elongate insertion geometry (see, for example, FIG. 9C) to the annular operable geometry shown in FIGS. 3A and 3B. The elongate insertion geometry may allow the annuloplasty ring 300 to be inserted into and passed through a catheter for percutaneous passage of the annuloplasty ring into the heart of a patient, as illustrated in FIGS. 9C-9F and discussed in greater detail herein.

The plurality of regions 302 of the illustrated annuloplasty ring 300 of FIGS. 3A and 3B may be separate, individual segments. The segments 302 may be coupled together by stepped connectors 330a, 330b (collectively 330) in the annular operable geometry. The stepped connectors 330 may be configured to enable the body member 301 to be adjustable to decrease the A-P distance of the annuloplasty ring 300 from an expanded state as shown in FIG. 3A to a contracted state as shown in FIG. 3B. The stepped connectors 330 may initially couple the posterior segment 302c to each of a first anterior segment 302a and a second anterior segment 302b in the expanded state of FIG. 3A, conforming, or approximately conforming, to an annulus of a target heart valve to be repaired. The expanded state of FIG. 3A may be such that the annuloplasty ring 300 is disposed in abutment with, or in intimate contact with, the annulus of the target valve, thereby enhancing an anchoring process in which the plurality of anchors 304 are deployed to fasten the annuloplasty ring to the annulus.

Once the annuloplasty ring 300 is fastened to the annulus, it may be contracted from the expanded state of FIG. 3A to the contracted state of FIG. 3B to reduce a diameter of the annulus of the target valve. Contraction of the annuloplasty ring 300 may include the stepped connectors 330 moving in a telescopic manner into the posterior region 302c as the first and second anterior regions 302a, 302b of the body member 301 move toward the posterior region. Contraction of the annuloplasty ring 300 from the expanded state to the contracted state may decrease the A-P distance of the annuloplasty ring and, with the plurality of anchors 304 securing the annuloplasty ring 300 to the annulus, may also decrease an A-P distance of the target valve to improve leaflet coaptation and reduce regurgitation through the target valve. The stepped connectors 330 may allow for multiple degrees of adjustment. For example, a stepped connector having two engagement steps (see engagement steps 402 in FIGS. 4A and 4B) may allow two degrees of adjustment, as discussed in greater detail herein.

In the illustrated embodiment of FIGS. 3A and 3B, contraction of the annuloplasty ring 300 from the expanded state to the contracted state may be accomplished percutaneously through use of sutures or wires to force the posterior segment 302c toward the first and second anterior segments 302a, 302b and vice versa.

In certain embodiments, a biasing element (not shown in FIGS. 3A and 3B) may bias the annuloplasty ring 300 toward the contracted state and aid in contraction of the annuloplasty ring 300 from the expanded state to the contracted state. In other embodiments, a biasing element may enable expansion from an initial state to an expanded state, and a stepped connector 330 may operate to ensure expansion from the contracted state is restricted.

Different from the embodiments of FIGS. 1A-1C and 2A-2B, the annuloplasty ring 300 of FIGS. 3A and 3B may initially be in an expanded state upon transition to the annular operable geometry. In other words, the initial A-P distance AP1 of the annuloplasty ring 300 may be sufficient to conform or substantially conform to the A-P distance of a target valve. The A-P distance AP1 of the expanded state of FIG. 3A may be decreased by a distance d upon contraction of the annuloplasty ring 300 such that the A-P distance AP2 of the contracted state FIG. 3B is smaller (AP2=AP1−d). The decrease of the A-P distance, with the anchors fastening the annuloplasty ring 300 to the annulus of the valve, may decrease the A-P distance of the target valve to improve leaflet coaptation of the target valve and reduce regurgitation through the target valve.

Figure 4A:
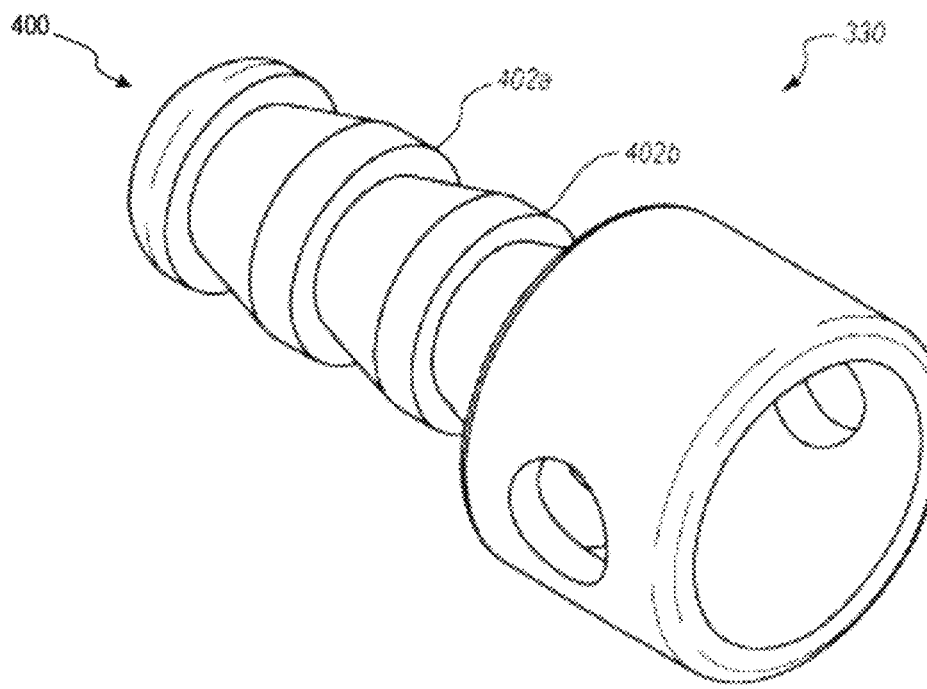
FIGS. 4A and 4B depict a perspective view and a cross-sectional view, respectively, of an illustrative stepped connector of an adjustable annuloplasty ring according to an embodiment.
Figure 4B:
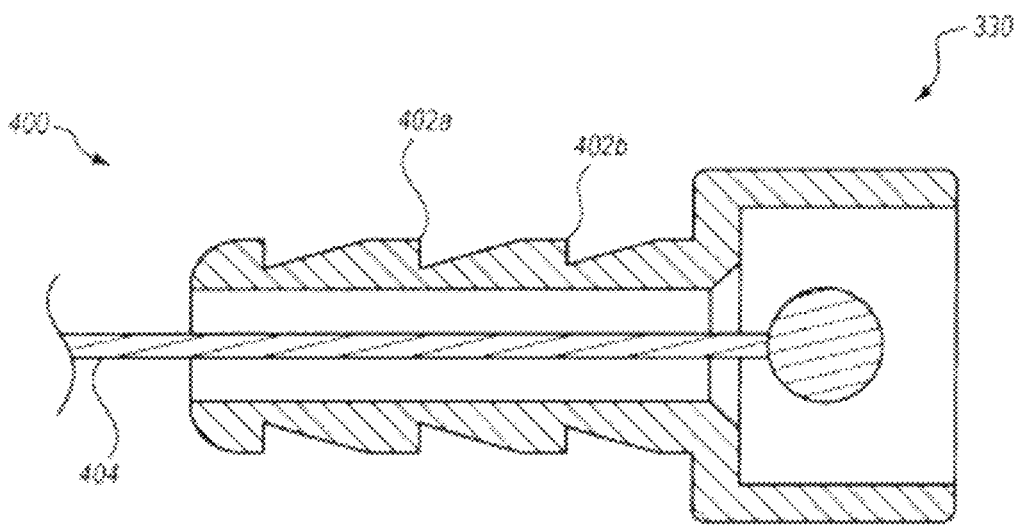

FIGS. 4A and 4B depict a perspective view and a cross-sectional view, respectively, of a male component 400 of a stepped connector 330 of an adjustable annuloplasty ring 300 according to an embodiment. A corresponding female component (not shown) may be configured to receive the male component 400 to form the stepped connector 330. The stepped connector 330 may include two engagement steps 402a, 402b (collectively 402) to allow two degrees of adjustment and/or gradual adjustment. As shown in FIG. 4B, a cable 404 or suture may couple to the male component 400 of the stepped connector 330. The cable 404 or suture may enable a force to move the male component 400 in a telescopic manner into a female component of the stepped connector 330. Contraction of the annuloplasty ring 300 until engagement of a first engagement step 402a within the female component may secure the annuloplasty ring in a partially contracted state. Further contraction of the annuloplasty ring 300 to engagement of a second engagement step 402b within the female component may secure the annuloplasty ring in the contracted state. In this manner, the stepped connector 330 may enable two degrees of adjustment (and for gradual adjustment) of the A-P distance of the annuloplasty ring.

Figure 5A:
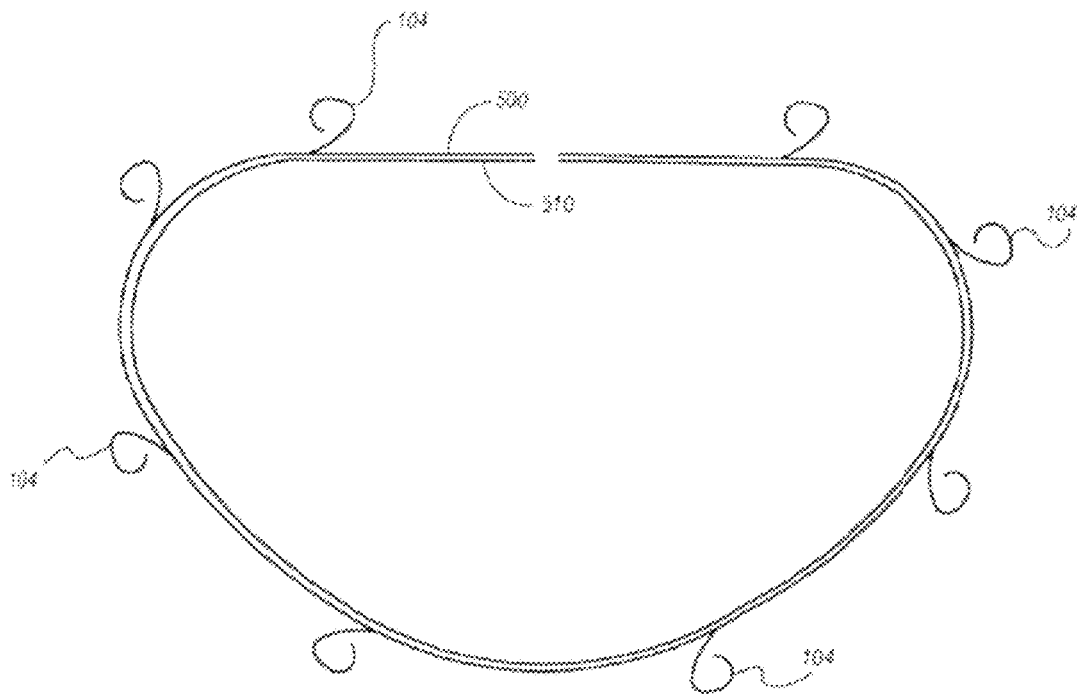
FIG. 5A depicts a schematic diagram illustrating a side view of an internal anchor ribbon including a plurality of curved anchors according to an embodiment.

FIG. 5A depicts a schematic diagram illustrating a side view of an illustrative internal anchor ribbon 500 including the curved anchors 104 shown in FIGS. 1A and 1B according to an embodiment. In certain embodiments, deployment of the anchors 104 may be accomplished using an internal anchor member, such as anchor ribbon 500, that is selectively movable within a hollow tube of the body member 101 (FIG. 1A). The curved anchors 104 may be affixed (for example, laser welded) to the internal anchor ribbon 500 or directly cut into the internal anchor ribbon. Like the anchors 104, the internal anchor ribbon 500 may include a superelastic shape memory material (such as, for example, nitinol). The shape memory of the anchor ribbon 500 may be heat set to the same memorized annular shape as the plurality of regions 102 of the body member 101 in the contracted state of the annular operable geometry, as shown in FIG. 1A.

The internal anchor ribbon 500 may be slidable (for example, using wires or sutures accessible through the catheter) in the hollow body member 101 of the annuloplasty ring 100. To reduce friction between the internal anchor ribbon 500 and the body member 101, certain ring embodiments may include an internal glide ribbon 510. The internal glide ribbon 510 may include a low-friction material (for example, as a coating or covering) such as polytetrafluoroethylene (PTFE) or other polymer. In addition, or in other embodiments, the internal glide ribbon 510 may include a superelastic shape memory material (such as, for example, nitinol) that is heat set to the same memorized annular shape as the body member 101. Thus, in particular embodiments, three D-shaped superelastic members (the outer tube of the body member 101, the internal anchor ribbon 500, and the internal glide ribbon 510) may be included, which may cooperate to increase the rigidity of the annuloplasty ring 100.

In various embodiments, as shown in FIGS. 5F and 5G, the internal anchor ribbon may be a tube-like polymeric element 502 having a curved wall 503 and an opening 504 therethrough. In some embodiments, the polymeric element 502 may be located inside the ring 101 (FIGS. 1A and 1B) such that the anchors 104 (FIGS. 5A-5C) slide inside the ring. The general shape and/or pattern of the polymeric element 502 is not limited by this disclosure, and may generally be any pattern that allows for movement of the anchors 104 (FIGS. 5A-5C) inside the ring 101 (FIGS. 1A and 1B), as described herein. For example, FIGS. 5H, 5I, and 5J depict a top view, a first side view, and a second side view, respectively, of an illustrative pattern for a polymeric element 502. The polymeric material 502 may generally be made of any material now known or later developed to reduce friction and facilitate sliding of the anchors 104 (FIGS. 5A-5C) within the ring. Illustrative materials may include, but are not limited to, polytetrafluoroethylene (PTFE), fluorinated ethylene propylene (FEP), polyether block amide (PEBA), and/or the like. In addition, the polymeric element 502 may be constructed by any method now known or later developed, including, but not limited to, an extrusion method, an injection molding method, a machining method, and/or the like.

Figure 5B:
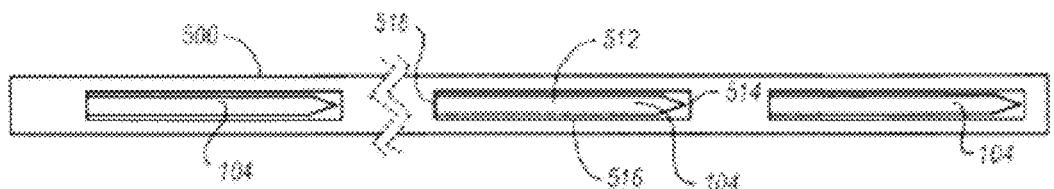
FIG. 5B depicts a schematic diagram of a top view of illustrative anchors cut into an internal anchor ribbon in an elongate insertion geometry according to an embodiment.
Figure 5C:
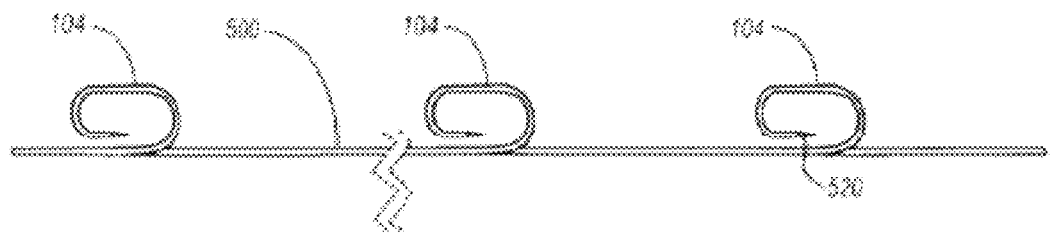
FIG. 5C depicts a schematic diagram of a side view of an illustrative internal anchor ribbon in an elongate insertion geometry and a plurality of anchors in a curled or curved deployed configuration according to an embodiment.
Figure 5D:
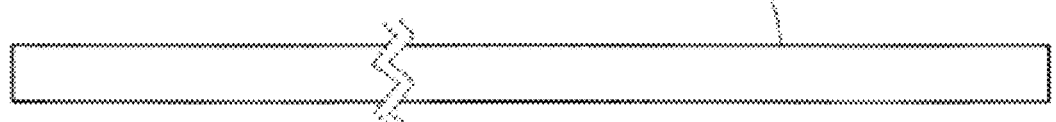
FIG. 5D depicts a schematic diagram of a top view of an illustrative internal glide ribbon in an elongate insertion geometry according to an embodiment.
Figure 5E:
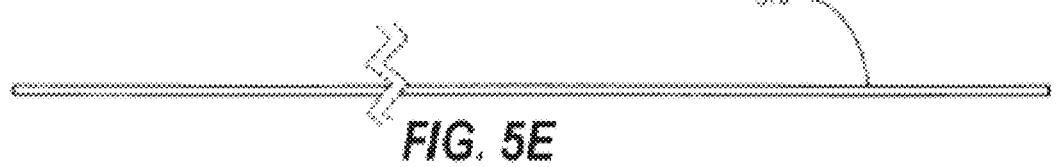
FIG. 5E depicts a schematic diagram of a side view of an illustrative internal glide ribbon according to an embodiment.

FIG. 5B depicts a schematic diagram of a top view of the anchors 104 cut into the internal anchor ribbon 500 shown in FIG. 5A in the elongate insertion geometry according to an embodiment. In some embodiments, a laser may be used to cut the anchors 104 along a first side 512, a second side 514 (for example, in a pointed or tip shape), and a third side 516, while leaving a fourth side 518 of the anchor 104 uncut and attached to the internal anchor ribbon 500. After cutting, the anchors 104 may be heat set to the desired memorized shape for the deployed configuration. For example, FIG. 5C depicts a schematic diagram of a side view of the internal anchor ribbon 500 in the elongate insertion geometry and the anchors 104 in a curled or curved deployed configuration according to an embodiment. The amount of curvature in the deployed configuration of the anchors 104 may depend on the particular application. In the example shown in FIG. 5C, the anchors 104 may fold back on themselves such that the prong or tip 520 points parallel to or away from the internal anchor ribbon 500. FIG. 5D depicts a schematic diagram of a top view of the internal glide ribbon 510, and FIG. 5E depicts a schematic diagram of a side view of the internal glide ribbon 510, in the elongate insertion geometry according to an embodiment.

Figure 6A:
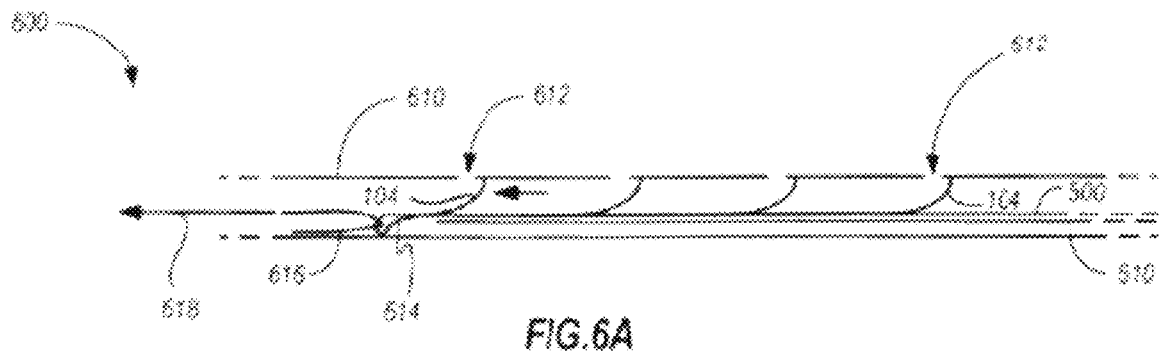
FIGS. 6A and 6B depict schematic diagrams of cross-sectional side views of an annuloplasty ring before (FIG. 6A) and after (FIG. 6B) deployment of a plurality of anchors according to an embodiment.
Figure 6B:
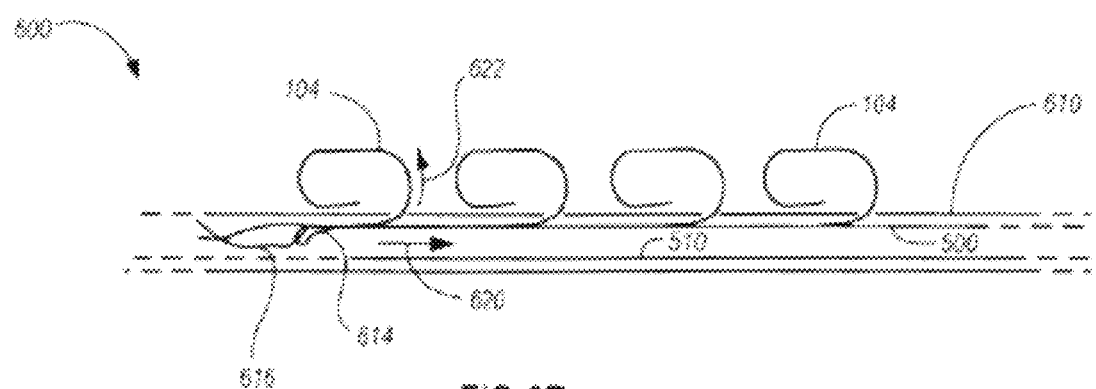

FIGS. 6A and 6B depict schematics of cross-sectional side views of an annuloplasty ring 600 before (FIG. 6A) and after (FIG. 6B) deployment of the anchors 104 shown in FIGS. 5A-5C according to an embodiment. For illustrative purposes, the annuloplasty ring 600 in FIGS. 6A and 6B is shown in an elongate insertion geometry. Those having ordinary skill in the art will recognize, however, that the anchors 104 may generally be deployed when the annuloplasty ring 600 is in the annular operable geometry without departing from the scope of the present disclosure.

The illustrated annuloplasty ring 600 may include an outer tube 610 (for example, formed by the body member 101 shown in FIG. 1) including a plurality of anchor deployment windows 612. During the manufacturing of the annuloplasty ring 600, and before the annuloplasty ring is loaded into the catheter, the internal anchor ribbon 500 and the internal glide ribbon 510 may be inserted into the outer tube 610 in a position where the anchors 104 are prevented from exiting through the windows 612. As shown in FIG. 6A, inserting the internal anchor ribbon 500 into the outer tube 610 may prevent the anchors from assuming their fully curved deployed configuration.

For deploying the anchors 104, the internal anchor ribbon 500 may include (or may be attached to) a hook or loop 614 for engaging a wire or suture 616 that may be pulled by a user through the catheter (for example, in the direction of arrow 618 in FIG. 6A) to move the tip of each anchor 104 to a corresponding window 612. In particular embodiments, the anchors 104 and windows 612 may be arranged such that the tip of each anchor 104 reaches its respective window 612 at substantially the same time as the other anchor/window pairs. As shown in FIG. 6B, once the tips of the anchors 104 reach the respective windows 612, the superelasticity of the anchors may propel the internal anchor ribbon 500 in the opposite direction (as indicated by arrow 620) as the anchors spring out the windows (as indicated by arrow 622) to resume their curved configurations. As the anchors 104 drive through the windows 612, the anchors may drive into surrounding tissue (for example, the heart valve annulus). The superelasticity of the anchors 104 may allow the anchors to be self-propelled into the tissue adjacent or proximate to the annuloplasty ring 600.

Figure 6C:
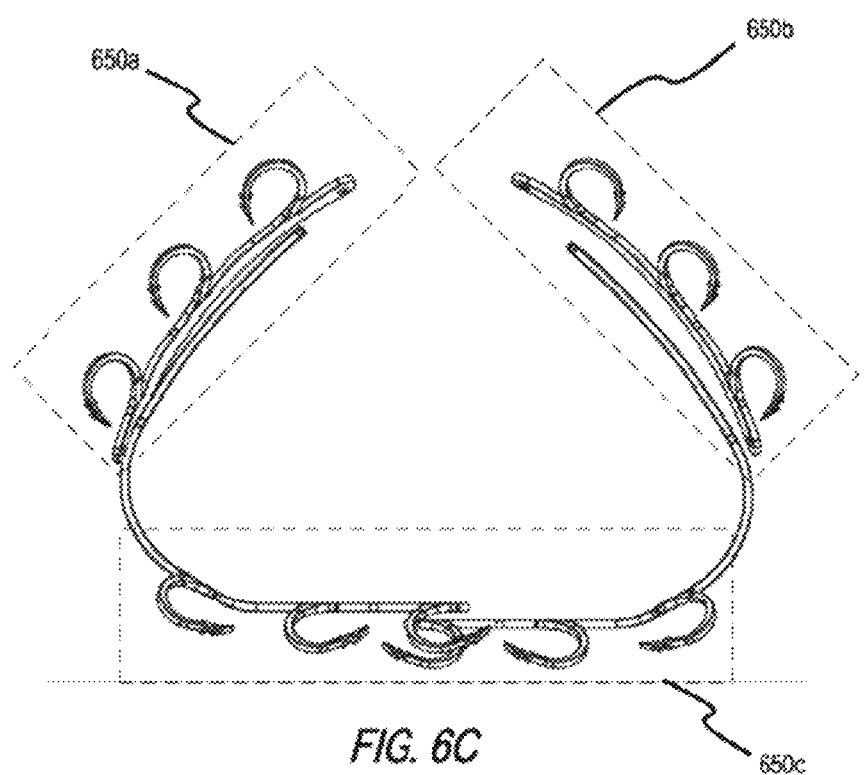
FIG. 6C depicts a schematic diagram of a side view of various segments of illustrative internal anchors according to an embodiment.

In some embodiments, as shown in FIG. 6C, the anchors 104 may be divided into a plurality of segments 650a, 650b, 650c. While FIG. 6C depicts 3 segments, those having ordinary skill in the art will recognize that any number of segments may be used without departing from the scope of the present disclosure. For example, the anchors 104 may be divided into 2 segments, 3 segments, 4 segments, 5 segments, 6 segments, or more. Dividing the anchors 104 into a plurality of segments 650a, 650b, 650c may allow for actuation of one or more of the segments at a time such that the actuated segment deploys its respective anchor(s) 104 while the remaining anchors remain non-deployed. In some embodiments, various segments 650a, 650b, 650c may be actuated sequentially. In other embodiments, various segments 650a, 650b, 650c may be actuated simultaneously. In some embodiments, various segments 650*a*, 650*b*, 650*c* may be actuated based upon which anchors 104 an operator desires to deploy, which may be based upon the positioning and location of the annuloplasty ring. In some embodiments, the segments 650*a*, 650*b*, 650*c* may be arranged in a plurality of zones. For example, a posterior side may be a first zone having a first plurality of segments, and an anterior side may be a second zone having a second plurality of segments. Thus, the anterior zone may be deployed separately from the posterior zone, or at substantially the same time.

Figure 7:
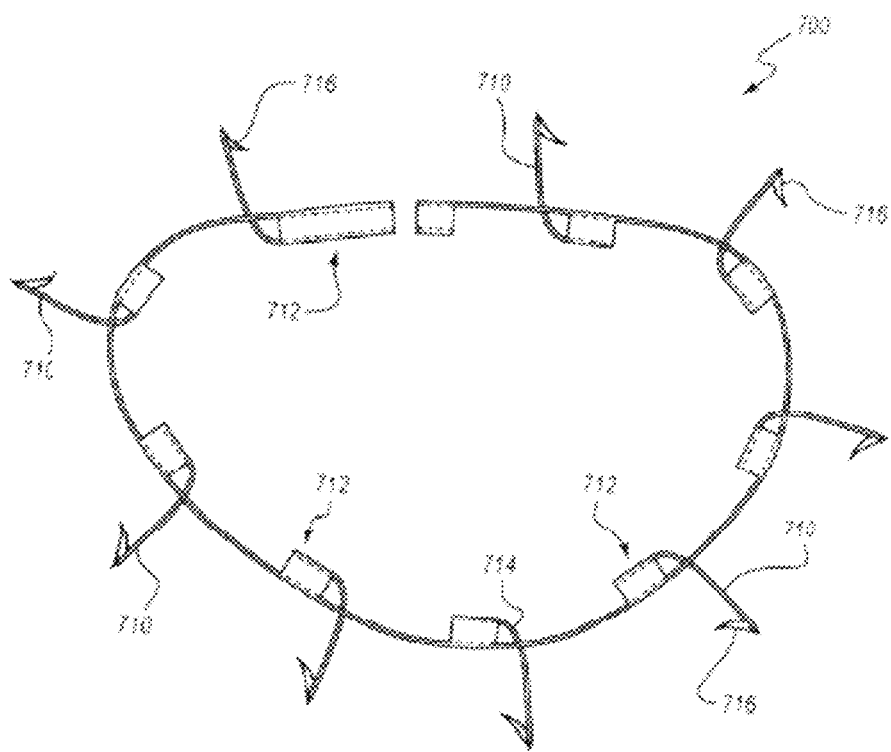
FIG. 7 depicts a schematic diagram of a side view of an illustrative internal anchor member including linear anchors according to an embodiment.

FIG. 7 depicts a simplified schematic diagram of a side view of an illustrative internal anchor member (or members) 700 including linear anchors 710 according to an embodiment. The linear anchors 710 may be affixed (for example, laser welded) to the internal anchor member 700. In the embodiment shown in FIG. 7, however, the internal anchor member 700 and linear anchors 710 may be cut from a single superelastic shape memory (such as, for example, nitinol) hypotube. FIG. 7, for example, shows remaining tubular portions 712 after the hypotube is cut to form prongs 714 of the linear anchors 710. The remaining tubular portions 712 may facilitate sliding (for example, using wires or sutures accessible through the catheter) the internal anchor member 700 coaxially within the hollow tube of the annuloplasty ring (for example, within the annuloplasty ring 600 shown in FIGS. 6A and 6B).

The internal anchor member 700 may be heat set to the same memorized annular shape as the annuloplasty ring 600. The anchor prongs 714 may be heat set to protrude outward through windows cut in the annuloplasty ring 600. Barbs 716 may be laser welded to the prongs 714 to form the linear anchors 710. The linear anchors 710 may be retracted/deployed by sliding the internal anchor member 700 within the annuloplasty ring 600.

Figure 8A:
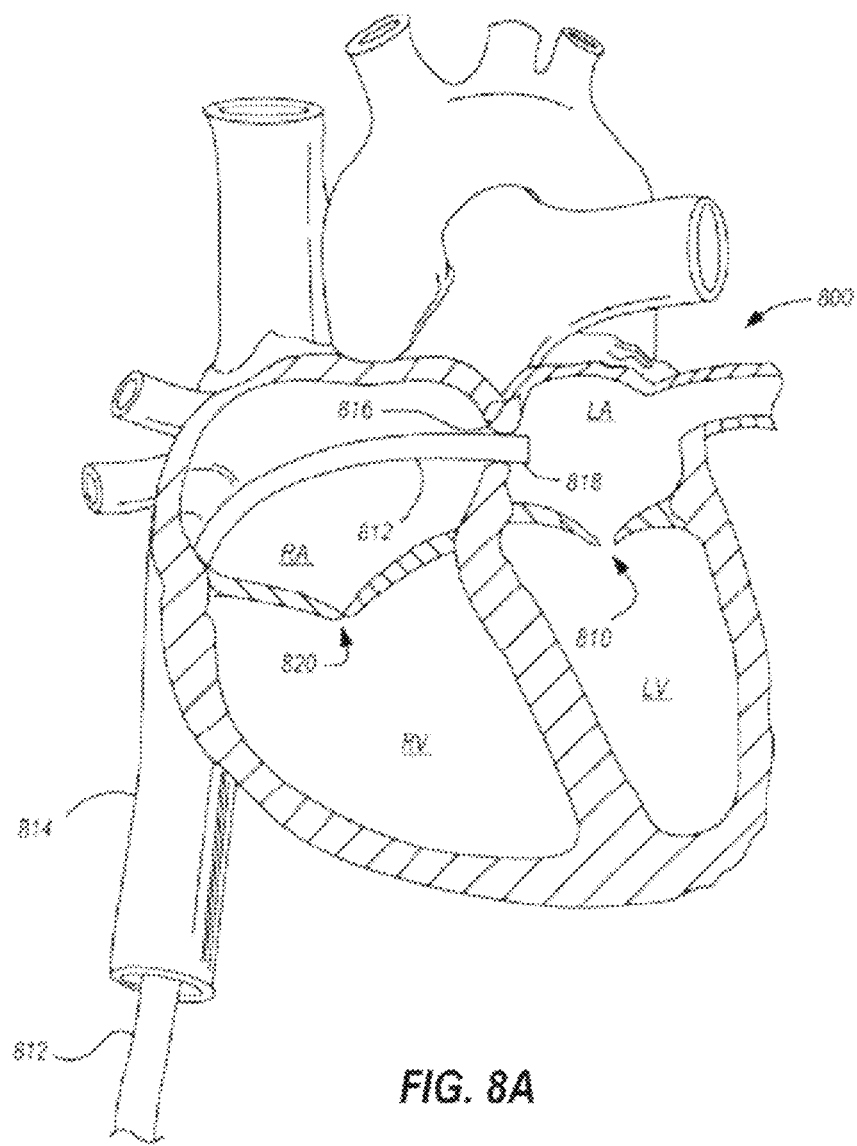
FIG. 8A depicts a schematic diagram of an illustrative trans-septal approach for endovascular delivery of an annuloplasty ring to the mitral valve of a heart according to an embodiment.

As described herein, the annuloplasty ring may be configured for percutaneous transcatheter delivery and fixation to heart valves. The annuloplasty ring may be delivered through a catheter to the mitral valve, for example, using a trans-septal approach, a retrograde approach, or a trans-apical approach. For example, FIG. 8A depicts a schematic diagram of an illustrative trans-septal approach for endovascular delivery of an annuloplasty ring (not shown) to the mitral valve 810 of a heart 800 according to an embodiment. For illustrative purposes, a partial cross-section of the heart 800 is illustrated to show the right atrium RA, right ventricle RV, left atrium LA, and left ventricle LV. For clarity, certain features (for example, papillary muscles and chordae tendineae) are not shown. In the trans-septal approach shown in FIG. 8A, the left atrium LA may be approached by advancement of a catheter 812 through the inferior vena cava 814, into the right atrium RA, across the interatrial septum 816, and into the left atrium LA. The annuloplasty ring may be delivered through the catheter 812 into the atrium and anchored to the annulus of the mitral valve 810.

As shown in FIG. 8A, the catheter 812 may be delivered percutaneously into the heart 800. A guiding sheath (not shown) may be placed in the vasculature system of the patient and used to guide the catheter 812 and its distal end 818 to a desired deployment site. In some embodiments, a guide wire (not shown) may be used to gain access through the superior or inferior vena cava 814, for example, through groin access for delivery through the inferior vena cava 814. The guiding sheath may be advanced over the guide wire and into the inferior vena cava 814 shown in FIG. 8A. The catheter 812 may be passed through the right atrium RA and toward the interatrial septum 816. Once the distal end 818 of the catheter 812 is positioned proximate to the interatrial septum 816, a needle or piercing member (not shown) is advanced through the catheter 812 and used to puncture the fossa ovalis or other portion of the interatrial septum 816. In some embodiments, the catheter 812 may be dimensioned and sized to pass through the fossa ovalis without requiring a puncturing device. That is, the catheter 812 may pass through the natural anatomical structure of the fossa ovalis into the left atrium LA.

Similarly, any chamber (LV, RV, LA, RA) of the heart 800 may be approached through the inferior vena cava 814. For example, the right ventricle RV may be approached through the inferior vena cava 814, into the right atrium RA, and through the tricuspid valve 820. A variety of other endovascular approaches may also be used.

Figure 8B:
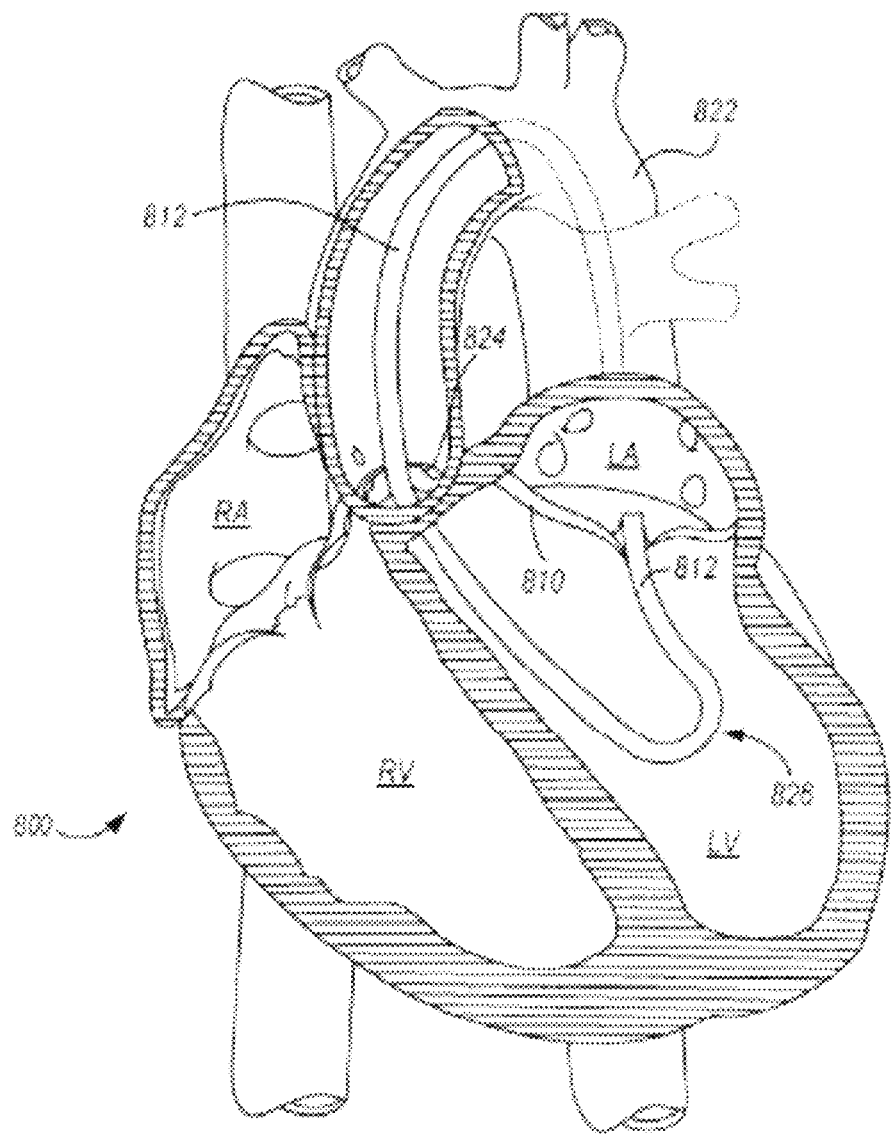
FIG. 8B depicts a schematic diagram of an illustrative retrograde approach of an annuloplasty ring to the mitral valve of a heart according to an embodiment.

FIG. 8B depicts a schematic diagram of an illustrative retrograde approach of an annuloplasty ring (not shown) to the mitral valve 810 of a heart 800 according to another embodiment. In FIG. 8B, a femoral approach is shown wherein the delivery catheter 812 may be advanced through the aorta 822 and the aortic valve 824. Typically, the catheter 812 may be advanced through a sheath positioned within the femoral artery (not shown). Under fluoroscopy or other methods of guidance, the distal end of the catheter 812 may be guided within the left ventricle LV and turned (for example, as shown with a "U-turn" 826) within the left ventricle LV so as to pass through the leaflets of the mitral valve 810 and into the left atrium LA. After verification of the appropriate positioning of the catheter 812, a guide wire (not shown) may be inserted through the catheter 812 into the left atrium LA, which may be used to guide one or more other catheters into the left atrium LA for delivering and anchoring the annuloplasty ring to the annulus of the mitral valve 810.

Figure 8C:
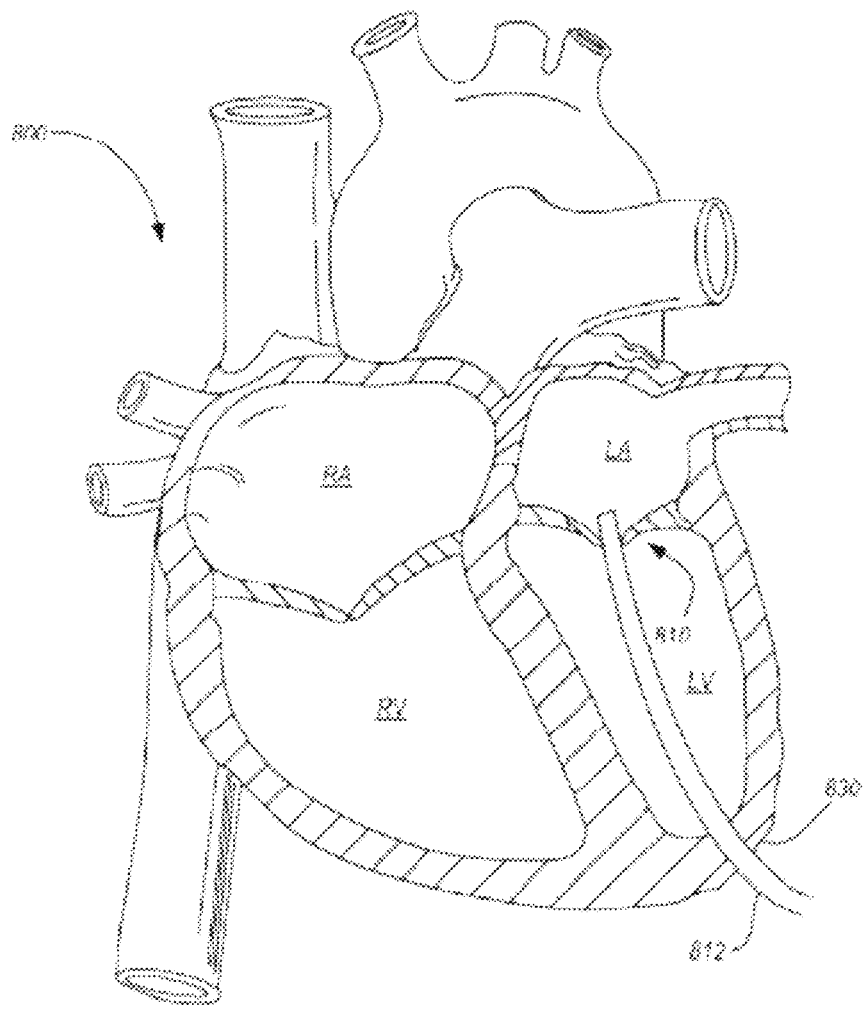
FIG. 8C depicts a schematic diagram of an illustrative trans-apical approach of an annuloplasty ring to the mitral valve of a heart according to an embodiment.

FIG. 8C depicts a schematic diagram of an illustrative trans-apical approach of an annuloplasty ring (not shown) to the mitral valve 810 of a heart 800 according to another embodiment. As shown in FIG. 8C, the catheter 812 may pass through the apex 830 of the heart 800, through the left ventricle LV, through the leaflets of the mitral valve 810, and into the left atrium LA. The annuloplasty ring may be delivered through the catheter 812 into the left atrium LA and anchored to the annulus of the mitral valve 810. In an embodiment, a needle or trocar may be used to puncture through the apex 830 to create a small opening through which a guide wire (not shown) can be inserted through the left ventricle LV into the left atrium LA. The guide wire may be used to guide successively larger and stiffer catheters so as to gradually increase the size of the opening in the apex 830 of the heart 800.

Additionally, an annuloplasty ring may be applied to the mitral valve via a trans-atrial approach, in which a catheter is introduced into the left atrium in a direct approach from the right atrium (not shown).

Figure 9A:
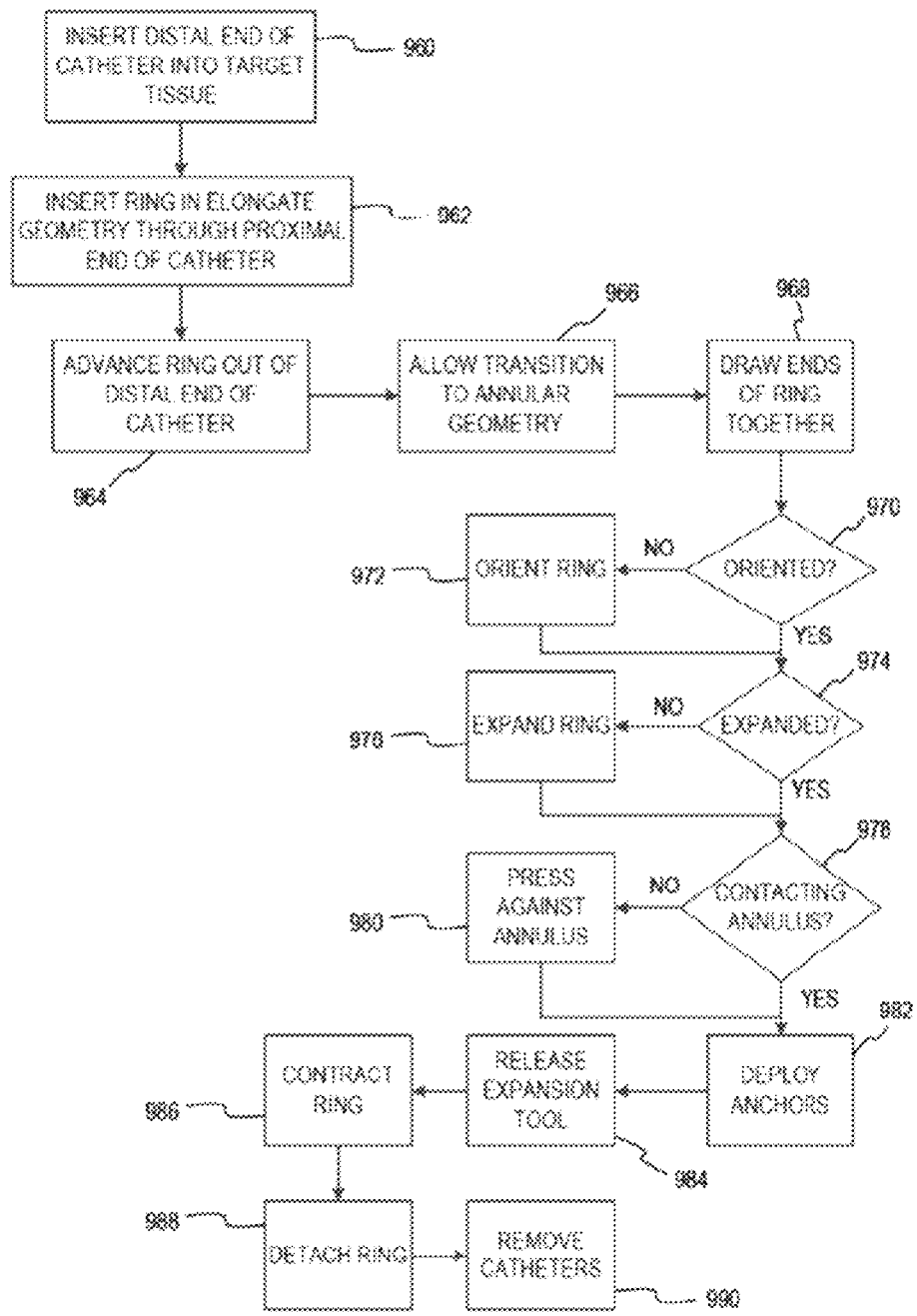
FIG. 9A depicts a flow diagram of a first illustrative method of placing an annuloplasty ring at a target valve according to an embodiment.

FIG. 9A depicts a flow diagram of a first illustrative method of placing an annuloplasty ring at a target valve according to an embodiment. The method may include inserting 960 a distal end of a catheter into a target tissue, such as the heart. The method of insertion 960 is not limited by this disclosure and may be any method, particularly methods described herein with respect to FIGS. 8A-8C. The annuloplasty ring may be inserted 962 in the proximal end of the catheter and advanced 964 through the catheter and out of the distal end such that it is placed at the location of the target tissue. In some embodiments, advancing 964 may include guiding the annuloplasty via the delivery system described herein. When the annuloplasty ring is inserted 962 and advanced 964, it may be in an elongate insertion geometry, as described in greater detail herein. As the ring advances 964 out of the catheter, it may be allowed 966 to transition to an annular operable geometry, as described in greater detail herein. In some embodiments, advancing 964 and/or allowing 966 the annuloplasty ring may include manipulating a ring closure knob located on a deployment handle, as described in greater detail herein.

The ends of the annuloplasty ring may be drawn 968 together, such as, for example, by pulling a first suture connected to the annuloplasty ring through the catheter. In some embodiments, the ends may be drawn 968 together via manipulating a ring closure knob located on a deployment handle, as described in greater detail herein. In some embodiments, a ring closure lock may lock the two ends of the ring together once they have been sufficiently drawn 968 together. In some embodiments, drawing 968 the ends together may further include manipulating a ring snap knob on a deployment handle to cause the ends to snap together, as described in greater detail herein.

In various embodiments, a determination 970 may be made as to whether the ring is sufficiently oriented. In some embodiments, orientation of the ring may be based on the positioning and/or location of the catheter, the location and/or positioning of the target tissue, the shape of the ring, and/or the like. If orientation of the ring is necessary, the ring may be oriented 972. Orienting 972 may include, for example, rotating the ring, the catheter, and/or various other components described herein. In some embodiments, orienting 972 may include automatically rotating the ring to change a plane of the ring from a first orientation that is parallel to the catheter to a second orientation that is parallel to a plane of the annulus. In some embodiments, orienting 972 the annuloplasty ring may be completed via the stabilizer portion, such as by manipulating a stabilizer knob on a deployment handle, as described in greater detail herein.

In various embodiments, a determination 974 may be made as to whether the ring is sufficiently expanded. In some embodiments, expansion of the ring may be based on the construction of the ring, as described in greater detail herein. Thus, in some embodiments, expansion may not occur, particularly in embodiments where the ring is not expandable, as described in greater detail herein. If expansion of the ring is necessary, the ring may be expanded 976. Expansion of the ring may be completed by manipulating one or more sutures, as described in greater detail herein. In some embodiments, expanding 976 the ring may be completed via an expansion tool, such as, for example, by manipulating an expansion tool knob on a deployment handle, as described in greater detail herein. In some embodiments, a percutaneously, transcatheter-operated expansion tool may be actuated to expand 976 the annuloplasty ring in the annular operable geometry to an expanded state to thereby increase an A-P distance of the annuloplasty ring. Expanding 976 the annuloplasty ring may include expanding a biasing element of the annuloplasty ring.

In various embodiments, a determination 978 may be made as to whether the ring is contacting the annulus. The determination 978 may be necessary, for example, to ensure proper placement of the ring adjacent to the annulus. In some embodiments, the ring may be pressed 980 against the annulus. Pressing 980 may include positioning the annuloplasty ring in abutment or similar relatively intimate contact with an annulus of a target valve to enhance a process of fastening the annuloplasty ring to the annulus. The method may include manipulating a stabilizer, such as via a stabilizer knob, as described in greater detail herein. The method may also include pulling a second suture connected to the annuloplasty ring through the catheter to deploy 982 a plurality of tissue anchors from the annuloplasty ring. Deployment 982 of the anchors may also be completed via manipulation of an anchor deployment knob, as described in greater detail herein. With the anchors deployed 982 and the annuloplasty ring fastened to the tissue of the target valve, the expansion tool may be released 984. The annuloplasty ring may be contracted 986 to transition the annuloplasty ring in the operable geometry to a contracted state to decrease the A-P distance, thereby decreasing the A-P distance of the target heart valve to improve coaptation and reduce regurgitation through the target heart valve. In some embodiments, contraction 986 of the annuloplasty ring may be completed by biasing elements that have stored potential energy during expansion of the annuloplasty ring.

In various embodiments, the annuloplasty ring may be detached 988 from the catheter and the first and second sutures, and the catheter may be removed 990 from the heart. In some embodiments, the ring may be detached 988 via manipulation of a ring release knob on a deployment handle, as described in greater detail herein.

Figure 9B:
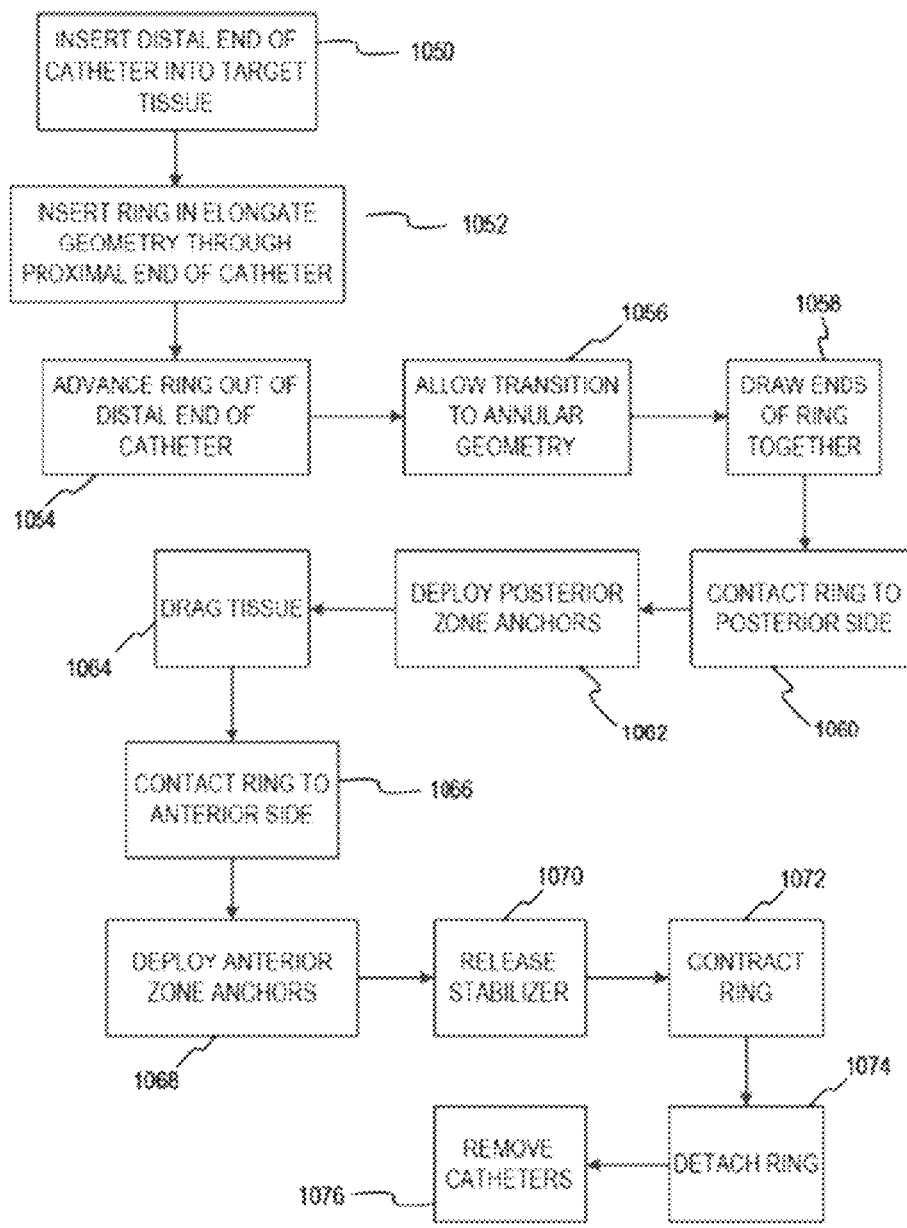
FIG. 9B depicts a flow diagram of a second illustrative method of placing an annuloplasty ring at a target valve according to an embodiment.

FIG. 9B depicts a flow diagram of a second illustrative method of placing an annuloplasty ring at a target valve according to an embodiment. The method may include inserting 1050 a distal end of a catheter into a target tissue, such as the heart. The method of insertion 1050 is not limited by this disclosure and may be any method, particularly methods described herein with respect to FIGS. 8A-8C. The annuloplasty ring may be inserted 1052 in the proximal end of the catheter and advanced 1054 through the catheter and out of the distal end such that it is placed at the location of the target tissue. In some embodiments, advancing 1054 may include guiding the annuloplasty via the delivery system described herein. When the annuloplasty ring is inserted 1052 and advanced 1054, it may be in an elongate insertion geometry, as described in greater detail herein. In some embodiments, the annuloplasty ring may be attached to a catheter. As the ring advances 1054 out of the catheter, it may be allowed 1056 to transition to an annular operable geometry, as described in greater detail herein. In some embodiments, advancing 1054 and/or allowing 1056 the annuloplasty ring may include manipulating a ring closure knob located on a deployment handle, as described in greater detail herein.

The ends of the annuloplasty ring may be drawn 1058 together, such as, for example, by pulling a first suture connected to the annuloplasty ring through the catheter. In some embodiments, the ends may be drawn 1058 together via manipulating a ring closure knob located on a deployment handle, as described in greater detail herein. In some embodiments, a ring closure lock may lock the two ends of the ring together once they have been sufficiently drawn 1058 together. In some embodiments, drawing 1058 the ends together may further include manipulating a ring snap knob on a deployment handle to cause the ends to snap together, as described in greater detail herein.

The annuloplasty ring may be contacted 1060 with a posterior side of the valve. Such contacting 1060 may generally be completed via the delivery system, as described in greater detail herein. Use of the delivery system may include manipulating at the stabilizer, as described in greater detail herein. A first portion of the anchors may be deployed 1062, such as, for example, the posterior zone anchors (as described herein). Thus, in some embodiments, anchors located in two posterior zones may be deployed sequentially. Alternatively, anchors located in two posterior zones may be deployed simultaneously. Deployment 1062 may effect engagement of the one or more posterior zones of the annuloplasty ring (or a portion thereof) to the posterior side of the valve. As previously described herein, deployment 1062 may be completed via manipulation of an anchor deployment knob.

The valve tissue may be dragged 1064, via the delivery system, such that the annuloplasty ring may be contacted 1066 to the anterior side of the valve. Use of the delivery system may include manipulating at least the stabilizer, as described in greater detail herein. A second portion of the anchors may be deployed 1068, such as, for example, the anterior zone anchors (as described herein). Thus, in some embodiments, anchors located in two anterior zones may be deployed sequentially. Alternatively, anchors located in two anterior zones may be deployed simultaneously. Deployment 1068 may effect engagement of the anterior zone of the annuloplasty ring (or a portion thereof) to the anterior side of the valve.

With the anchors deployed 1062, 1068 and the annuloplasty ring fastened to the tissue of the target valve, the stabilizer may be released 1070. The annuloplasty ring may be contracted 1072 to transition the annuloplasty ring in the operable geometry to a contracted state to decrease the A-P distance, thereby decreasing the A-P distance of the target heart valve to improve coaptation and reduce regurgitation through the target heart valve. In some embodiments, contraction 1072 of the annuloplasty ring may be completed by biasing elements that have stored potential energy during expansion of the annuloplasty ring.

In various embodiments, the annuloplasty ring may be detached 1074 from the catheter and the first and second sutures, and the catheter may be removed 1076 from the heart. In some embodiments, the ring may be detached 1074 via manipulation of a ring release knob on a deployment handle, as described in greater detail herein.

Figure 9C:
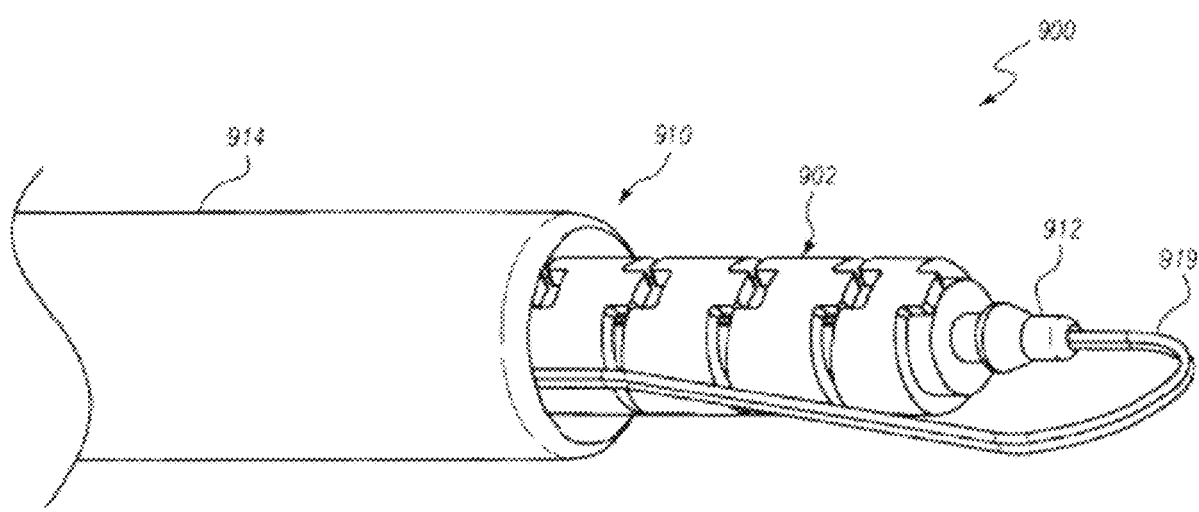
FIGS. 9C, 9D, 9E, and 9F depict schematic diagrams of transcatheter delivery of an annuloplasty ring from a delivery system according to various embodiments.

FIGS. 9C, 9D, 9E, and 9F depict schematic diagrams illustrating transcatheter delivery of an annuloplasty ring 902 from a delivery system 900 according to various embodiments. FIG. 9C depicts a perspective view of a distal end 910 of the delivery system 900. As shown in FIG. 9C, the annuloplasty ring 902 may be in the elongate insertion geometry and partially deployed from the distal end 910 of a delivery catheter 914 in a first deployment stage. In the first stage, the annuloplasty ring 902 may still be substantially in the elongate insertion geometry. As shown in FIG. 9C, a first suture 919 for snapping together the ends of the annuloplasty ring 902 may pass through a male snap 912 of a ring closure lock 950 (shown in FIG. 9E).

Figure 9D:
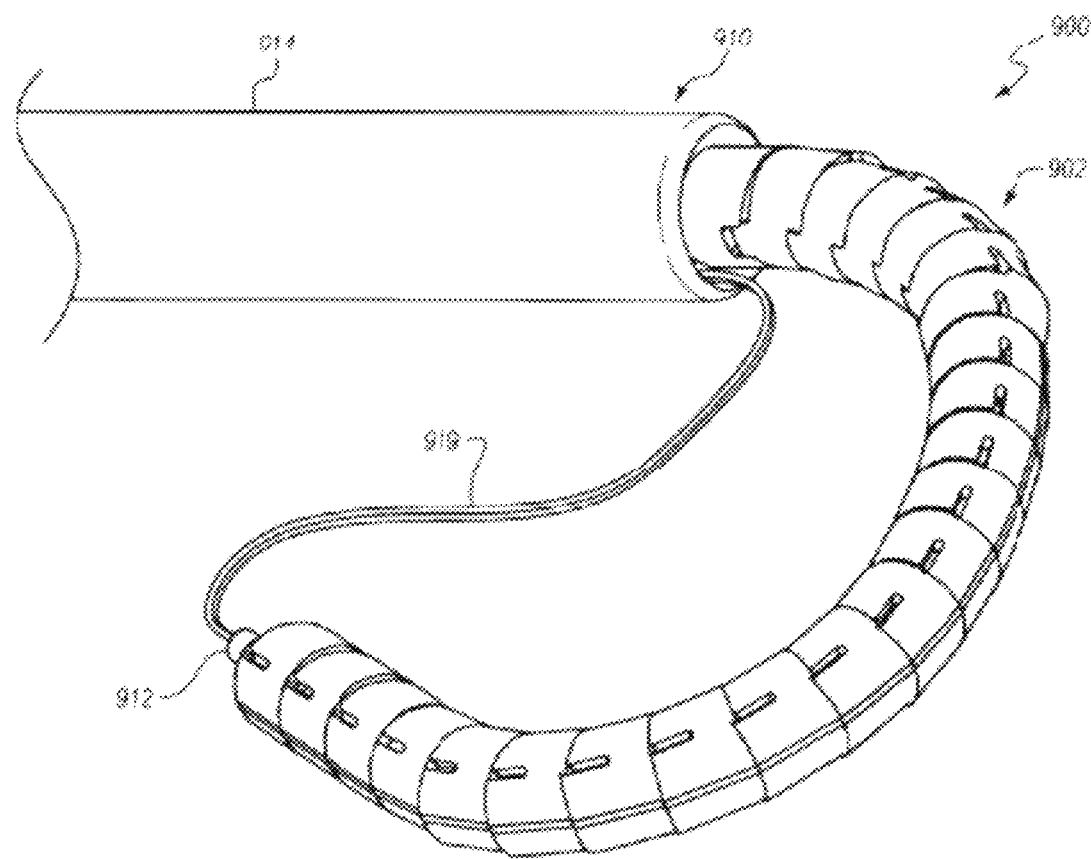

FIG. 9D is a perspective view of the annuloplasty ring 902 in a second stage of partial deployment from the delivery catheter 914. In the second stage, the portion of the annuloplasty ring 902 that has exited the delivery catheter 914 has begun to transition (due to the shape memory materials used in the annuloplasty ring) from the elongate insertion geometry to the annular operable geometry.

Figure 9E:
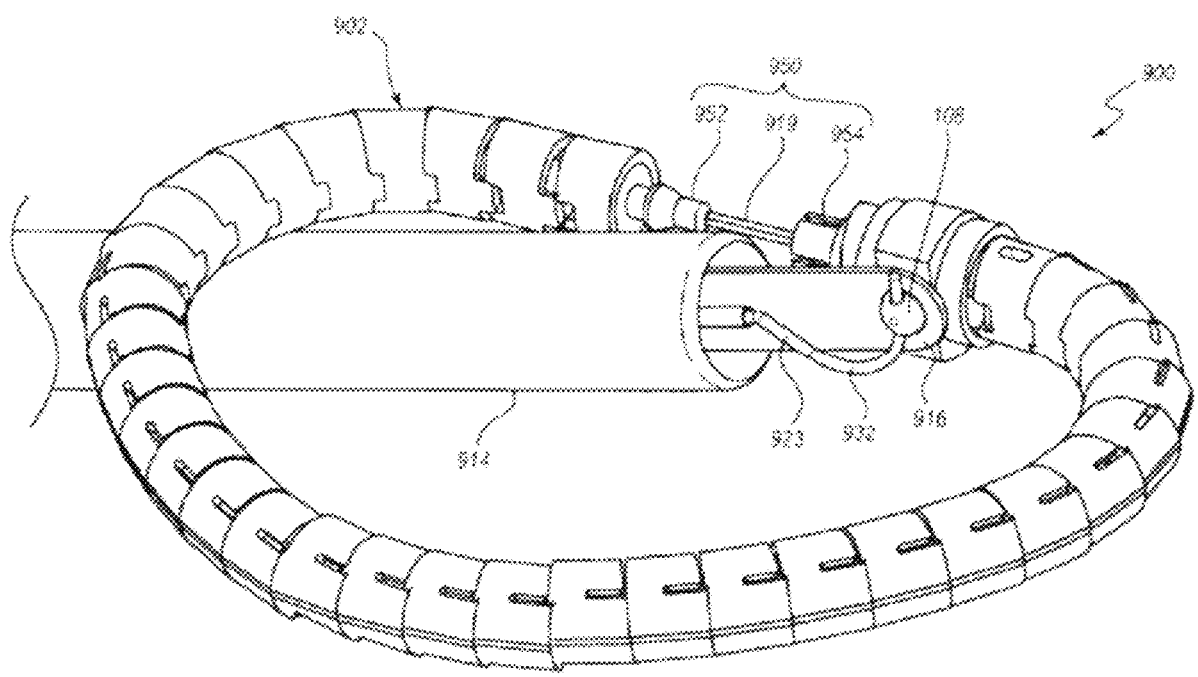

FIG. 9E is a perspective view of the annuloplasty ring 902 in a third stage of deployment in which a ring shuttle 916 of the delivery system 900 has substantially pushed the annuloplasty ring out of the delivery catheter 914, but the plane of the annuloplasty ring is still aligned with (for example, parallel to) the longitudinal axis of the delivery catheter. In FIG. 9E, the annuloplasty ring 902 may be in a configuration, for example, immediately before a ring deployment wire 923 cooperates with the pivot 108 to rotate the annuloplasty ring 902 (see FIG. 9F). In the configuration shown in FIG. 9E, the distal end of the ring deployment wire 923 may include a bend or hook 932 as it passes through a hole in the pivot 108. The ring deployment wire 923 includes a superelastic shape memory material (such as, for example, nitinol), and bending the distal end of the ring deployment wire 923 into the hook 932 shape may spring load the annuloplasty ring 902 within the outer jacket delivery catheter 914 such that the annuloplasty ring 902 automatically rotates about the pivot 108 upon exiting the outer jacket delivery catheter 914. At this third stage of deployment, the hook 932 shape formed in the superelastic ring deployment wire 923 is ready to unload (return to a heat-set memorized straight configuration) as soon as the delivery catheter 914 no longer prevents it from doing so. The suture 919 may be used to draw together the male components 952 and female components 954 of a ring closure lock 950.

Figure 9F:
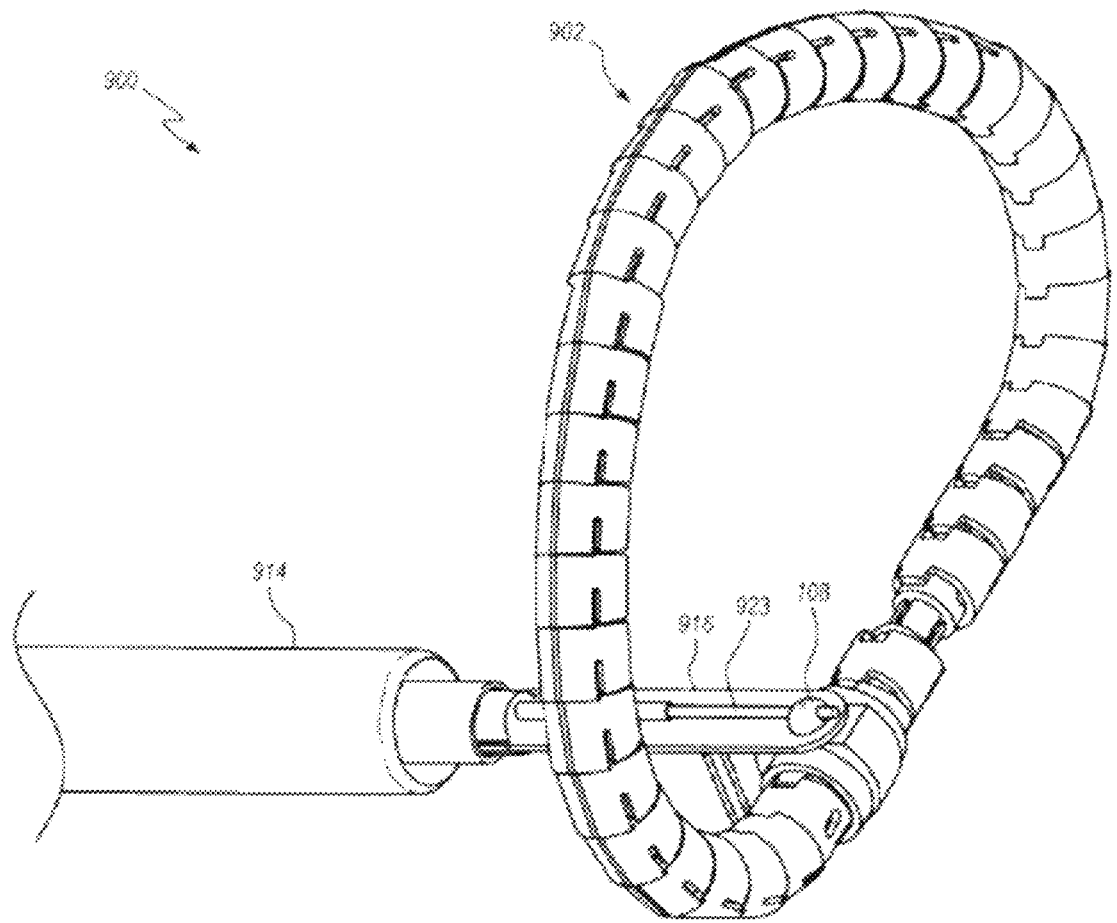

FIG. 9F depicts a perspective view of the annuloplasty ring 902 in a fourth stage of deployment in which the plane of the annuloplasty ring (in its annular operable geometry) has been changed to be perpendicular to the longitudinal axis of the delivery catheter 914. As shown in FIG. 9F, the superelastic ring deployment wire 923 has returned to its heat set (memorized) straight configuration. At this fourth stage of deployment, the plane of the annuloplasty ring 902 may be configured to be parallel to the plane of the heart valve annulus. In situ within the heart, a longitudinal axis of the delivery catheter 914 may be oriented parallel to the direction of blood through the valve and approximately perpendicular to the plane of the heart valve. The annuloplasty ring 902, when oriented such that the plane of the annuloplasty ring is transverse to (and perpendicular or approximately perpendicular to) the longitudinal axis of the delivery catheter 914, may be oriented such that the plane of the annuloplasty ring is parallel or approximately parallel to the plane of the heart valve.

In further stages of deployment, the annuloplasty ring 902 may be expanded and/or pressed against the heart valve annulus before deploying the anchors (such as the curved anchors 104 shown in FIGS. 1A and 1B). As discussed herein, certain anchors may propel themselves into the tissue of the heart valve annulus upon being deployed. In other embodiments, the anchors (such as the linear anchors 710 shown in FIG. 7) may be deployed before pressing the annuloplasty ring 902 against the annulus. After the annuloplasty ring 902 is anchored to the heart valve annulus and transitioned to the contracted state, the ring deployment wire 923 may be pulled from the hole in the pivot 108 to release the annuloplasty ring 902 from the ring shuttle 916. Any remaining sutures, such as the first suture 919, may also be cut and/or pulled from the annuloplasty ring 902 before the delivery catheter 914 is removed from the heart. In some embodiments, removal of the ring deployment wire 923 and/or any remaining sutures may be completed via one or more of the knobs, as described in greater detail herein.

Figure 10:
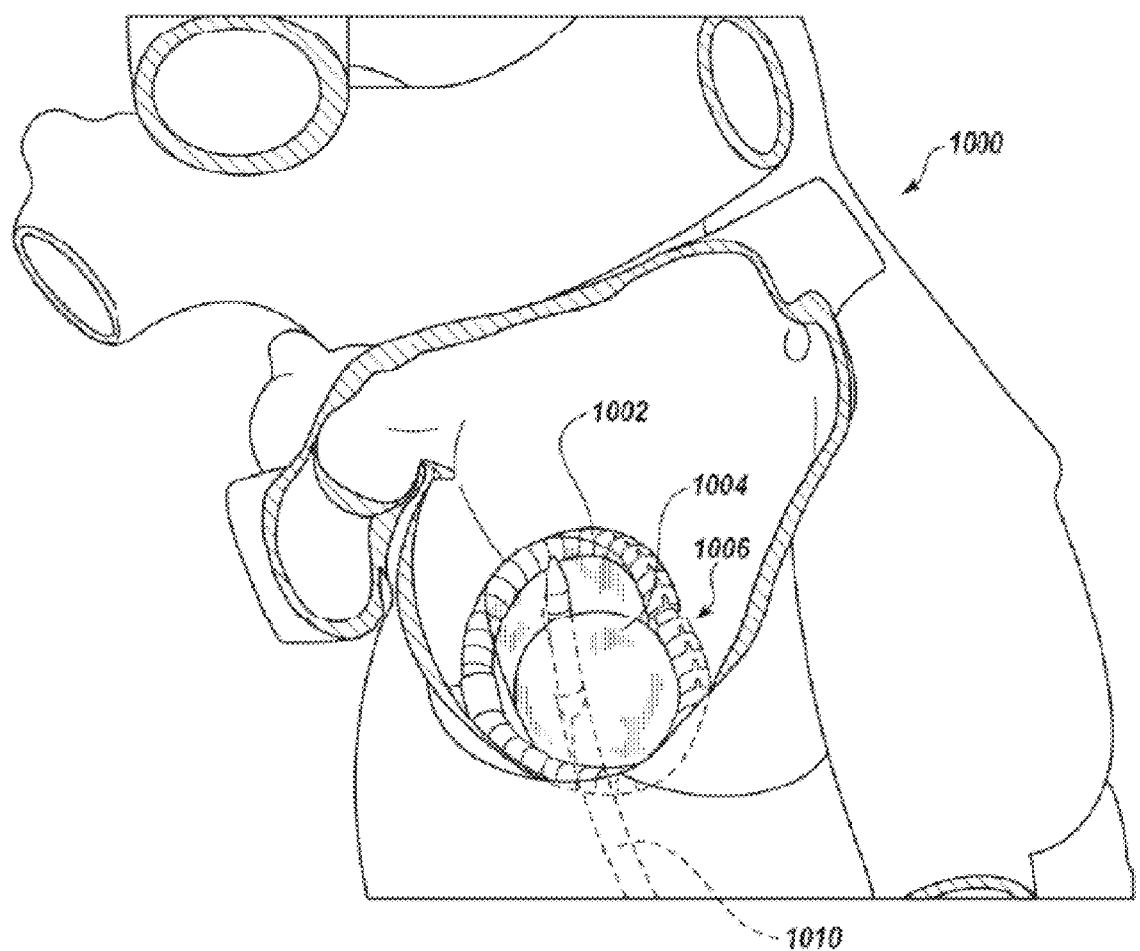
FIG. 10 depicts a schematic diagram of a perspective, partial cross-sectional view of a heart during an expansion of an adjustable annuloplasty ring using a balloon expansion tool, preparatory to affixation to the annulus of the mitral valve according to an embodiment.

FIG. 10 depicts a schematic diagram of a perspective, partial cross-sectional view of a heart 1000 during the expansion of an adjustable annuloplasty ring 1002 using an expansion tool 1004, preparatory to affixation to the annulus of the mitral valve 1006 according to an embodiment. As shown in FIG. 10, a delivery catheter 1010 may extend from the left ventricle into the left atrium through the leaflets of the mitral valve 1006. Thus, this illustrated embodiment may correspond to, for example, a trans-apical approach or a retrograde approach, as discussed herein. Those with ordinary skill in the art will recognize from the present disclosure that similar principles as those illustrated may be used for trans-septal approaches.

In FIG. 10, an expansion tool 1004 may be used to expand the annuloplasty ring 1002. The annuloplasty ring 1002 may be positioned on or next to the annulus of the mitral valve 1006. The expansion tool 1004 may be disposed within the annuloplasty ring 1002 (and within the target valve 1006) to expand the annuloplasty ring 1002 to transition it from a contracted state to an expanded state. The expansion tool 1004 of the illustrated embodiment of FIG. 10 is a balloon expansion tool 1004. The balloon expansion tool 1004 may be inflated to expand the annuloplasty ring 1002 to an expanded state. In some embodiments, the balloon expansion tool 1004 may include a plurality of sections and may be considered a "multi-chamber" balloon with a plurality of chambers. In particular embodiments, the balloon expansion tool 1004 may have two chambers. In other embodiments, a balloon expansion tool 1004 may have a single chamber.

In the embodiment shown in FIG. 10, the inflated balloon expansion tool 1004 may reduce or prevent the flow of blood through the mitral valve during at least part of the implantation procedure. In such embodiments, inflation of the balloon expansion tool 1004 may last 20 seconds or less to prevent adverse consequences of occluding the mitral valve 1006. In other embodiments, such as the embodiment of an expansion tool shown in FIGS. 11, 12A-12E, 13A-13D, and 14A-14B, blood may be allowed to flow through the target valve 1006 during the entire procedure.

Figure 11:
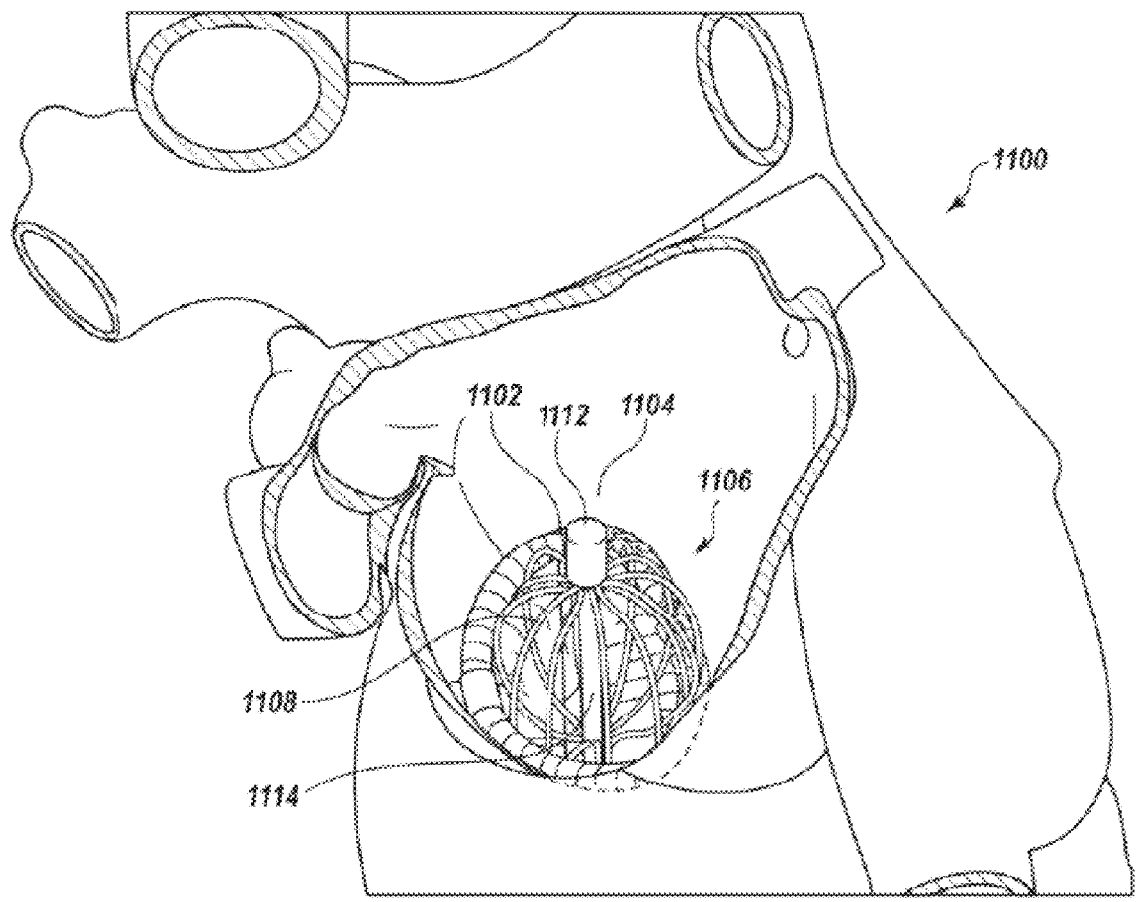
FIG. 11 depicts a schematic diagram of a perspective, partial cross-sectional view of the heart during an expansion of an adjustable annuloplasty ring using a cage or basket expansion tool, preparatory to affixation to the annulus of the mitral valve according to an embodiment.

FIG. 11 depicts a schematic diagram of a perspective, partial cross-sectional view of a heart 1100 during the expansion of an adjustable annuloplasty ring 1102 using a cage or basket tool 1104 as an expansion tool, preparatory to affixation to the annulus of the mitral valve 1106 according to another embodiment.

The basket expansion tool 1104 may include a plurality of flexible members 1108 that lay flat against a central rod 1114 during insertion of the basket expansion tool through the delivery catheter (see FIG. 10) and may be forced into an expanded configuration (shown in FIG. 11) when the central rod is pushed into an end cap 1112. In another embodiment, each of the plurality of flexible members 1108 may include a superelastic material so as to spring from a delivery catheter into the expanded configuration shown in FIG. 11.

Figure 12A:
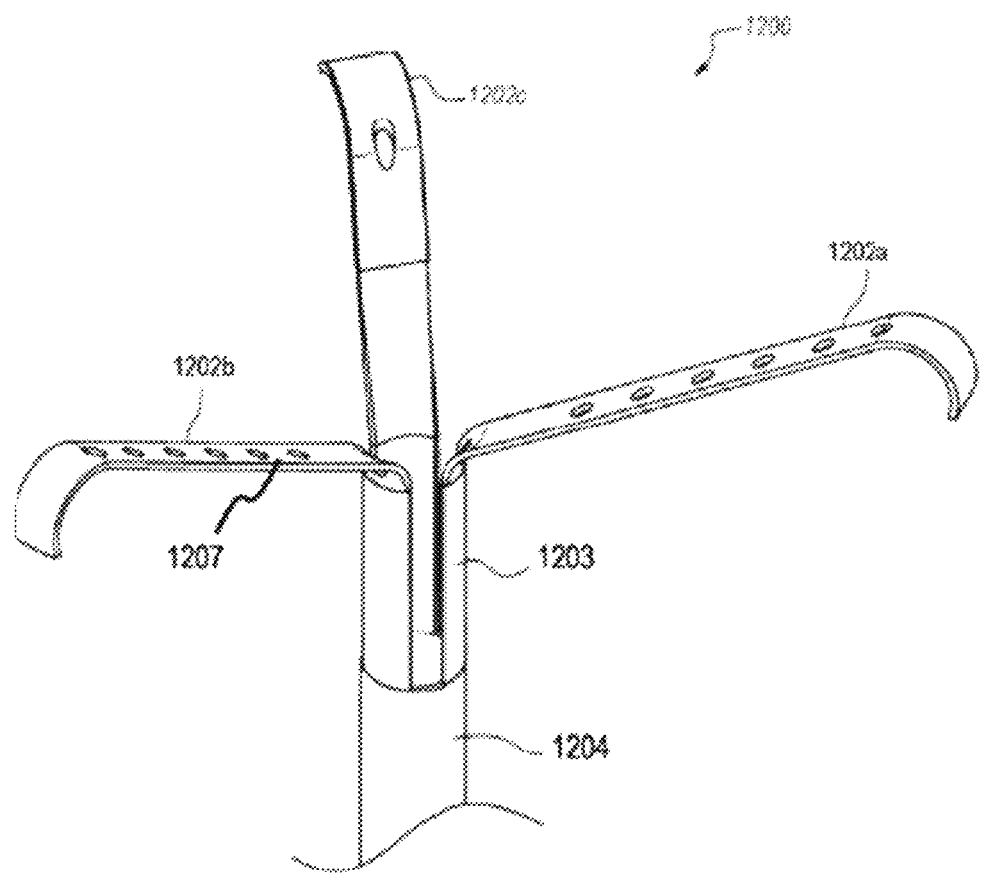
FIGS. 12A and 12B depict perspective views of a stabilizer of a percutaneous annuloplasty system according to an embodiment.
Figure 12B:
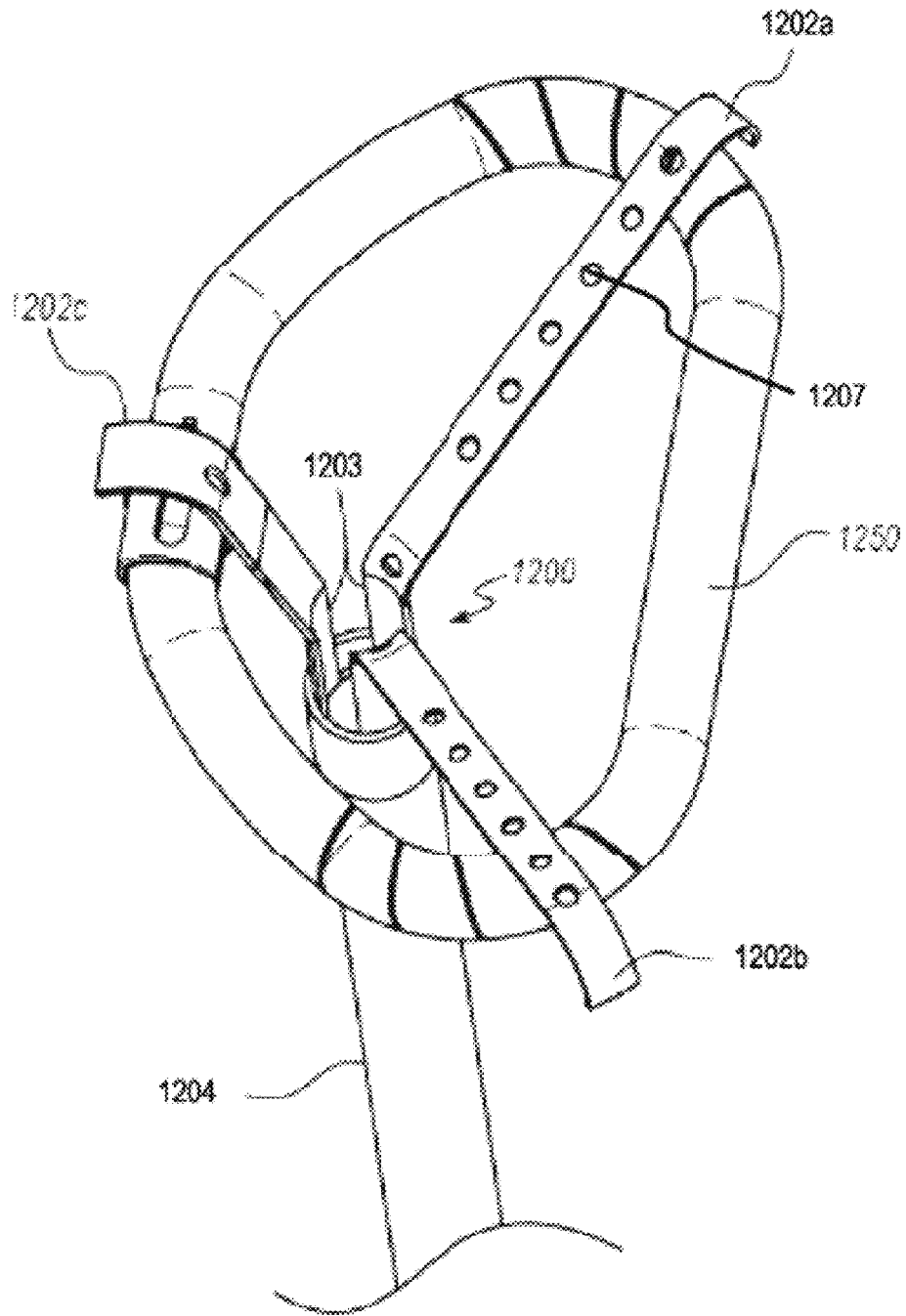

FIGS. 12A and 12B depict schematic diagrams of perspective views of an illustrative stabilizer, generally designated 1200, that may be used in lieu of the expansion tool according to an embodiment. FIG. 12A depicts a perspective view of the stabilizer 1200 separated from other components of the percutaneous annuloplasty system. FIG. 12B depicts the stabilizer 1200 disposed through a delivery catheter 1204 and engaging an annuloplasty ring 1250.

In order to achieve sufficient intimate contact between an annuloplasty ring 1250 (shown in FIG. 12B) and the tissue of the target heart valve (for example, the annulus of the heart valve), the stabilizer 1200 may be used to position, orient, and otherwise manipulate the annuloplasty ring 1250 in the annular operable geometry prior to affixation to tissue of the valve. The stabilizer 1200 may have a metallic rib structure having a plurality of arms 1202a, 1202b, 1202c (collectively 1202) or prongs configured to extend outward at an angle from a central column 1203. While only three arms 1202 are shown in the present embodiment, those having ordinary skill in the art will recognize any number of arms may be suitable without departing from the scope of the present disclosure. For example, the stabilizer 1200 may have 2, 3, 4, 5, 6, 7, 8, 9, 10 or more arms 1202. The rib structure, specifically the arms 1202 and central column 1203, may be laser cut from a shape memory material, such as nitinol. The stabilizer 1200 may be cut from a hollow tube such that the central column 1203 has a hollow cylindrical shape. The arms 1202 may be heat set to extend at an angle from the central column 1203.

The illustrated stabilizer 1200 of FIGS. 12A and 12B may include three arms 1202 arranged, for example, as a tripod. The plurality of arms 1202 of the stabilizer 1200 may be loaded into a delivery catheter 1204 together with the annuloplasty ring 1250 (for example, configured in the elongate insertion geometry). As the arms 1202 emerge from a distal end of the delivery catheter 1204, they may automatically expand outward. The stabilizer 1200, and specifically the plurality of arms 1202, may be configured to align with and engage the annuloplasty ring 1250 as shown in FIG. 12B. When aligned and engaged with the annuloplasty ring 1250, the stabilizer 1200 may be used to push/pull the annuloplasty ring 1250 toward the tissue of an annulus of a heart valve.

The illustrated stabilizer of FIGS. 12A and 12B may be configured to engage a top surface of the annuloplasty ring 1250, through the annuloplasty ring, to pull the annuloplasty ring downward. For example, the plurality of arms 1202 may include a curved, angled, or hooked portion at a distal end to facilitate engagement with the annuloplasty ring 1250. The stabilizer 1200 may be used to pull the annuloplasty ring 1250 toward the heart valve to facilitate intimate contact of the annuloplasty ring with the annulus. Intimate contact, or close abutment, of the annuloplasty ring 1250 with the annulus of the valve may enhance an anchor deployment process to fasten the annuloplasty ring 1250 to the annulus.

In some embodiments, the stabilizer 1200, particularly the arms 1202, may also be configured to function as an expansion tool to engage the annuloplasty ring 1250 and effectuate and/or facilitate transition of the annuloplasty ring from a contracted state to an expanded state. For example, a superelastic property and memorized shape of the plurality of arms 1202 may effectuate expansion of the annuloplasty ring 1250. The superelastic arms 1202 may engage an inner surface of the annuloplasty ring 1250 and exert outward force to expand the annuloplasty ring. In other embodiments, a suture or other elongate member may enable percutaneous manipulation of one or more of the plurality of arms to effectuate expansion of the annuloplasty ring 1250.

Figure 12C:
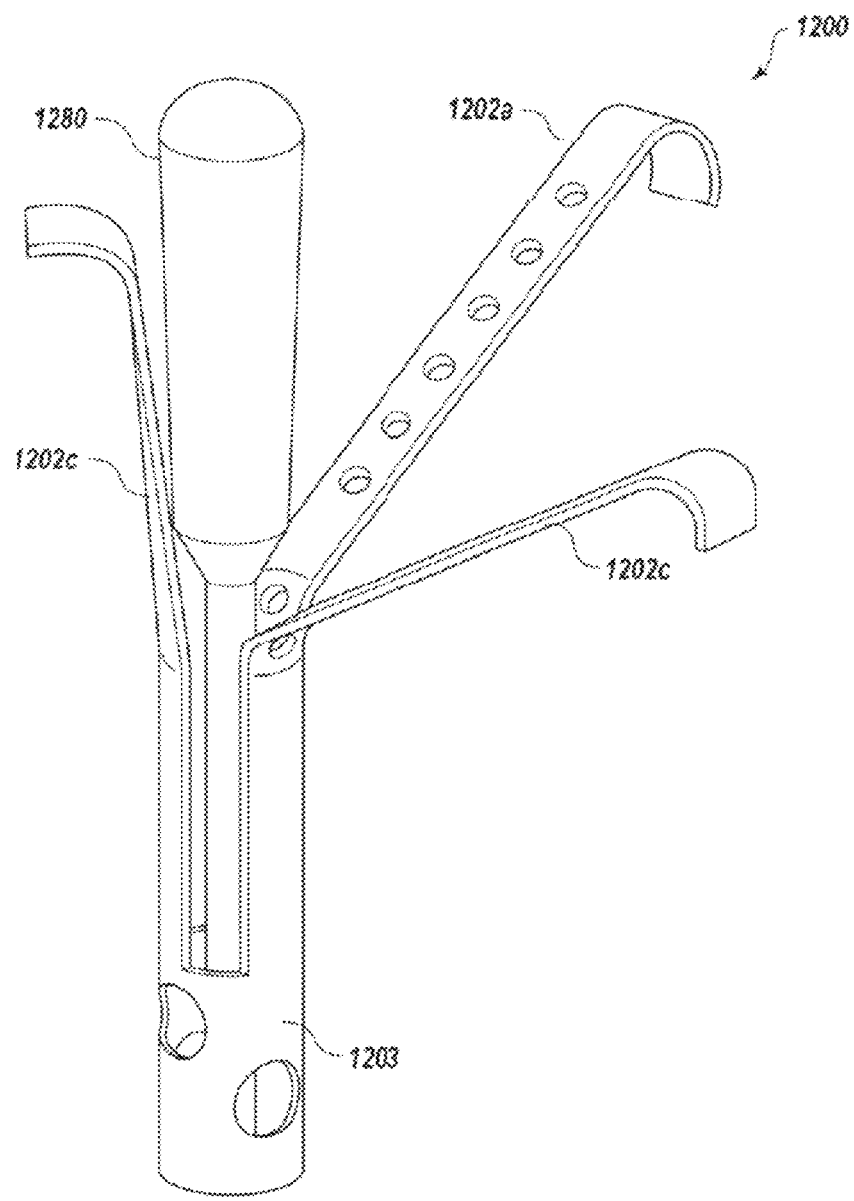
FIGS. 12C and 12D depict a stabilizer including a balloon, according to an embodiment.
Figure 12D:
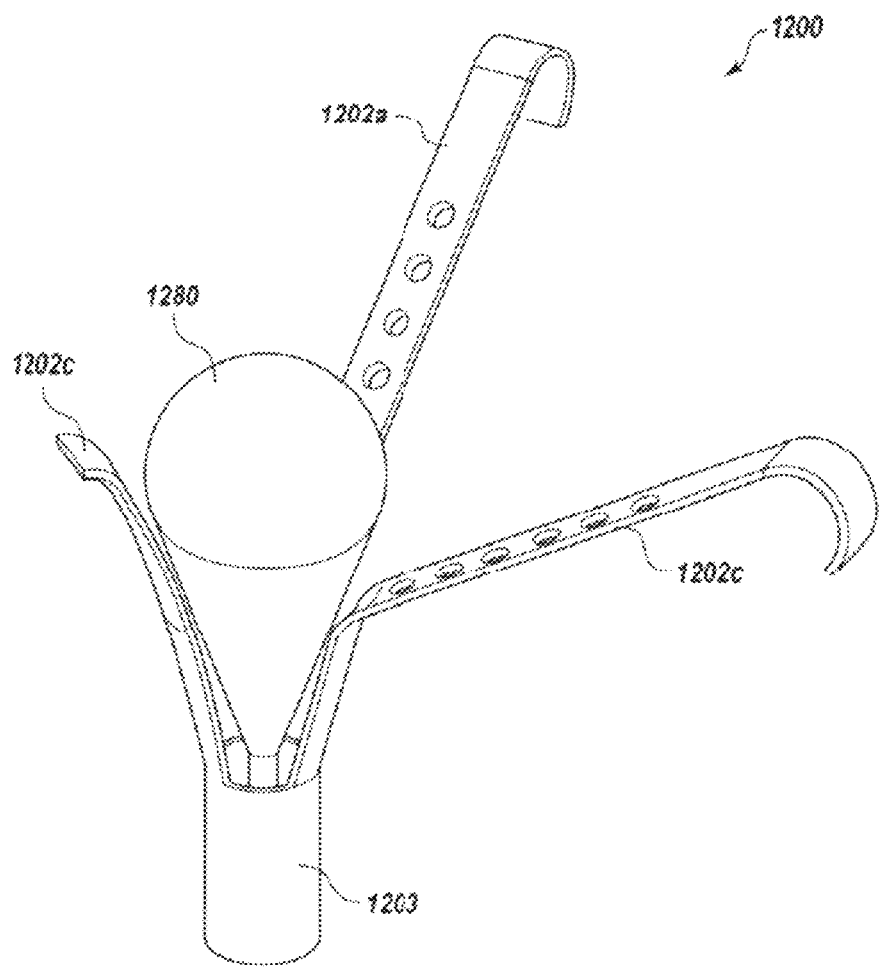

FIGS. 12C and 12D depict a stabilizer 1200 that includes a balloon 1280. The balloon 1280 may pass through the central column 1203 of the stabilizer 1200. When the balloon 1280 is inflated, it may cause the arms 1202 of the stabilizer 1200 to expand. By expanding the stabilizer 1200, the ring 1250 (FIG. 12E) may be expanded to its expanded configuration. In some embodiments, the ring 1250 (FIG. 12E) may also be contracted when the balloon 1280 is deflated and the tool 1200 is retracted.

Figure 12E:
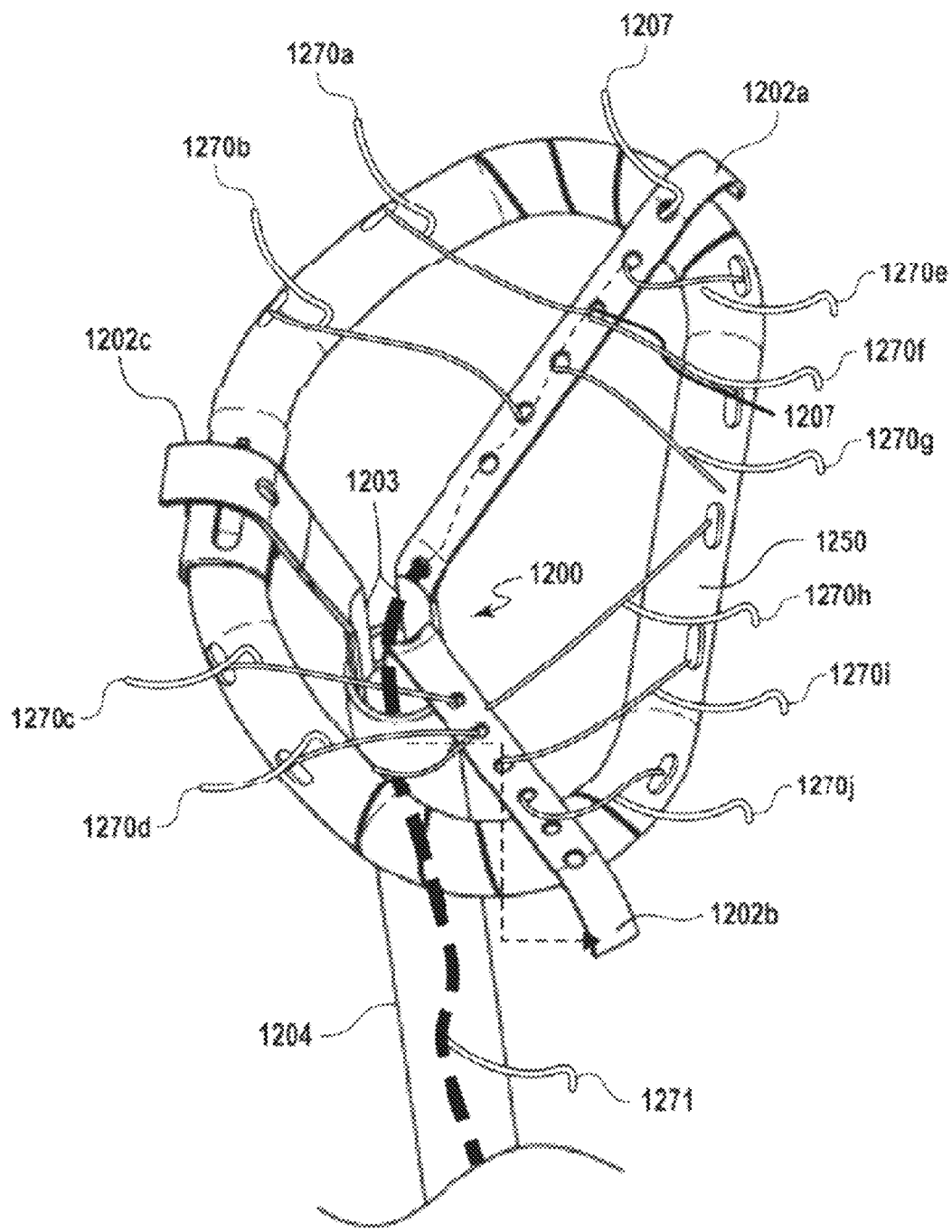
FIG. 12E depicts a schematic diagram that demonstrates how holes in the arms of a stabilizer may be used to help guide sutures that are exiting the ring according to an embodiment.

FIG. 12E depicts a schematic diagram that demonstrates how various holes 1270 may be used to guide one or more sutures 1271 that exit the ring 1250, as described in greater detail herein. The sutures 1271 may be used for deployment or recapturing of the anchors held within the ring 1250. In some embodiments, the sutures 1271 may extend through the windows in the ring and/or dedicated holes in the laser cut pattern of the ring, as described herein. The holes in the tool 1200 may allow the sutures 1271 to be gathered together and guided through the hollow central column 1203 and the catheter 1204 via the handle at the proximal end of the catheter, as described in greater detail herein.

In various embodiments, the expansion tool and/or the stabilizer may be configured to complete one or more additional tasks. Illustrative additional tasks are not limited by this disclosure, and may include, for example, navigating the annuloplasty ring within a chamber of a heart, creating an intimate contact between the annuloplasty ring and the target tissue (such as a valve annulus), expanding the annuloplasty ring, and stabilizing the annuloplasty ring during various deployment and anchoring processes, as described in greater detail herein.

Figure 13A:
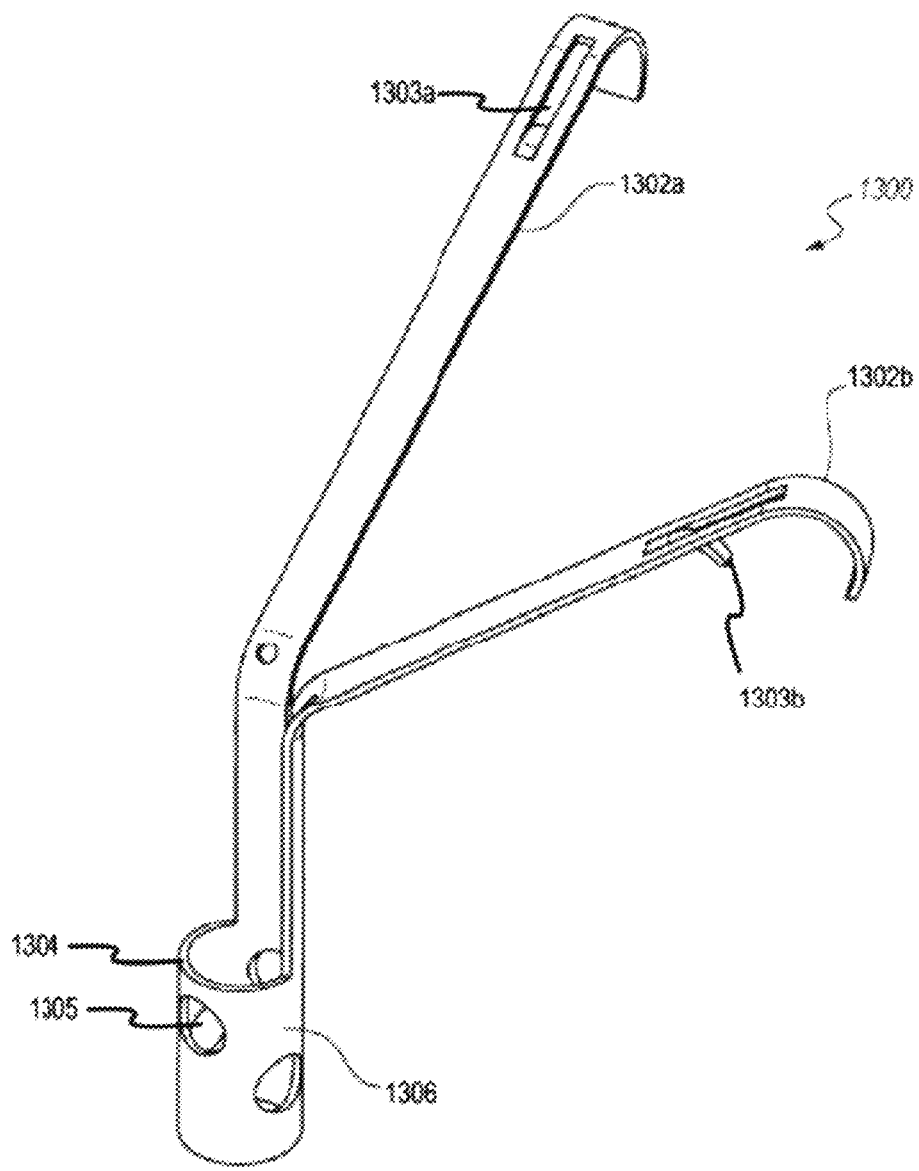
FIGS. 13A, 13B, 13C, and 13D depict perspective views of a stabilizer of a percutaneous annuloplasty system according to an embodiment.
Figure 13B:
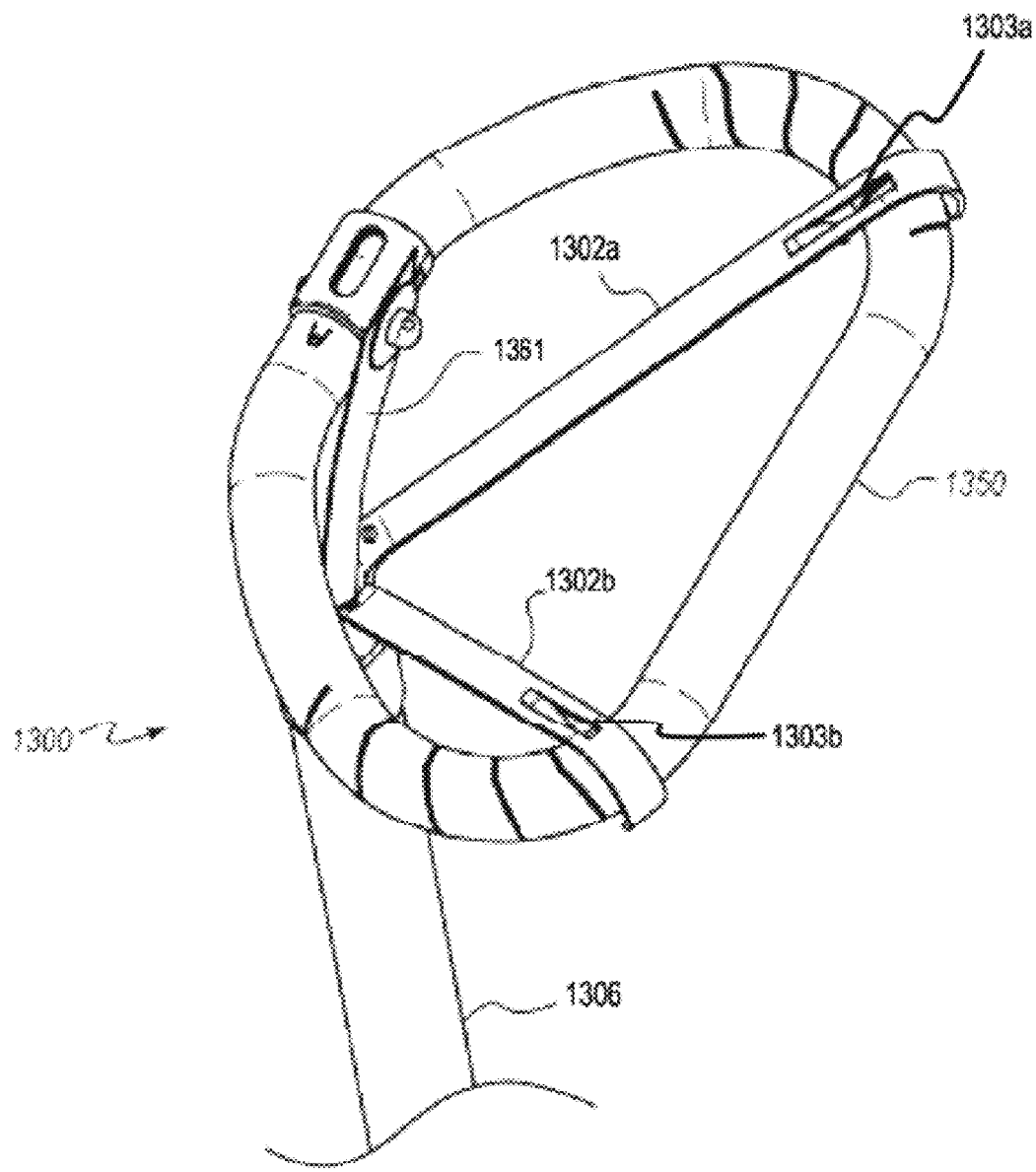
Figure 13C:
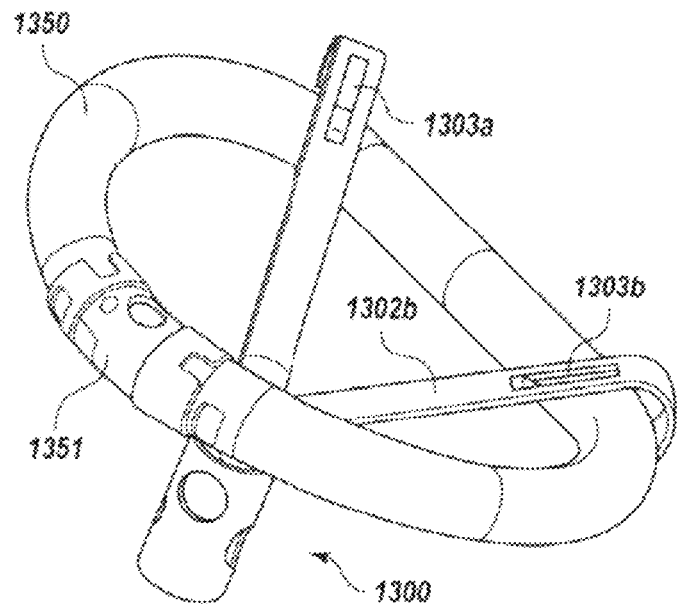
Figure 13D:
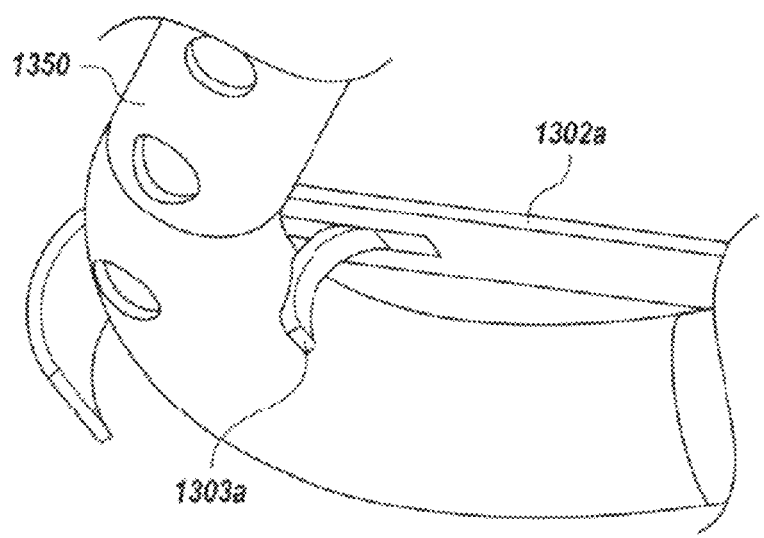
Figure 13E:
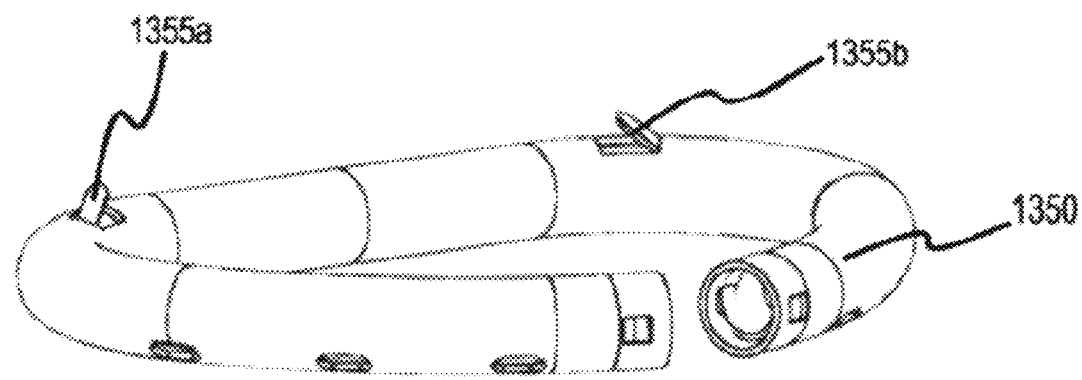
FIGS. 13E-13G depict a perspective view, a side view, and a top view, respectively, of an illustrative annuloplasty ring having strats according to an embodiment.
Figure 13F:
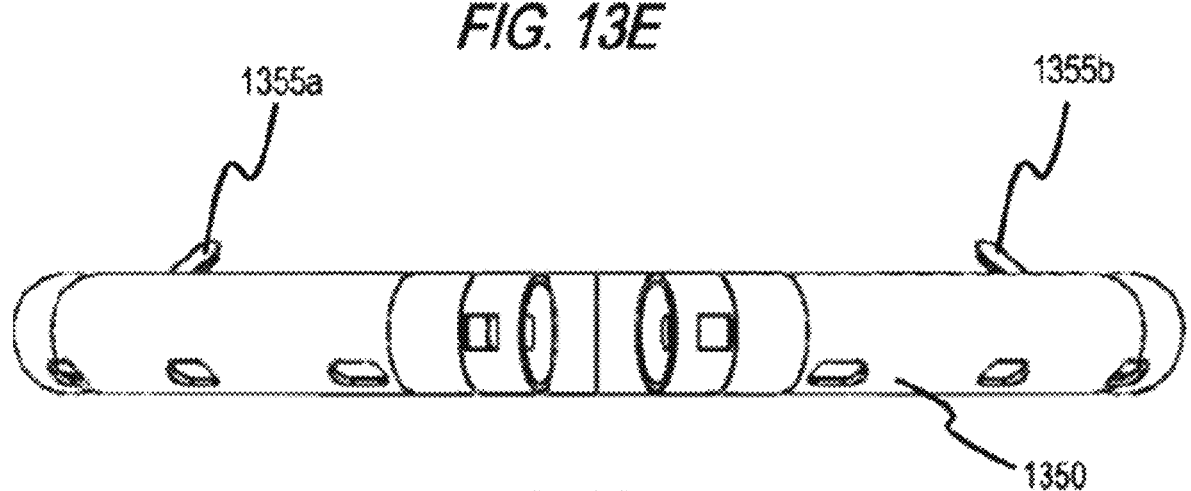
Figure 13G:
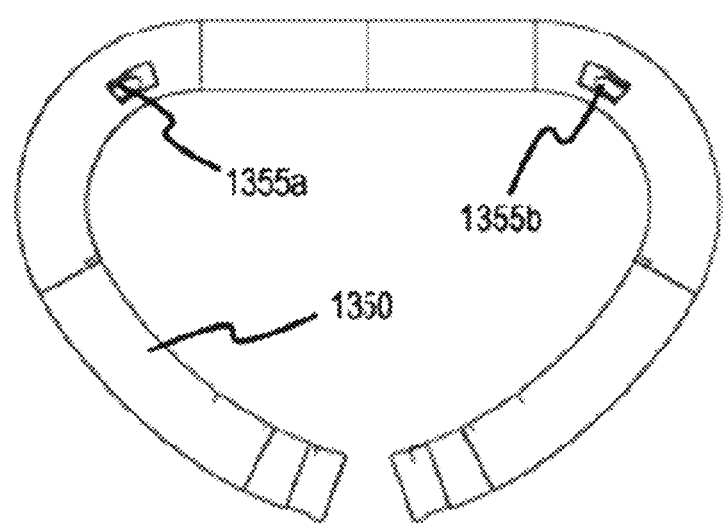
Figure 13H:
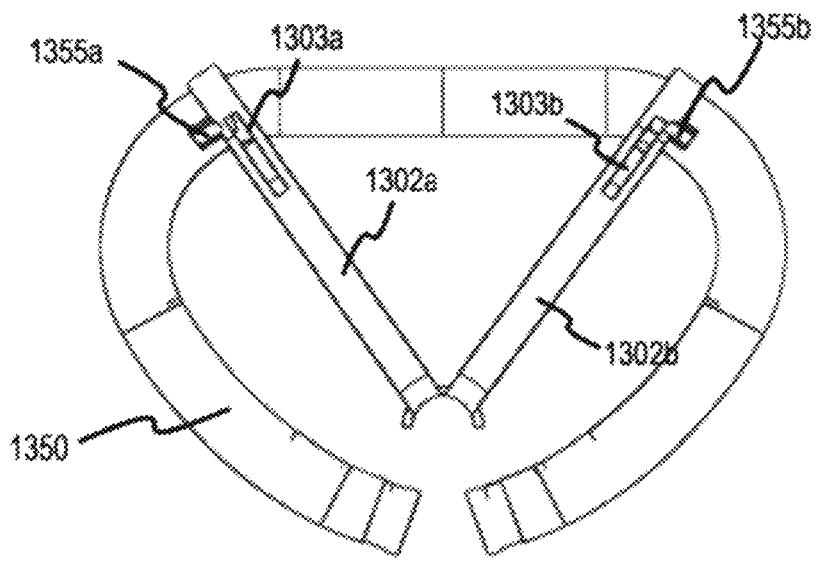
FIGS. 13H and 13I depict a top view and a detailed view, respectively, of an engagement of an annuloplasty ring having strats with a stabilizer according to an embodiment.
Figure 13I:
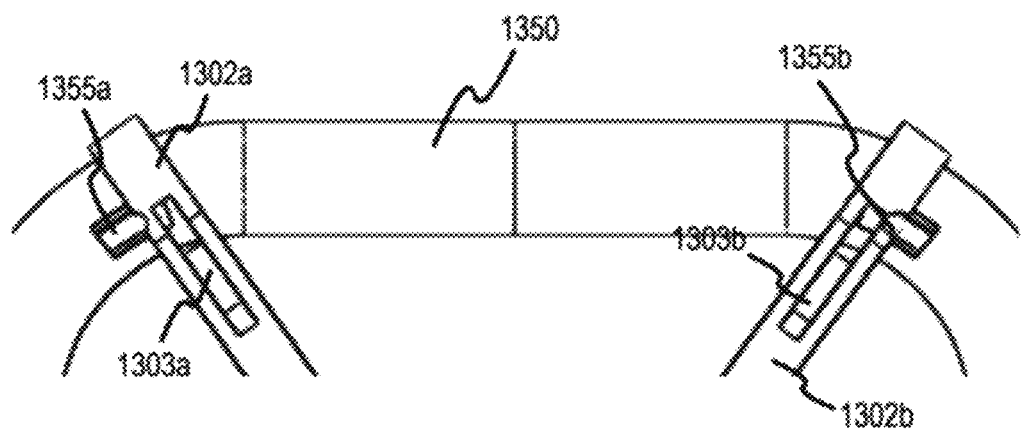

FIGS. 13A and 13B depict schematic diagrams of perspective views of an illustrative stabilizer 1300 to be used as an expansion tool of a percutaneous annuloplasty system according to an embodiment. The illustrated stabilizer 1300 may include one or more arms or prongs 1302, such as, for example, two arms 1302a, 1302b. FIG. 13A depicts a perspective view of the stabilizer 1300 separated from other components of the percutaneous annuloplasty system. FIG. 13B depicts the stabilizer 1300 disposed through a delivery catheter 1306 and engaging an annuloplasty ring 1350. The stabilizer 1300 may be used to position, orient, and otherwise manipulate the annuloplasty ring 1350 to achieve intimate contact in abutment with tissue of the annulus of a target heart valve.

Referring generally and collectively to FIGS. 13A-13D, the arms 1302 of the stabilizer 1300 may be configured to extend outward at an angle from a central column 1304, thereby forming a rib structure. The rib structure, particularly the arms 1302 and central column 1304, may be laser cut from a shape memory material, such as, for example, nitinol. The stabilizer 1300 may be cut from a hollow tube such that the central column 1304 has a hollow cylindrical shape. The arms 1302 may be heat set to extend at an angle from the central column 1304.

The illustrated stabilizer 1300 of FIGS. 13A and 13B may include two arms 1302a, 1302b arranged, for example as a bipod. The two arms 1302a, 1302b in cooperation with a ring shuttle 1361 of a delivery system of the percutaneous annuloplasty system form a tripod structure engaging the annuloplasty ring 1350 at three points. The plurality of arms 1302 may be loaded into a delivery catheter 1306 together with the annuloplasty ring 1350 (for example, configured in the elongate insertion geometry). As the arms 1302 extend from a distal end of the delivery catheter 1306, they may automatically expand outward and may be configured to align with and engage the annuloplasty ring 1350 as shown in FIG. 13B. When aligned and engaged with the annuloplasty ring 1350, the stabilizer 1300 may be used to push/pull the annuloplasty ring toward the tissue of the annulus of a valve.

The illustrated stabilizer of FIGS. 13A and 13B may be configured to engage a top surface of the annuloplasty ring 1350 to pull the annuloplasty ring. For example, the plurality of arms 1302 may include a curved, angled, or hooked portion at a distal end to facilitate engagement with the annuloplasty ring 1350. The stabilizer 1300 may be used to pull the annuloplasty ring 1350 toward the heart valve to facilitate intimate contact of the annuloplasty ring with the annulus to enhance an anchor deployment process to fasten the annuloplasty ring to the annulus.

The stabilizer 1300, particularly the arms 1302, may also be configured to function as an expansion tool to engage the annuloplasty ring 1350 and effectuate and/or facilitate transition of the annuloplasty ring from a contracted state to an expanded state. For example, a superelastic property and memorized shape of the plurality of arms 1302 may enable the arms to engage an inner surface of the annuloplasty ring 1350 and via its inherent material properties, exert outward force to expand the annuloplasty ring. In other embodiments, a suture or other elongate member may enable percutaneous manipulation of one or more of the plurality of arms 1302 to effectuate expansion of the annuloplasty ring 1350.

In some embodiments, the arms 1302 of the stabilizer 1300 may also include a feature that locks the stabilizer against the annuloplasty ring 1350, thereby preventing each arm from moving relative to another, such as, for example, after the deployment and during creation of intimate contact between the ring and the tissue. For example, the arms 1302 of the stabilizer 1300 may each have at least one strat 1303a, 1303b (collectively 1303). Each strat 1303 may prevent its respective arm 1302 from sliding on the annuloplasty ring 1350 and may allow and/or facilitate engagement on a particular position of the ring. In some embodiments, a particular position of engagement on the annuloplasty ring 1350 may ensure a proper ring size, shape, and/or orientation. After aligning the stabilizer 1300 relative to the annuloplasty ring 1350, the stabilizer may be fixed in relation to the ring by the strats 1303. By manipulating the tool 1300, the operator may be able to manipulate the position and orientation of the annuloplasty ring 1350.

In various embodiments, as shown in FIGS. 13E-13I, the annuloplasty ring 1350 may also have at least one strat 1355a, 1355b (collectively 1355). Each strat 1355 may prevent the annuloplasty ring 1350 from sliding when attached to the arms 1302. In some embodiments, each strat 1355 may allow and/or facilitate engagement of a particular portion of the annuloplasty ring 1350 with a particular arm 1302. In some embodiments, a particular position of engagement of the strats 1355 on the annuloplasty ring 1350 may ensure a proper ring size, shape, and orientation. After aligning the stabilizer 1300 (FIG. 13C) relative to the annuloplasty ring 1350, the stabilizer may be fixed in relation to the ring by the strats 1355. In some embodiments, the strats 1355 on the annuloplasty ring 1350 may be used in conjunction with the strats 1303 on the arms 1392 of the stabilizer. In other embodiments, the strats 1355 on the annuloplasty ring 1350 may be used in lieu of the strats 1303 on the arms 1392 of the stabilizer.

Figure 14A:
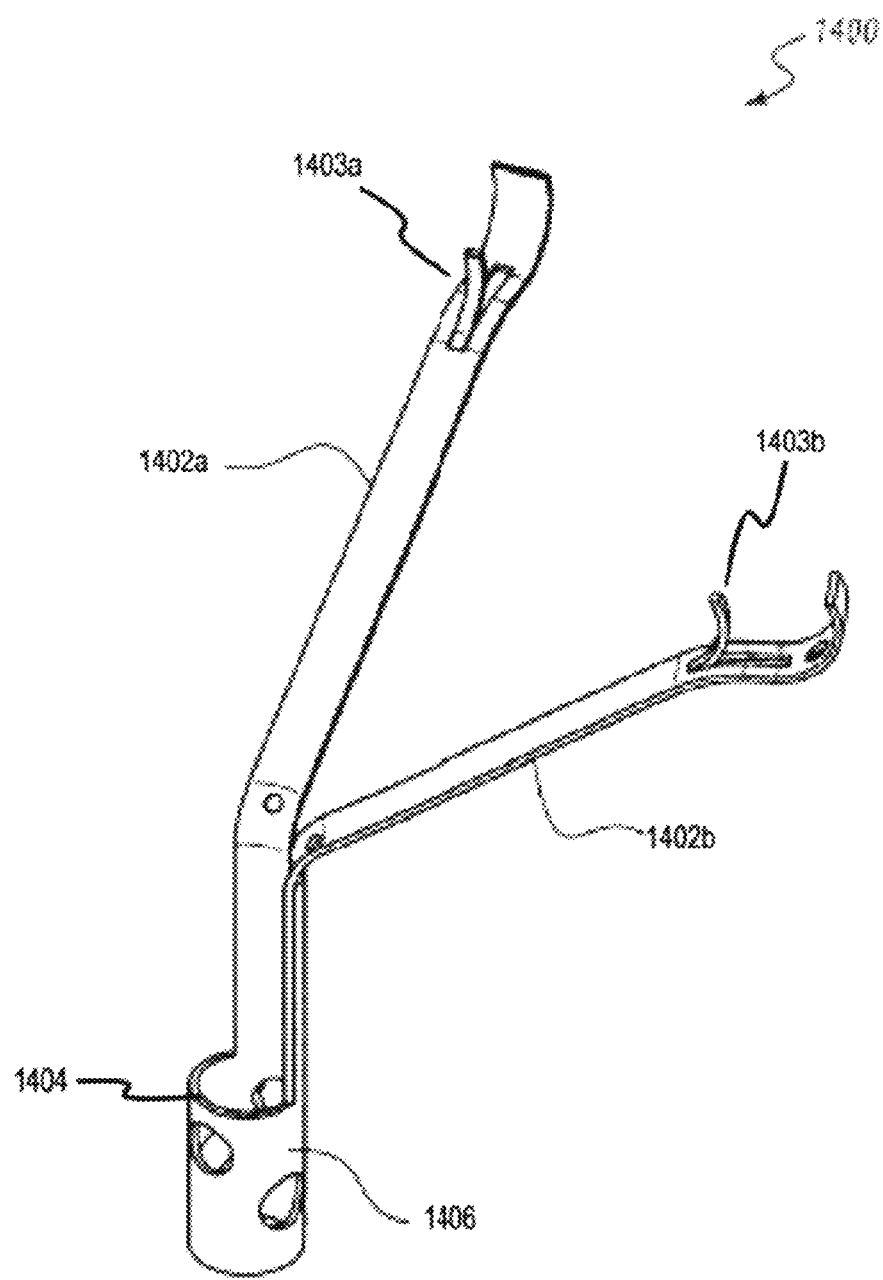
FIGS. 14A and 14B depict perspective views of a stabilizer of a percutaneous annuloplasty system according to an embodiment.
Figure 14B:
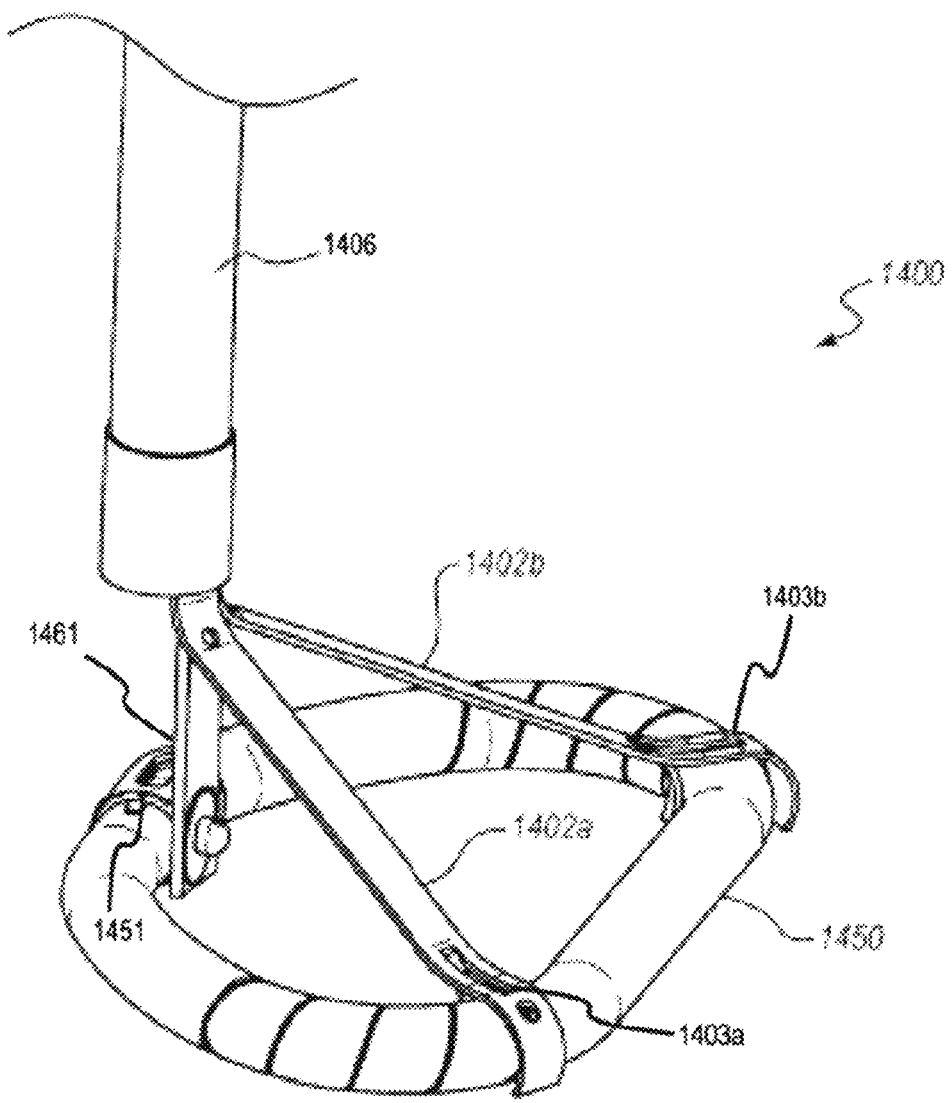

FIGS. 14A and 14B depict diagrams illustrating perspective views of a stabilizer 1400 of a percutaneous annuloplasty system according to an embodiment. The stabilizer 1400 may be configured to push and/or press an annuloplasty ring 1450 (from above) into intimate contact with, or abutment against, an annulus of a target heart valve. The illustrated stabilizer 1400 may include a plurality of arms or prongs 1402, such as, for example two arms 1402a, 1402b. FIG. 14A depicts a perspective view of the stabilizer 1400 separated from other components of the percutaneous annuloplasty system. FIG. 14B depicts the stabilizer 1400 disposed through a delivery catheter 1406 and engaging an annuloplasty ring 1450 from above. The stabilizer 1400 may be used to position, orient, and/or otherwise manipulate the annuloplasty ring 1450 to achieve intimate contact with or abutment against tissue of the annulus of a target heart valve.

The arms 1402 of the stabilizer 1400 may be configured to extend outward at an angle from a central column 1404, thereby forming a rib structure. The rib structure, particularly the arms 1402 and central column 1404, may be laser cut from a shape memory material, such as nitinol. The stabilizer 1400 may be cut from a hollow tube such that the central column 1404 has a hollow cylindrical shape. The arms 1402 may be heat set to extend at an angle from the central column 1404.

The illustrated stabilizer 1400 of FIGS. 14A and 14B may include two arms 1402a, 1402b arranged, for example, in the shape of a bipod. The two arms 1402a, 1402b, in cooperation with a ring shuttle 1451 of the percutaneous annuloplasty system, may form a tripod structure engaging the annuloplasty ring 1450 at three points. The plurality of arms 1402 may be loaded into a delivery catheter 1406 together with the annuloplasty ring 1450 (for example, configured in the elongate insertion geometry). As the arms 1402 emerge from a distal end of the delivery catheter 1406, they may automatically expand outward and may be configured to align with and engage the annuloplasty ring 1450, as shown in FIG. 14B. When aligned and engaged with the annuloplasty ring 1450, the stabilizer 1400 may be used to push/pull the annuloplasty ring toward the tissue of an annulus of a heart valve.

The illustrated stabilizer of FIGS. 14A and 14B may be configured to engage a top surface of the annuloplasty ring 1450 from above to push the annuloplasty ring. For example, the plurality of arms 1402 may include a curved, angled, and/or hooked portion at a distal end to facilitate engagement with the annuloplasty ring 1450. The stabilizer 1400 may be used to push the annuloplasty ring 1450 from above in a downward direction toward the heart valve to facilitate intimate contact of the annuloplasty ring with the annulus to enhance an anchor deployment process and/or to aid in the fastening of the annuloplasty ring to the annulus.

The stabilizer 1400, particularly the arms 1402, may also be configured to function as an expansion tool to engage the annuloplasty ring 1450, effectuate, and/or facilitate transition of the annuloplasty ring from a contracted state to an expanded state. For example, a superelastic property and shape memory property of the plurality of arms 1402 may enable the arms to engage an inner surface of the annuloplasty ring 1450 and exert an outward force to expand the annuloplasty ring. The stabilizer 1400 may be manipulated to expand the annuloplasty ring 1450 within the annulus of the target valve, or otherwise press the annuloplasty ring against the valve and thereby effectuating expansion of the annuloplasty ring to the expanded state. In other embodiments, a suture or other elongated member may enable percutaneous manipulation of one or more of the plurality of arms 1402 to effectuate expansion of the annuloplasty ring 1450.

Figure 15A:
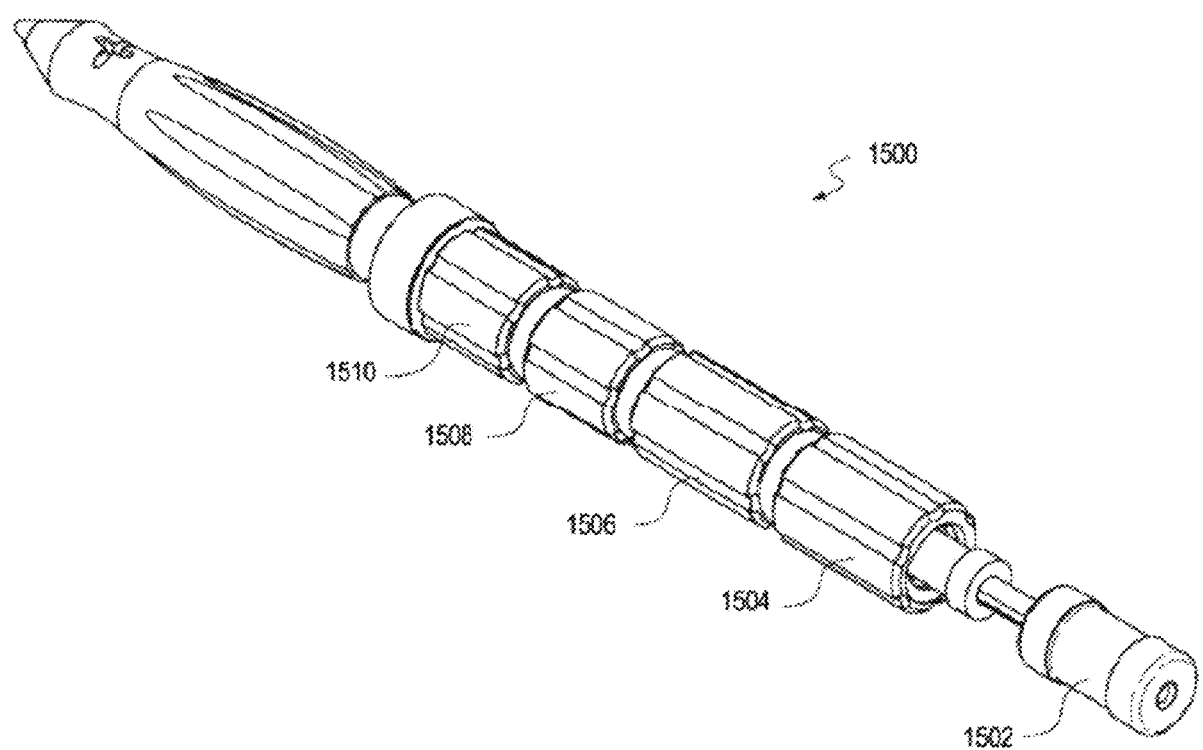
FIG. 15A depicts a perspective view of a proximal end of a handle of a percutaneous annuloplasty system according to an embodiment.
Figure 15B:
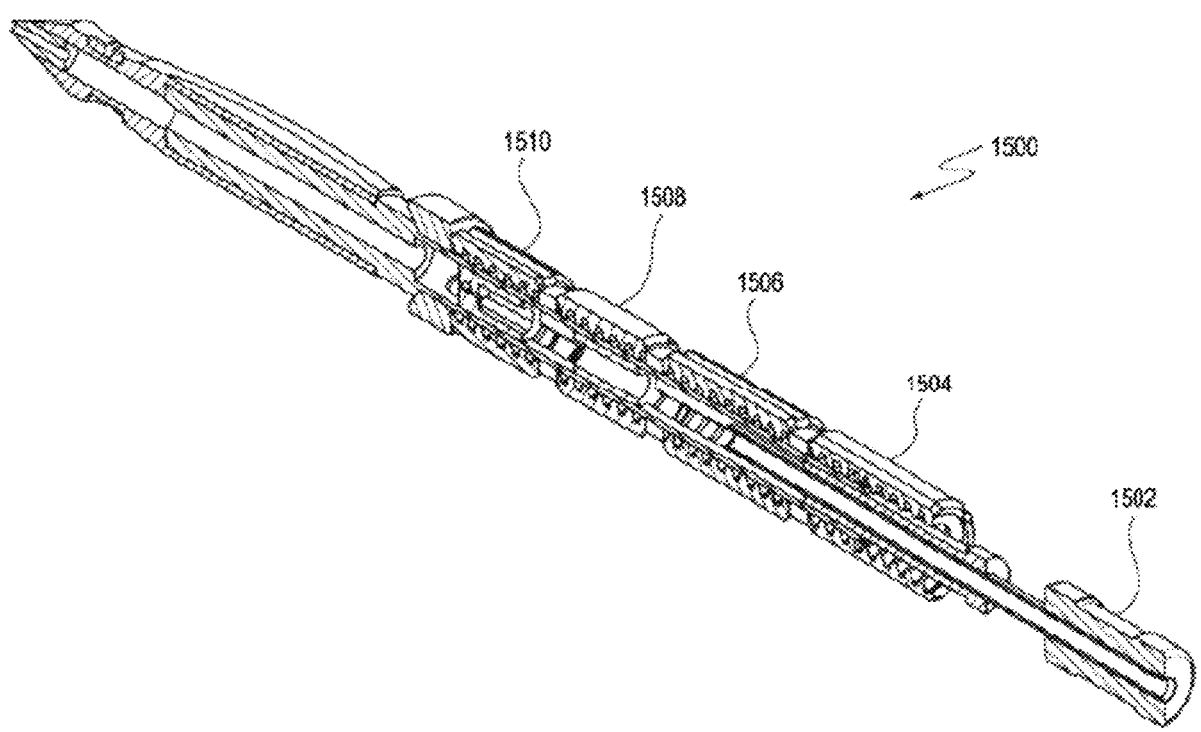
FIG. 15B depicts a cross-sectional view of the proximal end of a handle of a percutaneous annuloplasty system according to an embodiment.

FIG. 15A depicts a diagram of a perspective view of an illustrative proximal end handle, generally designated 1500, of a percutaneous annuloplasty system according to an embodiment. FIG. 15B depicts a diagram of a perspective cross-sectional view of the proximal end handle 1500 of FIG. 15A. In various embodiments, the proximal end handle 1500 may enable percutaneous transcatheter deployment of an annuloplasty ring. More particularly, the proximal end handle 1500 may enable percutaneous manipulation of an annuloplasty system configured to deliver, configure, and/or orient an annuloplasty ring and to fasten the annuloplasty ring to the annulus of a target valve.

In various embodiments, the proximal end handle 1500 may include one or more rotating knobs that are configured to perform or enable one or more functions. In some embodiments, one rotatable knob may be used for each function to be performed. In other embodiments, one rotatable knob may be used for a plurality of functions. A ring closure knob 1502 may enable closure of the annuloplasty ring to transition from an elongated insertion geometry to an annular operable geometry, as described in greater detail herein. A ring snap knob 1504 may enable snapping together of first and second ends (for example, distal and proximal ends) of the annuloplasty ring or other manipulation of a ring closure lock, as described herein. An anchor deployment knob 1506 may enable deployment of anchors of an annuloplasty ring to fasten the annuloplasty ring to the annulus of the target heart valve, as described herein. An A-P adjustment knob 1508 may enable contraction of the annuloplasty ring from an expanded state to a contracted state, as described herein. In other embodiments, the A-P adjustment knob 1508 may also enable manipulation of a stabilizer to facilitate expansion of the annuloplasty ring to an expanded state (for example, prior to deployment of the anchors). A ring release knob 1510 may enable release of the annuloplasty ring from a delivery system and/or delivery shuttle of a percutaneous annuloplasty system. Additional or fewer knobs may be possible, depending on the functions to be performed. Furthermore, the positioning of each knob relative to other knobs as shown in FIG. 15A is merely illustrative. Accordingly, those having ordinary skill in the art will recognize other positions of each knob relative to other knobs as being included within the scope of this disclosure.

In various embodiments, each of the knobs 1502, 1504, 1506, 1508, 1510 may be coupled to an independent system of cables and/or sutures. Manipulation of a respective cable and/or suture may be achieved by rotating the respective knob 1502, 1504, 1506, 1508, 1510. As shown in FIG. 15B, each of the knobs 1502, 1504, 1506, 1508, 1510 may be mechanically coupled to a respective translation gear mechanism. The gear mechanism may be connected to a respective cable or suture that is configured to perform a given function.

Figure 16A:
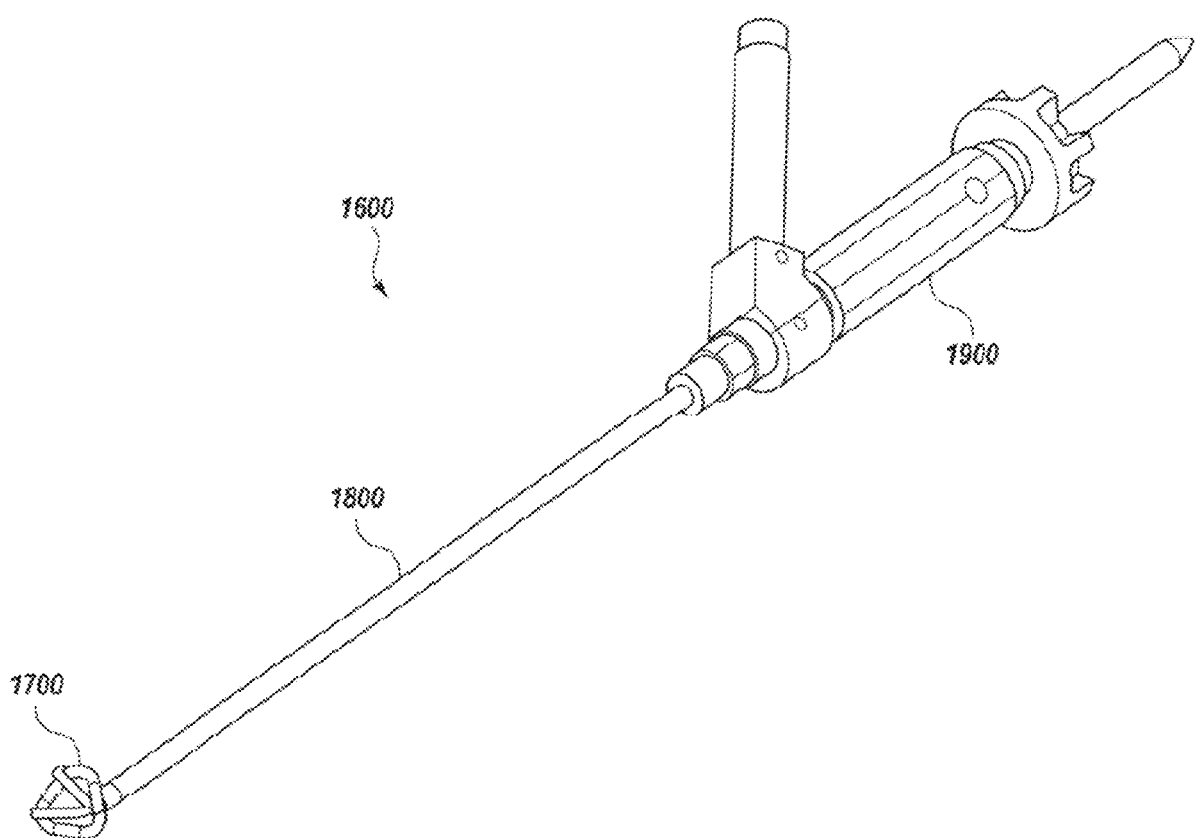
FIGS. 16A and 16B depict diagrams of perspective views of an illustrative delivery system of a percutaneous annuloplasty system according to an embodiment.
Figure 16B:
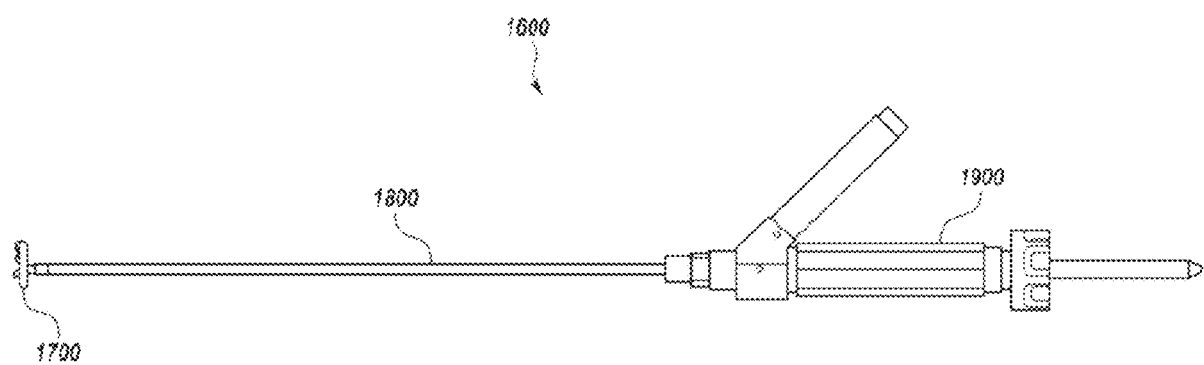

FIGS. 16A and 16B depict diagrams of perspective views of an illustrative delivery system, generally designated 1600, of a percutaneous annuloplasty system, according to an embodiment. In some embodiments, the delivery system 1600 may include a plurality of sections, such as, for example, a distal end section 1700, a catheter section 1800, and/or a proximal handle section 1900. The delivery system 1600 may be configured to enable percutaneous transcatheter deployment of an annuloplasty ring, as described herein. More particularly, the delivery system 1600 may enable percutaneous manipulation of an annuloplasty system configured to deliver, configure, and/or orient an annuloplasty ring. Further, the delivery system 1600 may be configured to fasten the annuloplasty ring to the annulus of a target heart valve, as described in greater detail herein.

Figure 17A:
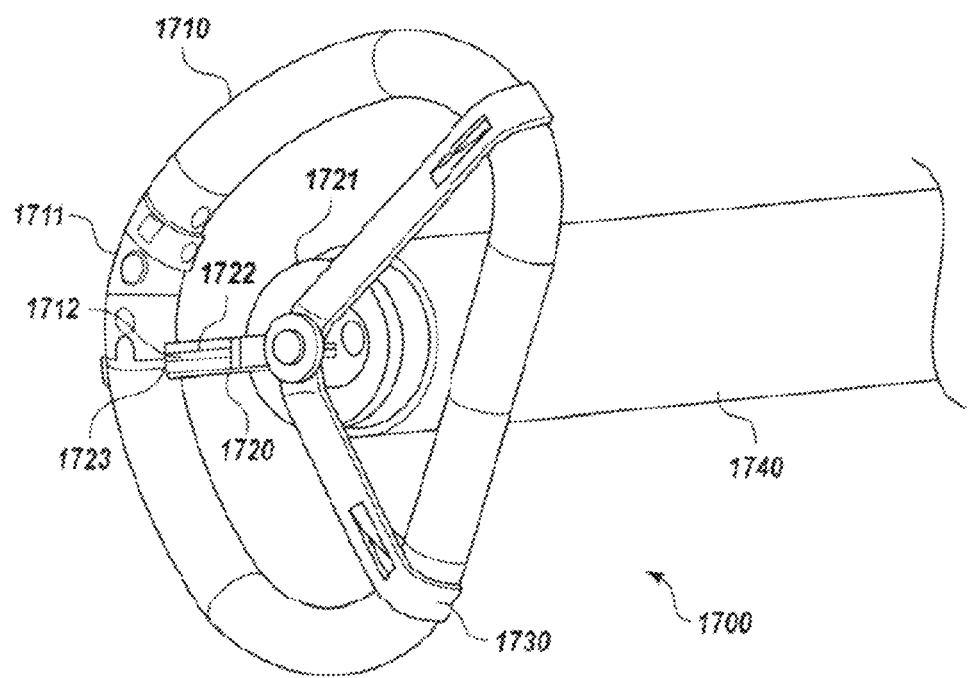
FIGS. 17A and 17B depict illustrative examples of a full assembly of the ring, stabilizer and distal end of the catheter as configured in a target site after deployment of the ring from the catheter according to an embodiment.
Figure 17B:
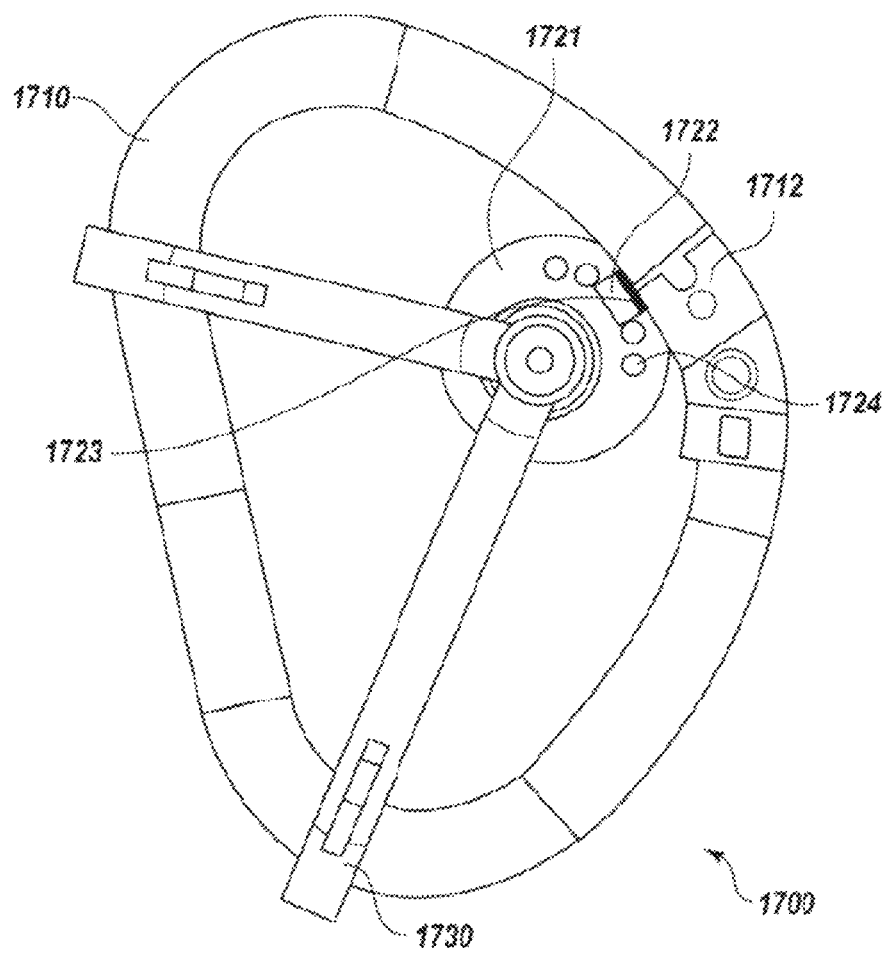

FIGS. 17A and 17B depict illustrative examples of a full assembly of a ring 1710, a stabilizer 1730, and a distal end of the catheter 1740 as configured in a target site after deployment of the ring from the catheter. FIGS. 17A and 17B further depict an illustrative example of an attachment mechanism between the ring 1710 and the stabilizer 1730. As described in greater detail herein, the connection may be accomplished between a pivot point 1712 on the ring 1710 and the ring shuttle 1722 on the stabilizer 1730 via a wire 1723 that may be configured to pass through the catheter 1740 to the proximal end of the delivery system.

Also shown in FIGS. 17A and 17B is an illustrative example of a delivery system 1700 showing, at the distal end, a solid piece 1721. The solid piece 1721 may be manufactured from any material, such as, for example, stainless steel. The solid piece 1721 may be configured for one or more functions. Illustrative functions may include, but are not limited to, holding the ring shuttle 1722 in a particular position, locating the stabilizer 1730 in relation to the ring shuttle and/or the ring 1710 at the target site, and guiding the sutures from the ring through the holes 1724 towards the proximal end of the delivery system 1740.

Figure 18A:
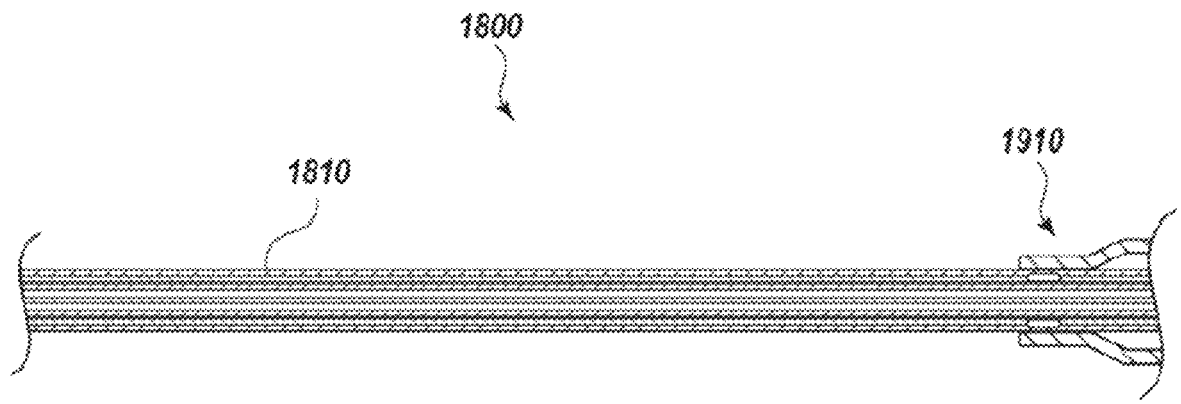
FIGS. 18A and 18B depict illustrative longitudinal cross-sectional views of a catheter connecting the distal end of the delivery system of FIG. 17A to the proximal end of the delivery system of FIG. 16A or 16B according to an embodiment.
Figure 18B:
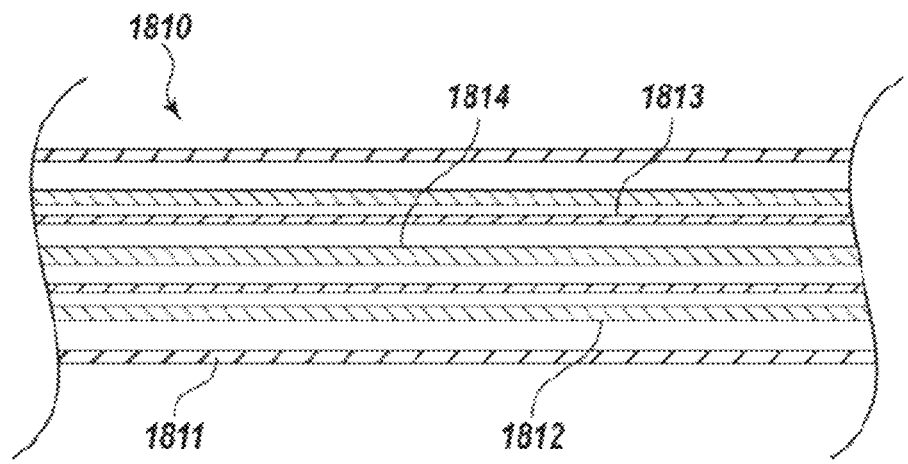

FIGS. 18A and 18B depict a longitudinal cross-sectional view of an illustrative catheter, generally designated 1800, connecting the distal end of the delivery system 1700 (FIGS.

Figure 19A:
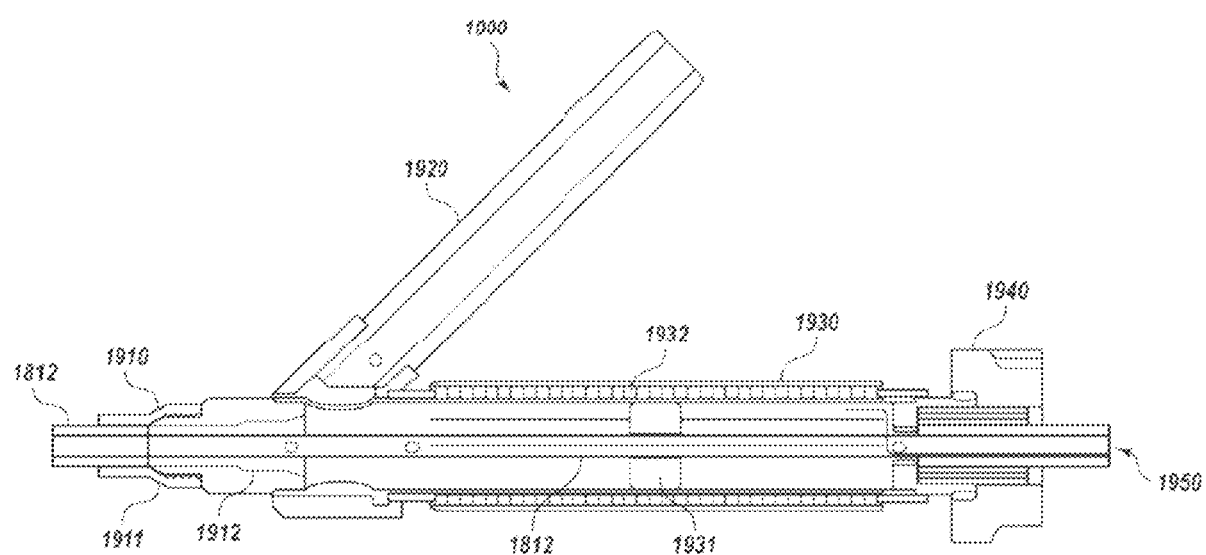
FIGS. 19A, 19B, and 19C depict illustrative examples of the proximal side of a delivery system which functions as a handle according to an embodiment.
Figure 19B:
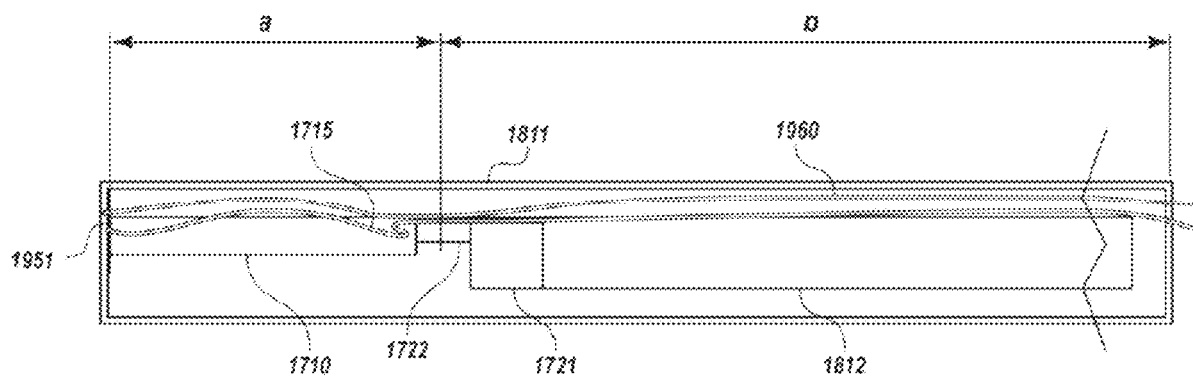

17A and 17B) to the proximal end of the delivery system 1900 (FIGS. 19A and 19B). The catheter 1800 may include one or more lumens 1810 containing, but not limited to, a hollow outer sleeve 1811 that is attached to the proximal end of the delivery system 1910.

In various embodiments, an inner hollow shaft 1812 may be located within the hollow outer sleeve 1811. Referring also to FIG. 19A, the inner hollow shaft 1812 may be connected to a moving member 1931 that is configured to transfer movement of a rotating knob 1932 to the inner hollow shaft 1812 and to the solid piece 1721 (FIGS. 17A and 17B) at the distal end of the delivery system 1700 (FIGS. 17A and 17B).

In some embodiments, a stabilizer shaft 1813 may be located within the inner hollow shaft 1812. The stabilizer shaft 1813 may connect the stabilizer 1730 to the proximal end of the delivery system 1700 (FIGS. 16A and 16B). In some embodiments, the stabilizer shaft 1813 may be configured to allow distal control of the stabilizer 1730 from the proximal end 1950 (FIG. 19A). In some embodiments, a guidewire or pig-tail catheter 1814 may be passed through the center of the stabilizer shaft 1813. The guidewire or pig-tail catheter 1814 may generally be one of a commonly used tool in the cardiovascular field to function as a guide in the heart chambers and/or to function as a conduit for injection of contrast media for fluoroscopy.

Figure 19C:
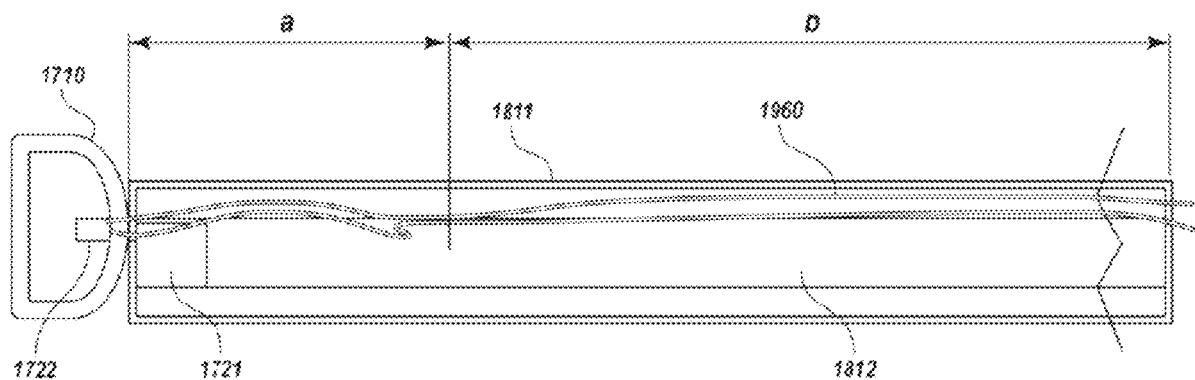

FIGS. 19A, 19B, and 19C depict an illustrative embodiment for the proximal side of the delivery system 1900, which may function as a handle. The system 1900 may include one or more functional mechanisms. Illustrative functional mechanisms may include, but are not limited to, a ring deployment mechanism 1930, a ring closure or snapping mechanism 1940, a barb or anchor deployment mechanism 1920, and control channel mechanism for the ring release wire 1723 (FIGS. 17A and 17B). The ring deployment mechanism 1930 may include a rotating knob 1932 and/or a moving member 1931 that may be attached to the inner hollow shaft 1812. In some embodiments, the knob 1932 may be configured to be rotated such that the ring 1710 (FIGS. 17A and 17B) is pushed distally and away through the outer sleeve 1811, thereby deploying the ring 1710 from the catheter. The end of the suture 1960 coming off of the ring 1710 (FIGS. 17A and 17B) may be fixed at the proximal end 1950 such that when the ring deploys, the suture may be placed under a constant tension.

FIG. 19B depicts an illustrative suture 1960 attached to the ring 1710 at the distal end 1951. The suture may pass through the proximal end of the ring 1715, the ring shuttle 1722, the solid piece 1721, and the outer sleeve 1811 to the proximal end of the delivery system 1950 (FIG. 19A). The total length of the suture 1960 may be the length of a first portion a plus the length of a second portion b (a+b).

FIG. 19C depicts an illustrative ring 1710 after deployment from the outer sleeve 1811. As shown in FIG. 19C, the suture 1960 may remain the same length as it is attached at the same points of the ring 1710 relative to the delivery system. Accordingly, the suture 1960 may be placed under tension.

Referring again to FIG. 19A, a channel 1920 may be provided for one or more barb deployment elongated members (such as, for example, sutures) to be held and pulled once barbs and/or anchors are deployed, as described in greater detail herein. Any number of barb deployment members may be placed via the channel 1920. In some embodiments, the number of barb deployment members may correspond to a number of windows, as described herein. For example, 1 barb deployment member, 2 barb deployment members, 3 barb deployment members, 4 barb deployment members, 5 barb deployment members, 6 barb deployment members, 7 barb deployment members, 8 barb deployment members, 9 barb deployment members, 10 barb deployment members or more may be placed via the channel 1920.

An annuloplasty ring, as disclosed above, may be used to adjust the shape of an annulus of a cardiovascular valve, thereby bringing its leaflets into a functional geometry. Additionally, such a device may be used to provide a stabilizing platform for a replacement cardiovascular valve if the natural cardiovascular valve is defective, degraded, or diseased. Such a use may be indicated if the natural valve structure and its environment are too deformable to permit long-term placement of the replacement valve. Natural cardiovascular valves that may be treated in this manner may include cardiac valves or venous valves. Cardiac valves may include the mitral valve, the aortic valve, the tricuspid valve, and the pulmonary valve. In the disclosure below, reference is made to an adjustable stabilizing ring that may be used in conjunction with a replacement valve. It may be understood that embodiments of such an adjustable stabilizing ring, along with the variety of systems, implements, and catheters that may be used for its deployment in the cardiovascular system, may include the embodiments of annuloplasty rings and the systems, implements, and catheters that have been disclosed hereinabove.

Figure 20A:
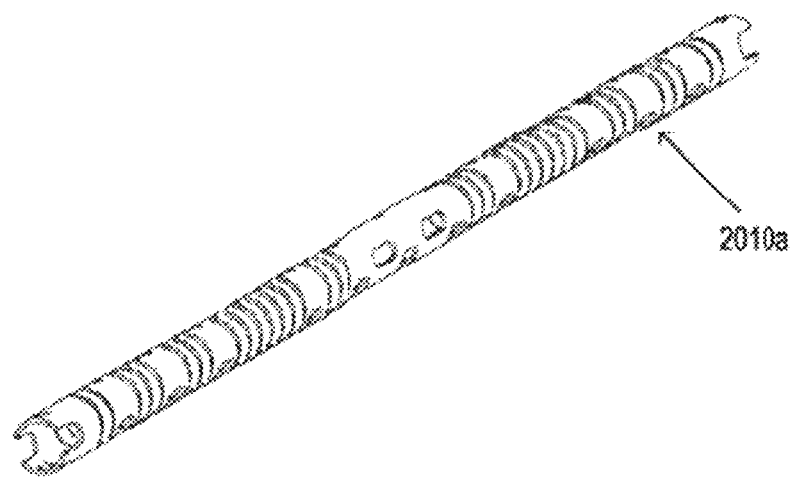
FIG. 20A depicts a perspective view of an illustrative example of an adjustable valve support ring in an extended state according to an embodiment.
Figure 20B:
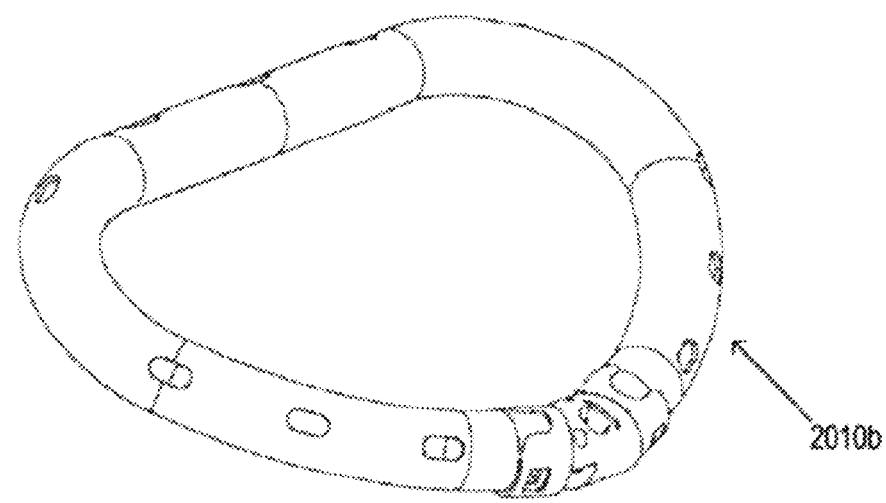
FIG. 20B depicts a perspective view of an illustrative example of an adjustable valve support ring in a closed geometry according to an embodiment.
Figure 20C:
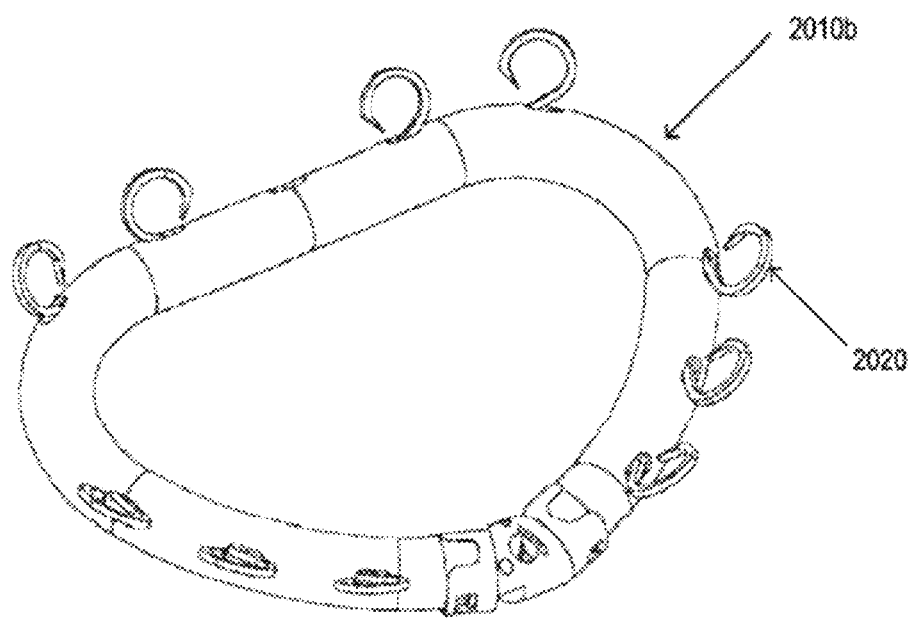
FIG. 20C depicts a perspective view of an illustrative example of an adjustable valve support ring in a closed geometry with extended anchors according to an embodiment.

One embodiment of such an adjustable stabilizing ring is depicted in FIGS. 20A-C. The adjustable stabilizing ring may include a body member capable of assuming one or more different geometric shapes. In some non-limiting embodiments, the body member may be composed of a memory metal, a nickel titanium alloy, a stainless steel alloy, or a cobalt-chrome alloy, alone or in combination. Such materials may have physical and/or mechanical properties that may permit the body member to assume the one or more geometric shapes. In some embodiments, the adjustable stabilizing ring may initially be present in an elongate geometry 2010*a* as depicted in FIG. 20A. Such a geometry may allow the body member of the stabilizing ring to be inserted into the heart or vasculature by means of a narrow catheter.

In another embodiment, the body member of the adjustable stabilizing ring may transition from the elongate geometry 2010*a* to an annular operable geometry 2010*b*, as depicted in FIG. 20B. The annular operable geometry 2010*b* may take on any closed geometric shape including, without limitation, a circular shape, an oval shape, a D-shape, or any other continuously enclosed smooth shape. An adjustable stabilizing ring having a D-shaped annular operable geometry 2010*b* may have dimensions appropriate to the size of the natural valve annulus for which it may be used. The dimensions may include an anterior-posterior diameter of about 17 mm to about 23 mm, and a commissure-commissure diameter of about 28 mm to about 36 mm Non-limiting examples of an anterior-posterior diameter may include a diameter of about 17 mm, about 18 mm, about 19 mm, about 20 mm, about 21 mm, about 22 mm, about 23 mm, or ranges between any two of these values (including endpoints). Non-limiting examples of a commissure-commissure diameter may include a diameter of about 28 mm, about 29 mm, about 30 mm, about 31 mm, about 32 mm, about 33 mm, about 34 mm, about 35 mm, about 36 mm, or ranges between any two of these values (including endpoints). In the annular operable geometry 2010*b*, the adjustable stabilizing ring may be rigid or semi-rigid.

The stabilizing ring in its annular operable geometry 2010*b* may also include one or more anchors 2020 as depicted in FIG. 20C. Such anchors 2020 may be deployed to engage the tissue of a cardiovascular valve, such as the annular region. Over time, the engaged tissue may grow around the individual anchors 2020 thereby forming a mechanical bond that can stabilize the ring in place near the natural cardiovascular valve.

Because the stabilizing ring may be emplaced in the heart or vasculature through the use of a catheter, it may not be possible for the physician or other health care professional to visualize the placement directly. Imaging technology may be required to determine the proper placement of the stabilizing ring. In some embodiments, the stabilizing ring may be radiopaque or include radiopaque material to permit its visualization during emplacement.

Because the stabilizing ring may be stabilized near the natural cardiovascular valve by the anchors 2020, a replacement valve that is placed in mechanical contact with the ring may be similarly stabilized. Such a replacement valve may be composed of an implantable valve frame to which one or more valve leaflets are attached. The implantable valve frame may be composed of any material that is biocompatible and resistant to thrombus formation. Non-limiting examples of such valve frame material may include memory metal, a nickel titanium alloy, a stainless steel alloy, and a cobalt-chrome alloy. Such a replacement valve may include the same number of valve leaflets as the natural valve that it may replace. Thus, the replacement valve may include an implantable valve frame having one, two, or three valve leaflets in contact therewith.

Figure 21A:
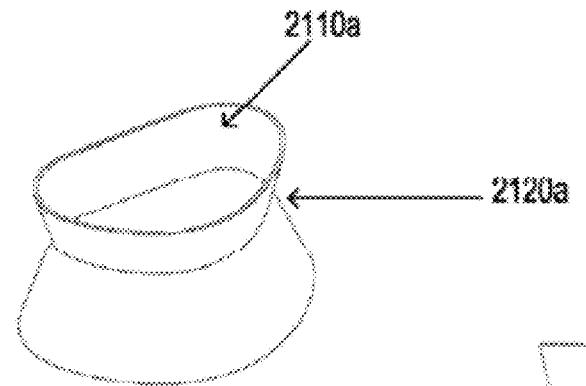
FIG. 21A depicts an isometric view of an illustrative example of an angled D-shaped cylindrical valve frame according to an embodiment.
Figure 21B:
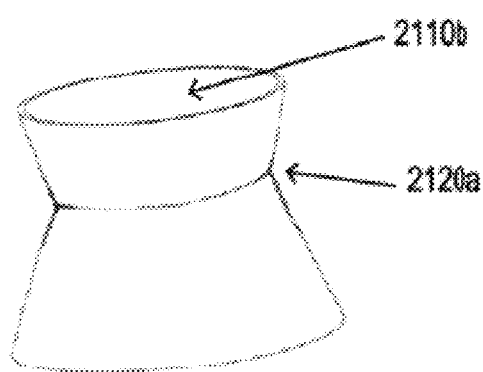
FIG. 21B depicts an isometric view of an illustrative example of an angled cylindrical valve frame according to an embodiment.
Figure 21C:
FIG. 21C depicts a side view of the D-shaped valve frame depicted in FIG. 21A or the cylindrical valve frame depicted in FIG. 21B according to an embodiment.
Figure 21D:
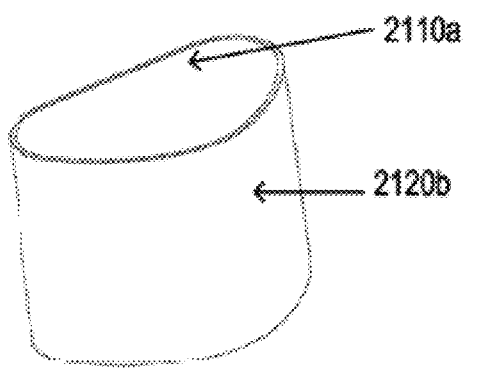
FIG. 21D depicts an isometric view of an illustrative example of a straight D-shaped valve frame according to an embodiment.
Figure 21E:
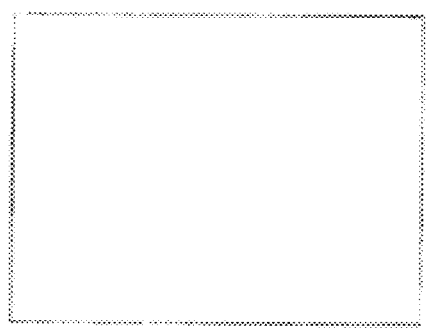
FIG. 21E depicts a side view of the straight D-shaped valve frame depicted in FIG. 21D according to an embodiment.

Implantable valve frames may include a variety of shapes and sizes, some non-limiting examples of which are depicted in FIGS. 21A-H. As depicted in FIG. 21A, one embodiment of an implantable valve frame may include a frame having a D-shaped cross-section 2110a and a constricted profile 2120a (depicted in FIG. 21C). As depicted in FIG. 21B, another embodiment of an implantable valve frame may include a frame having a circular cross-section 2110b and a constricted profile 2120a (also depicted in FIG. 21C). As depicted in FIG. 21D, another embodiment of an implantable valve frame may include a frame having a D-shaped cross-section 2110a and a straight profile 2120b (also depicted in FIG. 21E) In still another embodiment, an implantable valve frame may include a frame having a circular cross section (2110b as illustrated in FIG. 21B) and a straight profile (2120b as illustrated in FIG. 21D).

Figure 21F:
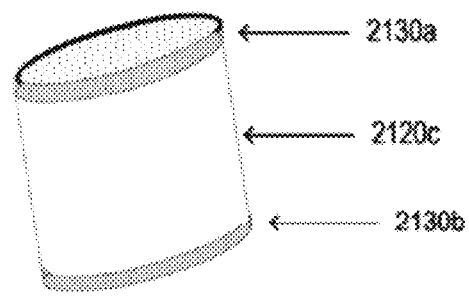
FIG. 21F depicts an isometric view of an illustrative example of a straight cylindrical valve frame further depicting support elements and a continuous bridging element surface according to an embodiment.
Figure 21G:
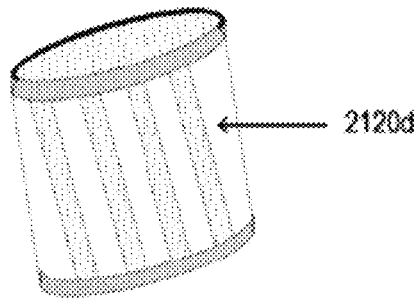
FIG. 21G depicts an isometric view of an illustrative example of a straight cylindrical valve frame further depicting support elements and a plurality of independent bridging elements according to an embodiment.

In some embodiments, as depicted in FIGS. 21F and 21G, an implantable valve frame may be formed from a first support element 2130a, a second support element 2130b, and at least one bridging element 2120c extending from the first support element to the second support element. The one, two, three, or four replacement valve leaflets associated with the implantable valve frame may be at least partially secured to the first support element 2130a, the second support element 2130b, the at least one bridging element 2120c, or any combination thereof. In some embodiments, the at least one bridging element 2120c may be composed of a single continuous surface having a first end in physical contact with the entire first support element 2130a and a second end in physical contact with the entire second support element 2130b. In some embodiments, the implantable valve frame may be composed of a first support element 2130a, a second support element 2130b, and at least one bridging element 2120c, any one or more of which may be composed of a collapsible material. In some embodiments, the implantable valve frame may be composed of a first support element 2130a, a second support element 2130b, and at least one bridging element 2120c in which the at least one bridging element extends radially inwards toward a central axis of the valve frame. It may be recognized that such a radially inward extent, for a valve frame having a single bridging element, may result in a valve frame having a constricted profile as depicted in FIGS. 21A-C. In some embodiments, the implantable valve frame may be composed of a first support element 2130a, a second support element 2130b, and at least one bridging element 2120c, any one or more of which may be composed of a woven material.

In another embodiment, depicted in FIG. 21G, the at least one bridging element may be composed of a plurality of independent or mutually linked bridging elements 2120d. Some embodiments may include a plurality of bridging elements arranged in a crisscross manner, such as may be found in an expandable gate. In alternative embodiments, the at least one bridging element may be constructed in the manner of a vascular stent. A valve frame having bridging elements arranged as associated linked components may be used in conjunction with a stabilizing ring having anchors. The linked components in the system may be rigid or semi-rigid depending on the nature of the linkage among the linked components. It may be recognized that implantable valve frames in general may be at least partially collapsible, collapsible, rigid, or semi-rigid according to their individual designs.

Figure 21H:
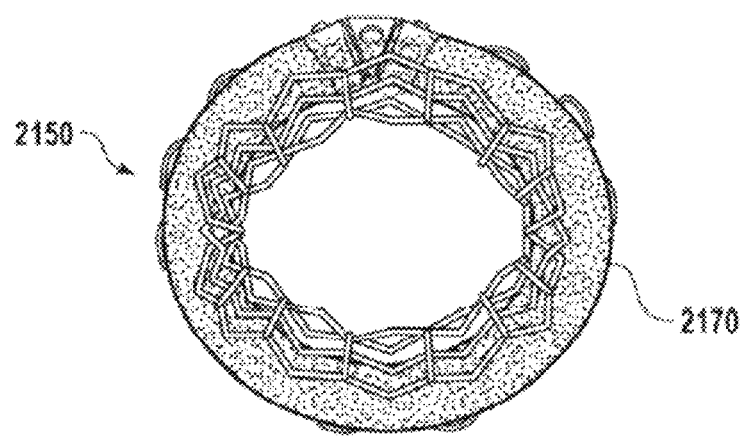
FIG. 21H depicts an illustrative example of an adjustable stabilizing ring according to an embodiment.

FIG. 21H further depicts a pliable coating material 2170 that may be applied to the stabilizing ring 2150. It may be appreciated that the stabilizing ring 2150, the valve frame, or both may be coated with such a pliable coating material 2170. In some embodiments, the pliable coating material 2170 may be composed of a polymer. In one non-limiting example, the pliable material may be a polyester.

Figure 22A:
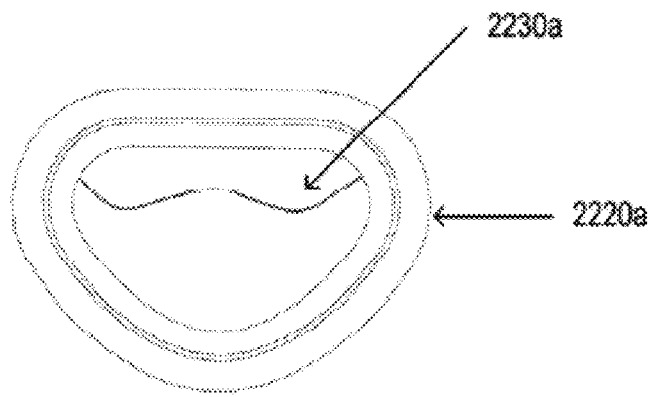
FIG. 22A depicts a top view of an illustrative example of an angled D-shaped cylindrical valve frame including an exemplary bi-leaflet valve according to an embodiment.
Figure 22B:
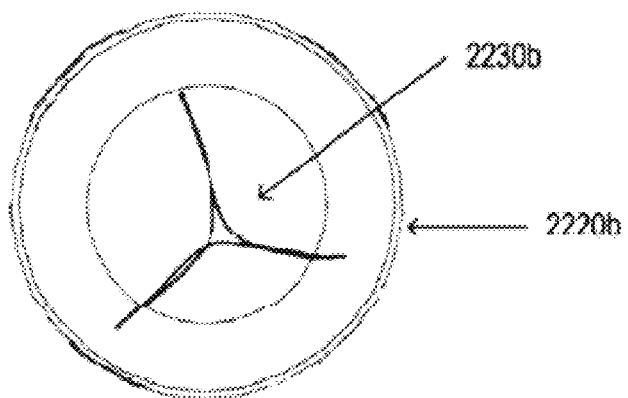
FIG. 22B depicts a top view of an illustrative example of an angled cylindrical valve frame including an exemplary tri-leaflet valve according to an embodiment.
Figure 22C:
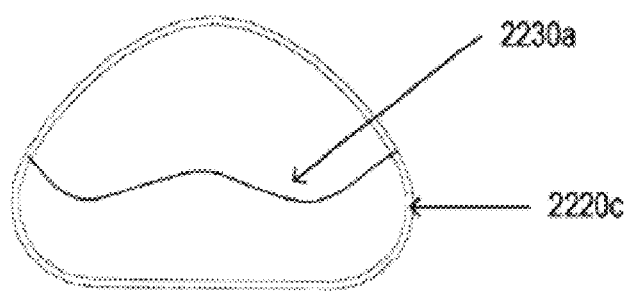
FIG. 22C depicts a top view of an illustrative example of a straight D-shaped cylindrical valve frame including an exemplary bi-leaflet valve according to an embodiment.

FIGS. 22A-C depict several non-limiting examples of implantable valve frames including replacement valves that may be incorporated therein. Thus, FIG. 22A depicts a frame having a D-shaped cross-section with a constricted profile 2220a incorporating a bi-leaflet valve 2230a. FIG. 22B depicts a frame having a circular cross-section with a constricted profile 2220b incorporating a tri-leaflet valve 2230b. FIG. 22C depicts a frame having a D-shaped cross-section with a cylindrical profile 2220c incorporating a bi-leaflet valve 2230a.

It may be appreciated that alternative frames and leaflet systems may be contemplated in addition to the examples depicted herein. Thus, a frame may include a cylindrical profile, a constricted profile, a bulging profile, or any other profile appropriate for stabilizing one or more valve leaflets as required for the function of the replacement valve. A frame may also have a D-shaped cross section, a circular cross section, an oval cross section, or a cross section having any closed geometrical shape appropriate for stabilizing one or more valve leaflets as required for the function of the replacement valve. The valve frames may also secure one, two, three, four, or another number of valve leaflets as required for the function of the replacement valve.

Regardless of the shape of the implantable valve frame, the valve frame may be configured to be delivered by means of a catheter. Catheters disclosed above with respect to the implanting of an annuloplasty ring (or adjustable stabilizing ring) may also be used to deliver the implantable valve frames. In some examples, a catheter may be used to deploy a stabilizing ring and a valve frame. Alternative examples may include a catheter for deploying a valve frame that is different from the catheter used to deploy a stabilizing ring. It may be understood that the deployed implantable valve frame may be physically larger than a lumen of a catheter used for its deployment. Thus, the implantable valve frame may be delivered by the catheter at the locus of the natural valve in an at least partially collapsed state. Upon deployment, the implantable valve frame may be expanded to a functional (expanded) state. In some embodiments, the implantable valve may expand from its at least partially collapsed state to its expanded state under the actions of an expansion device. In one example, the expansion device may be a balloon placed adjacent to the at least partially collapsed valve frame. Such an expansion device may expand the valve frame as the balloon is inflated. In other embodiments, the implantable valve frame may be self-expanding. Such self-expanding implantable valve frames may be composed of a memory metal, such as a nickel titanium alloy.

FIGS. 23A-D depict non-limiting examples of a combination system including an implantable valve frame and an adjustable stabilizer ring. In each of FIGS. 23A-D, an adjustable stabilizing ring 2320 having extended anchors 2330 is depicted inclosing at least some portion of a valve frame (2310a,b). In some embodiments, the stabilizing ring 2320 may be in physical contact with at least a portion of an exterior surface of the valve frame (2310a,b).

Figure 23A:
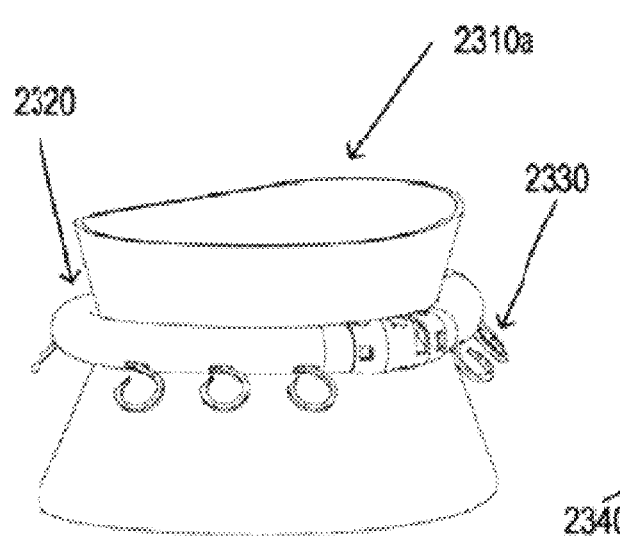
FIG. 23A depicts a perspective view of an illustrative example of an implantable valve system including an adjustable valve support ring in a closed geometry with extended anchors and an angled D-shaped cylindrical valve frame including an exemplary bi-leaflet valve according to an embodiment.
Figure 23B:
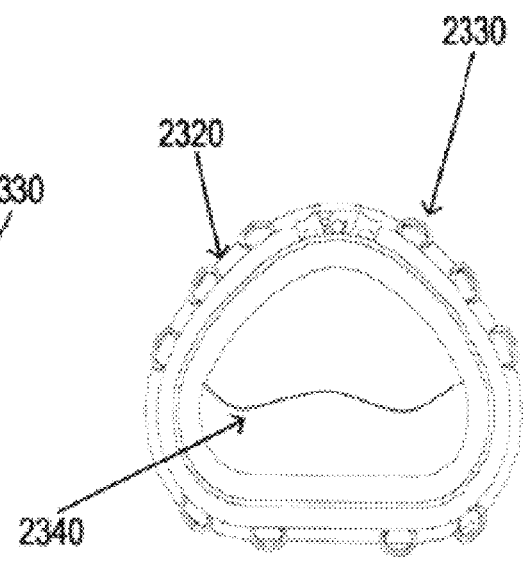
FIG. 23B depicts a top view of the implantable valve system depicted in FIG. 23A.

As depicted in FIGS. 23A and 23B, the implantable valve frame 2310a may be a D-shaped frame having a constriction with which the stabilizing ring 2320 is in contact. As depicted in FIG. 23B, such a combination system of valve frame 2310a and adjustable stabilizing ring 2320 may house a two-leaflet valve 2340. It may be noted in FIGS. 23A and 23B that the valve frame 2310a may have a geometry permitting continuous physical contact between the portion of the valve frame exterior surface and the stabilizing ring 2320.

Figure 23C:
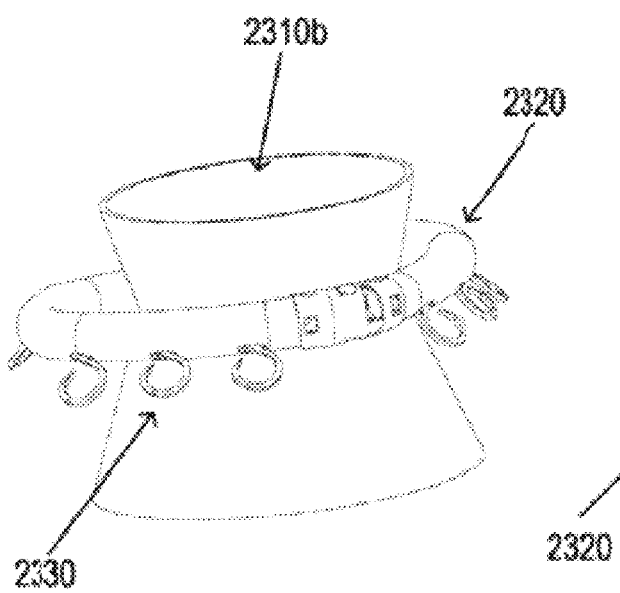
FIG. 23C depicts a perspective view of an illustrative example of an implantable valve system including an adjustable valve support ring in a closed geometry with extended anchors and an angled cylindrical valve frame including an exemplary tri-leaflet valve according to an embodiment.
Figure 23D:
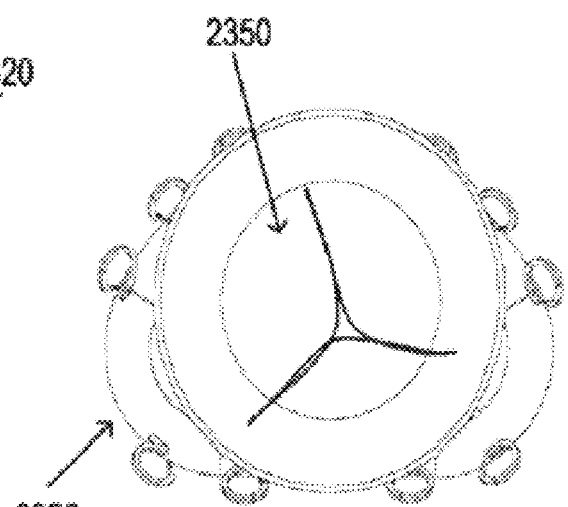
FIG. 23D depicts a top view of the implantable valve system depicted in FIG. 23C.

As depicted in FIGS. 23C and 23D, the implantable valve frame 2310b may be a cylindrical frame having a constriction with which the stabilizing ring 2320 is in contact. As depicted in FIG. 23D, such a combination system of valve frame 2310b and adjustable stabilizing ring 2320 may house a three-leaflet valve 2350. It may be noted in FIGS. 23C and 23D that the valve frame 2310b may have a geometry in which only partial physical contact is made between the portion of the valve frame exterior surface and the stabilizing ring 2320.

In addition to the configurations depicted in FIGS. 23A-D, a stabilizing ring 2320 may form a continuous physical contact with a portion of a valve frame having a D-shape cross-section, a circular cross-section, an oval cross-section, or any other continuous geometrical cross-section. Alternatively, a stabilizing ring 2320 may form only a partial physical contact with a portion of a valve frame having a D-shape cross-section, a circular cross-section, an oval cross-section, or any other continuous geometrical cross-section. Further, a stabilizing ring 2320 may form a continuous physical contact or a partial physical contact with an exterior surface of a valve frame having a constricted profile, a straight profile, or a bulging profile. It may further be understood that a stabilizing ring 2320 may form a continuous physical contact or a partial physical contact with any portion of an exterior surface of a valve frame regardless of the valve frame profile.

Figure 24:
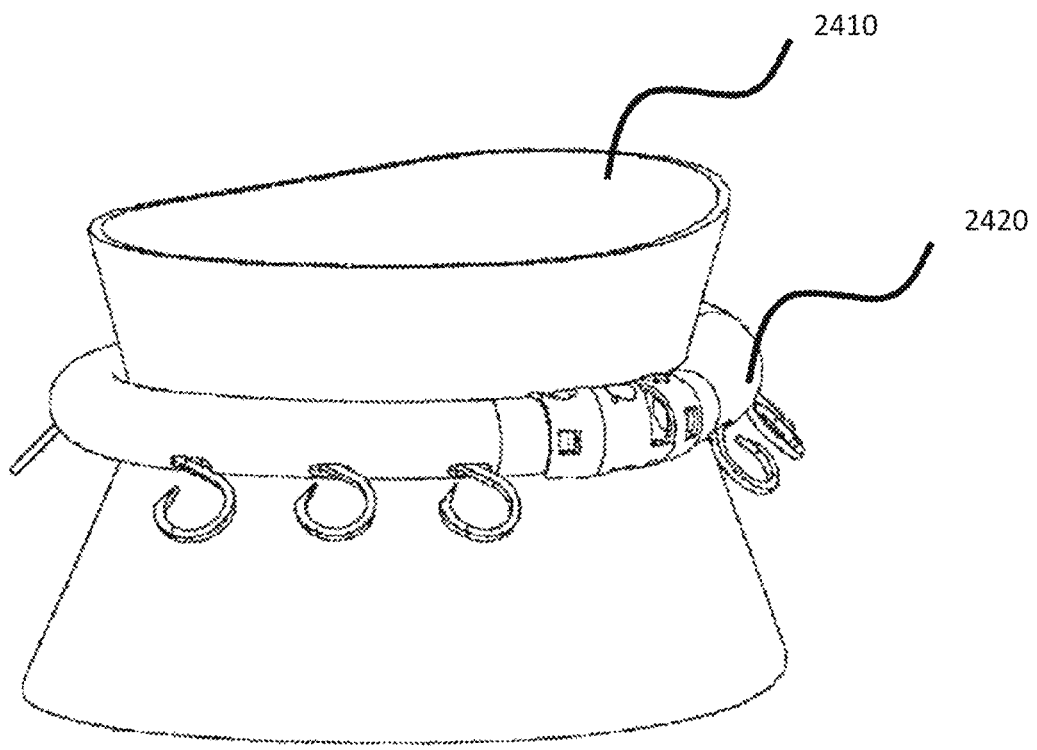
FIG. 24 depicts an isometric view of an illustrative example of a structural valve member and a support structure according to an embodiment.
Figure 25:
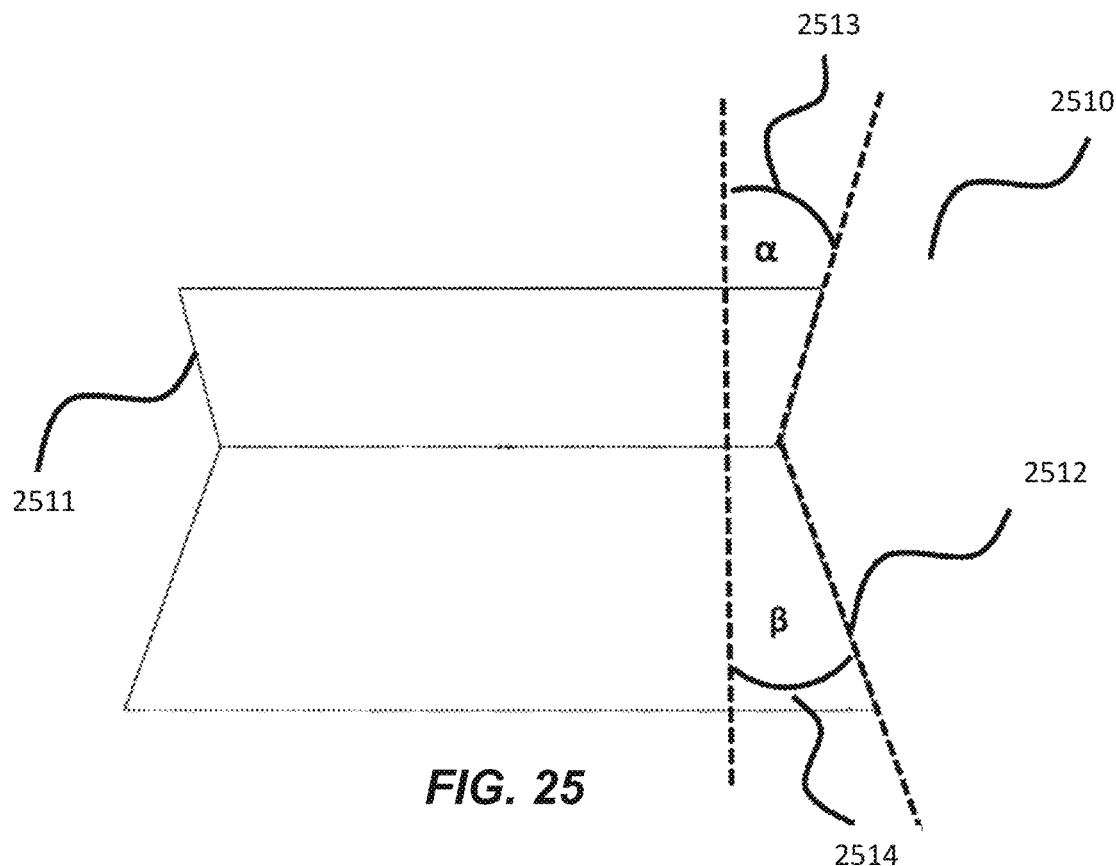
FIG. 25 depicts a front view of an illustrative example of a structural valve member according to an embodiment.

Referring now to FIG. 24, an example embodiment is shown having a support structure (e.g., a stabilizing ring) 2420 having physical contact with a bio prosthesis, or valve 2410. In some embodiments, and as shown in FIG. 25, the bio prosthesis valve 2510 may angle or tilt away from center. Thus, in some embodiments, the atrial portion of the valve 2511 may angle or tilt toward or away (e.g., in a range from −45° to +45°), represented as "α" 2513 in FIG. 25 in relation to the central axis of the valve. In a further embodiment, the ventricle portion of the valve 2512 may angle or tilt toward or away (e.g., in a range from −45° to +45°), represented as "β" 2514 in FIG. 25.

It may be understood that other combination systems of valve frames and stabilizing rings may be contemplated. Thus, an implantable valve frame may be composed of a plurality of individual segments affixed to each other to form a crisscross geometry or more complex geometry made from straight or curved links. Alternative implantable valve frames may include interlaced segments. In alternative non-limiting embodiments, a combination system may include multiple stabilizing rings. In one non-limiting example, a first stabilizing ring may be in mechanical communication with a proximal end of an implantable valve frame, and a second stabilizing ring may be in mechanical communication with a distal end of an implantable valve frame.

Figure 26A:
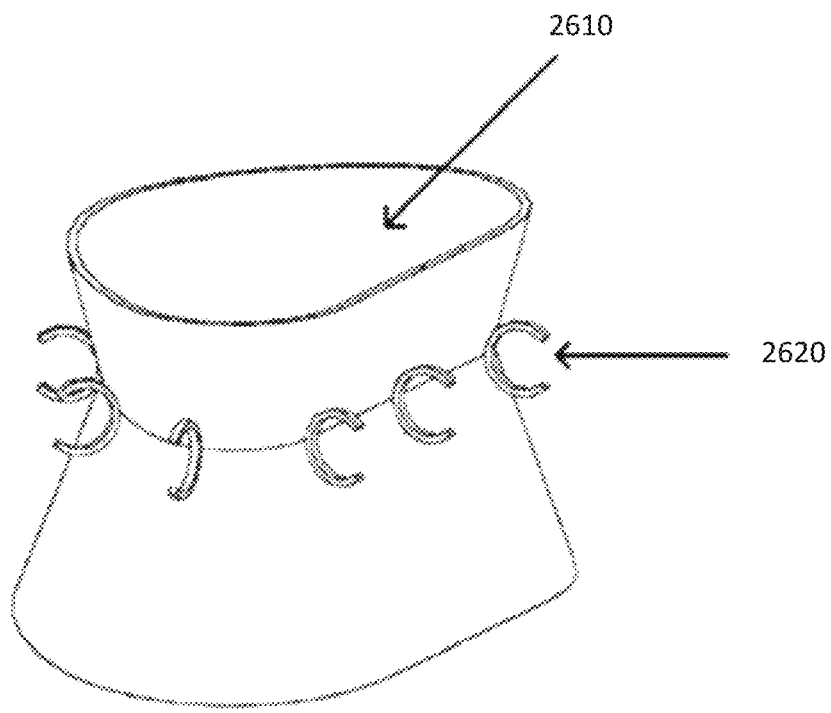
FIG. 26A depicts an isometric view of an illustrative example of an angled D-shaped cylindrical valve frame having attachment anchors for a support ring according to an embodiment.
Figure 26B:
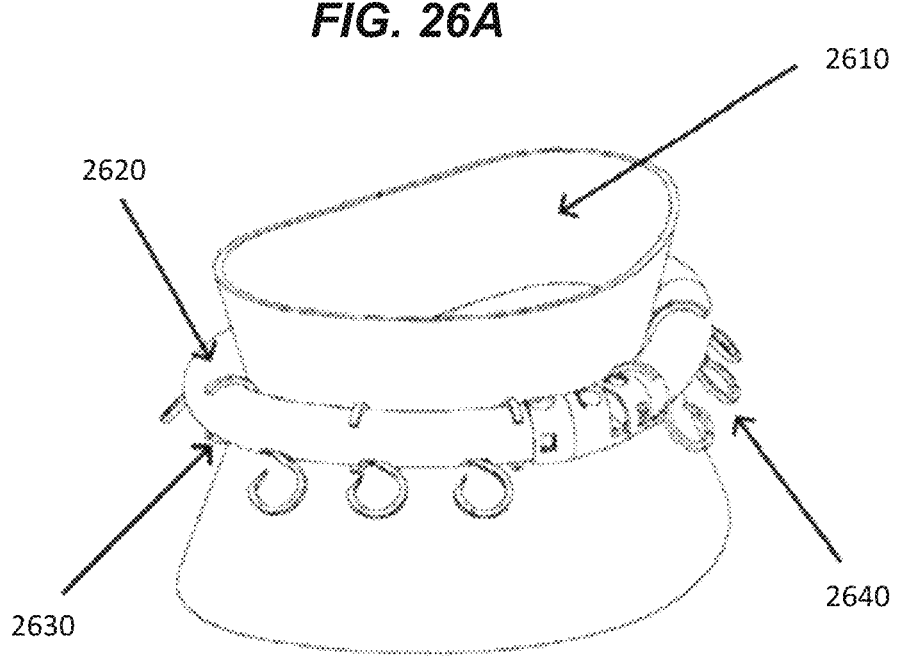
FIG. 26B depicts an isometric view of an illustrative example of an implantable valve system including an adjustable valve support ring in a closed geometry with extended anchors secured to an angled D-shaped cylindrical valve frame having attachment anchors according to an embodiment.

In other examples, the implantable valve frame may incorporate features to assist in stabilizing its physical contact with the adjustable stabilizing ring. Such a valve frame is depicted in FIGS. 26A and 26B. As depicted in FIG. 26A, the implantable valve frame 2610 may include at least one frame anchor 2620 in mechanical communication with an exterior side or bridging element of the valve frame. As depicted in FIG. 26B, the adjustable stabilizing ring 2630 may be disposed in such a manner as to contact the one or more frame anchors 2620. It should be understood that the frame anchors 2620 may be distinguished from the anchors 2640 incorporated into the stabilizing ring that may be used to anchor the stabilizing ring in the annular tissue around the natural valve.

Although FIGS. 26A and 26B depict a valve frame having a D-shaped cross-section and a constricted profile, it may be understood that any suitable valve frame may incorporate frame anchors 2620 to assist in the mechanical communication of an exterior surface of the valve frame and the adjustable stabilizing ring. Non-limiting examples of such valve frames may be characterized by a straight profile, a constricted profile, a bulging profile, a circular cross-section, a D-shaped cross-section, an oval cross-section, any continuous geometrical cross-section, one or more interleaved bridging segments, a continuous bridging segment, a plurality of bridging segments, and other shapes, sizes, constructions, and geometries.

Figure 27:
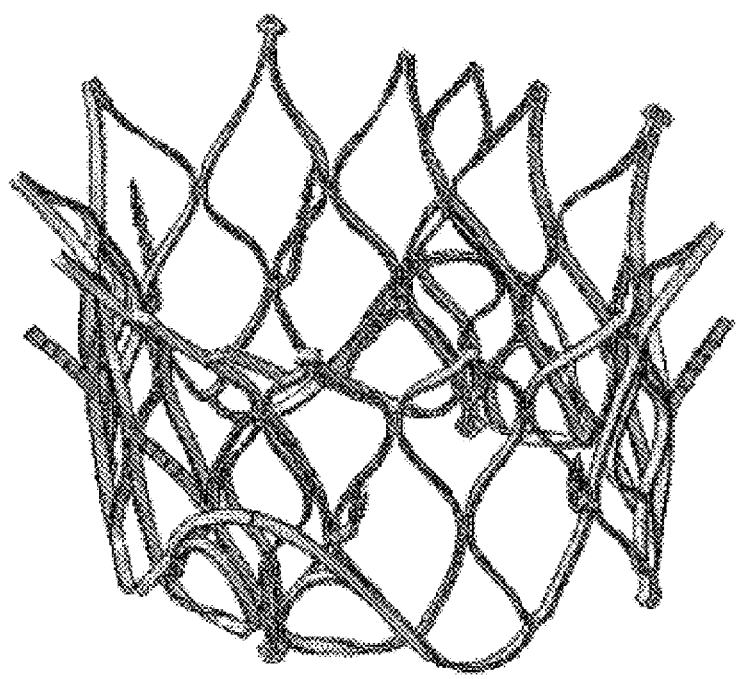
FIG. 27 depicts an isometric view of an illustrative example of a structural valve member according to an embodiment.
Figure 28:
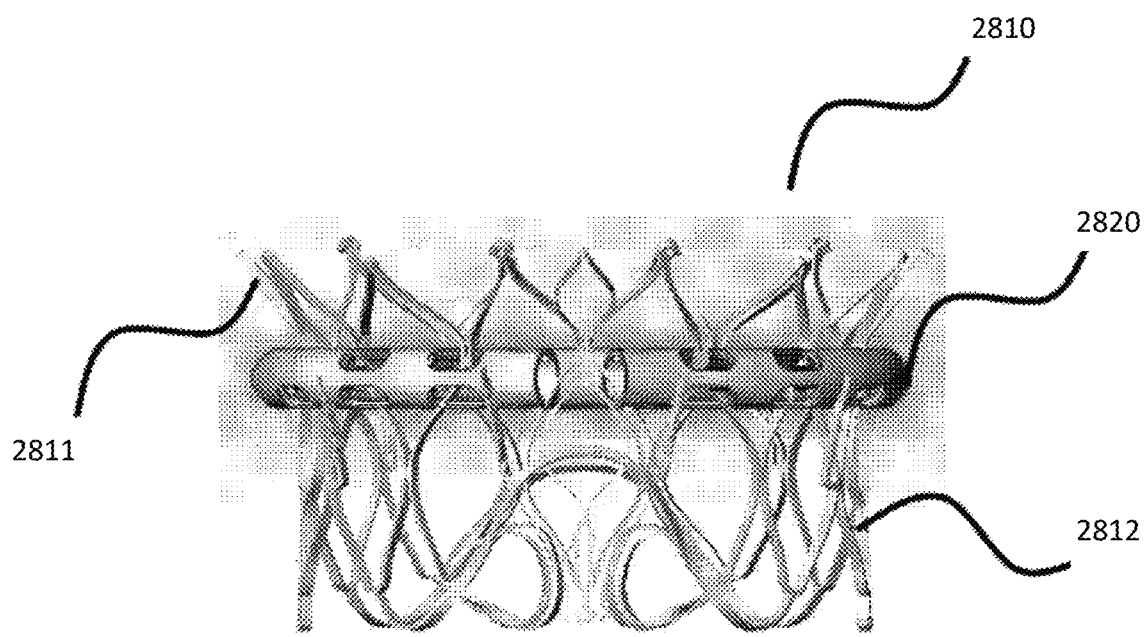
FIG. 28 depicts a front view of an illustrative example of a structural valve member and a support structure according to an embodiment.

Thus, as discussed herein, in an embodiment, a valve frame may include interleaved bridging segments, such as that shown in FIG. 27. Similar to the angle/tilt shown in FIG. 25, the mesh, or interleaved segments, of a valve may angle away or toward the central axis of the valve. Thus, as shown in FIG. 28, the atrial portion 2811 and the ventricle portion 2812 of the valve 2810 may angle away/towards the valve axis in a range from −45° to +45°. In a further embodiment, such as that shown in FIG. 29, the valve frame 2910 may have one or more locking features 2916 configured to enable the bio prosthesis (e.g., valve or valve frame) 2910 to securely attach to or connect with the support structure or ring 2920.

Additionally, in some embodiments, the valve frame 2910 may have one or more anti-SAM mechanisms 2915. As should be understood by one of ordinary skill in the art, Systolic Anterior Motion (SAM) is generally defined as displacement of the distal portion of the anterior leaflet of the mitral valve toward the left ventricular outflow tract obstruction. SAM can occur in patients without hypertrophic cardiomyopathy (HOCM) and is a well-recognized cause for unexplained sudden hypotension in perioperative settings.

Thus, in some embodiments, it may be beneficial for the valve frame to include one or more anti-SAM mechanisms 2915, as discussed herein.

Figure 30:
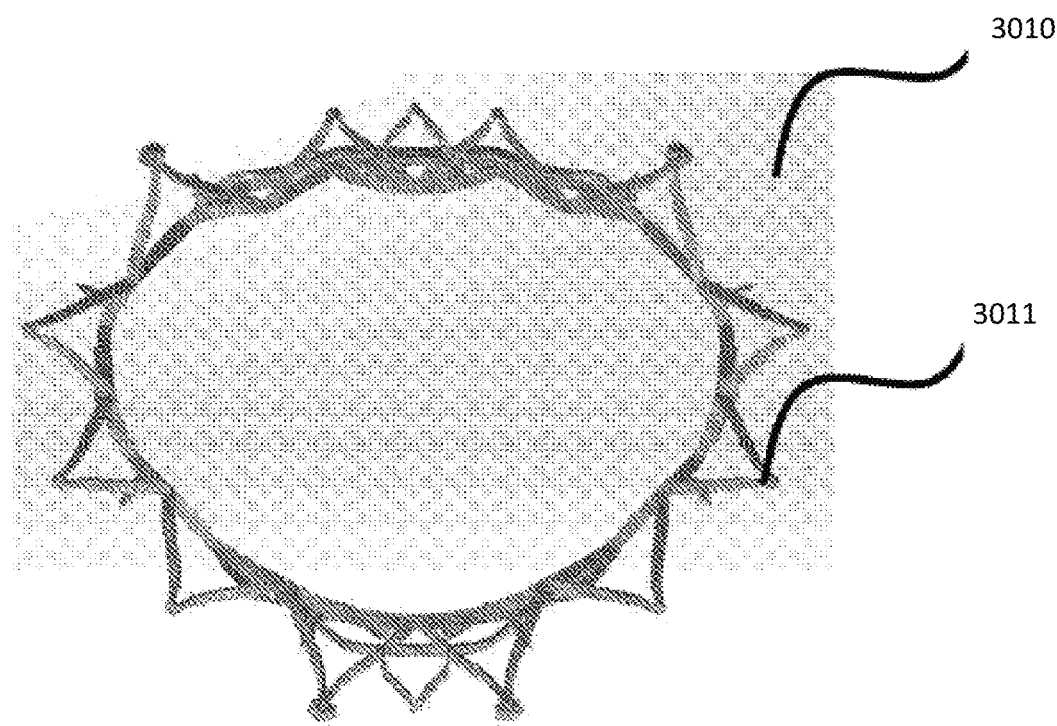
FIG. 30 depicts a top view of an illustrative example of a structural valve member according to an embodiment.

As discussed herein, various portions of the valve frame may angle or tilt away or towards the central axis of the bio prosthesis. Thus, referring now to FIG. 30, a top view of the valve frame 3010 is shown, where the atrial portion 3011 is shown extending beyond the circumference of the valve frame 3010. It should be further understood that the angle or tilt may vary around the circumference of the atrial or ventricle portion. Thus, in some embodiments, depending on the placement of the valve and the native valve characteristics, some portions of the valve may angle toward, while others angle away, and the actual degree of tilt may vary throughout.

Figure 29:
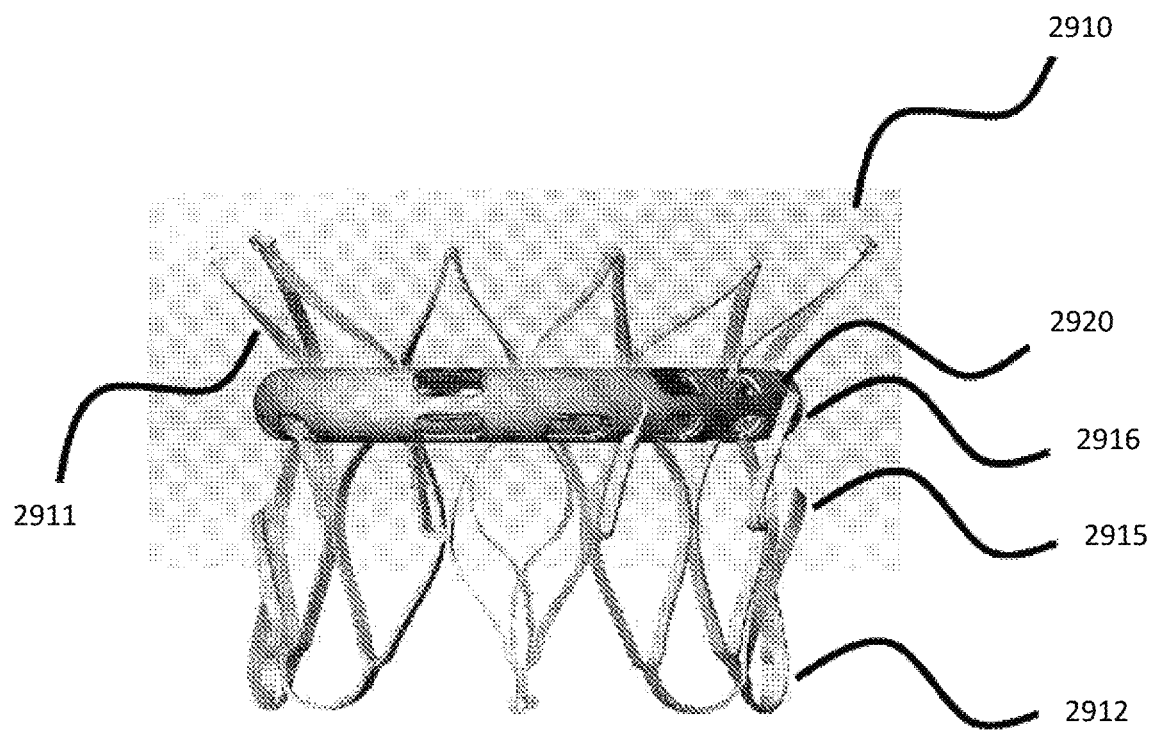
FIG. 29 depicts another front view of an illustrative example of a structural valve member and a support structure according to an embodiment.
Figure 31:
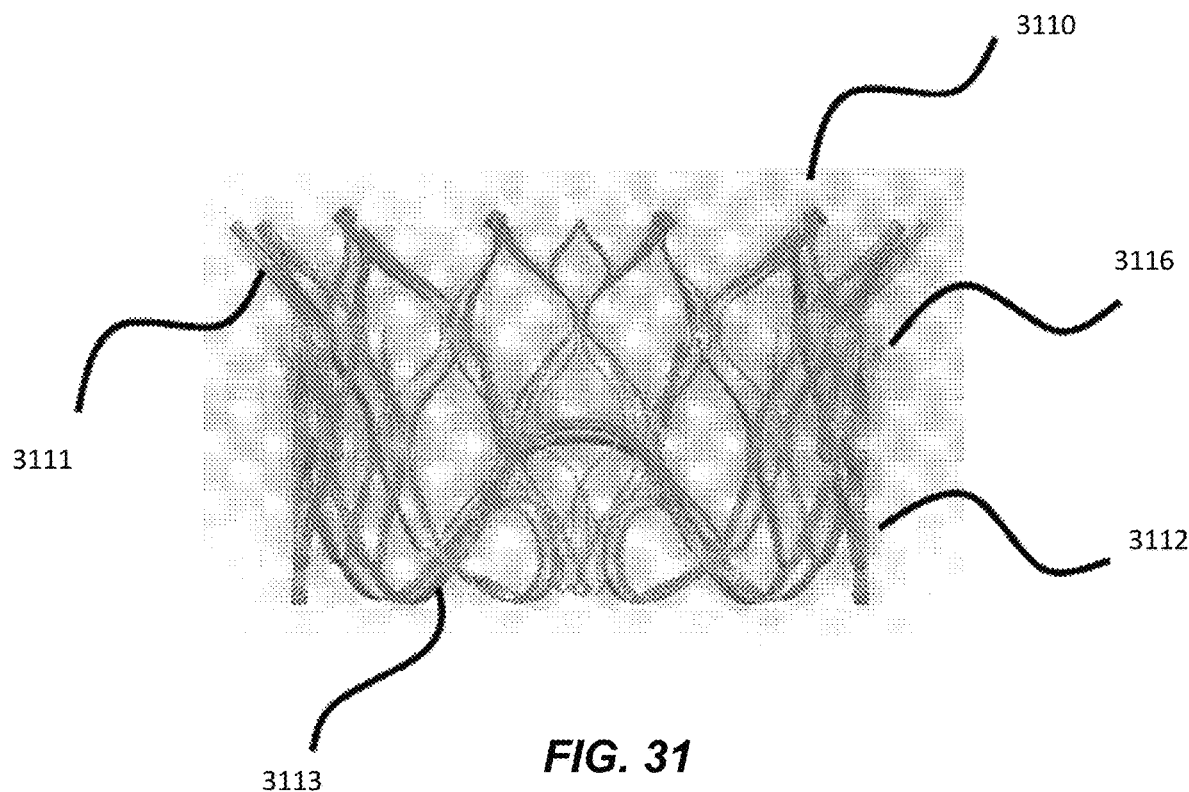
FIG. 31 depicts a front view of an illustrative example of a structural valve member according to an embodiment.
Figure 32:
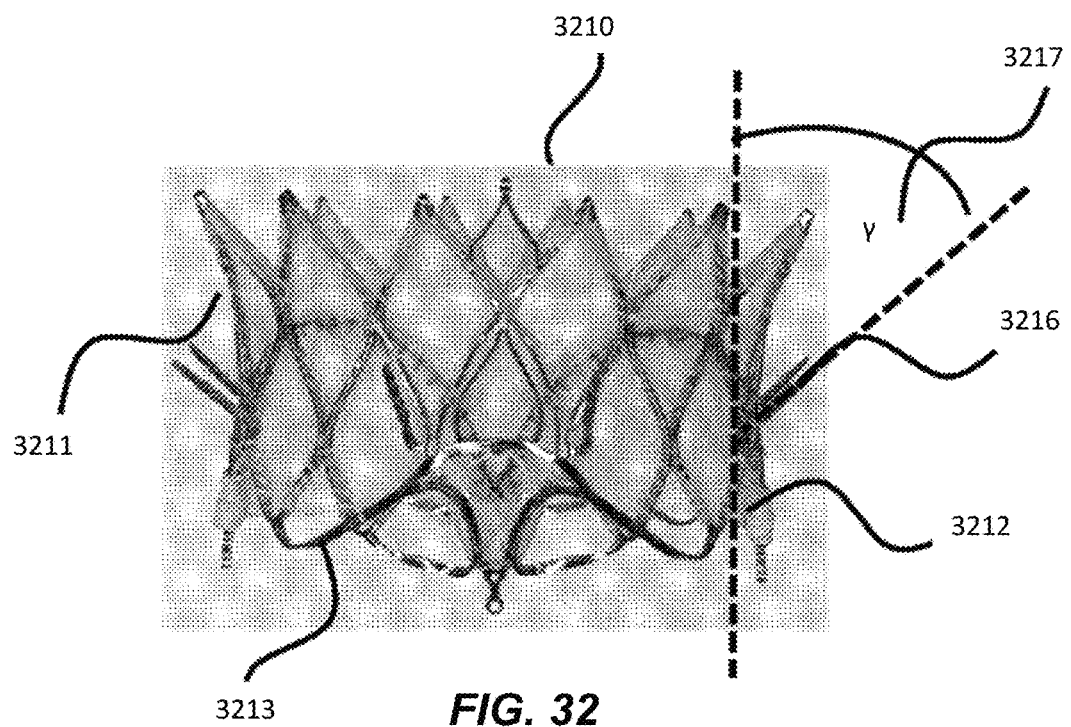
FIG. 32 depicts another front view of an illustrative example of a structural valve member according to an embodiment.

As discussed herein, and shown in FIG. 31, the valve 3110 may have an atrial portion 3111 and a ventricle portion 3112. Thus, in contrast to FIG. 29, FIG. 31 shows an embodiment without the support structure (e.g., ring), which has an anti-SAM mechanism 3113 and a ventricle locking feature 3116 (e.g., for use with the ring/support structure (not shown). Referring now to FIG. 32, a valve is shown according to an embodiment, which may have an atrial portion 3211 and a ventricle portion 3212. As discussed herein, in some embodiments, the valve 3110 may have an anti-SAM mechanism 3113 and a ventricle locking feature 3214. As shown in FIG. 32, the ventricle locking feature 3214 may, similarly to the atrial portion 3211 and a ventricle portion 3212, angle and/or tilt toward or away from the central axis of the valve (e.g., in a range from −45° to +45°), represented as "γ" 3217 in FIG. 32.

Figure 33:
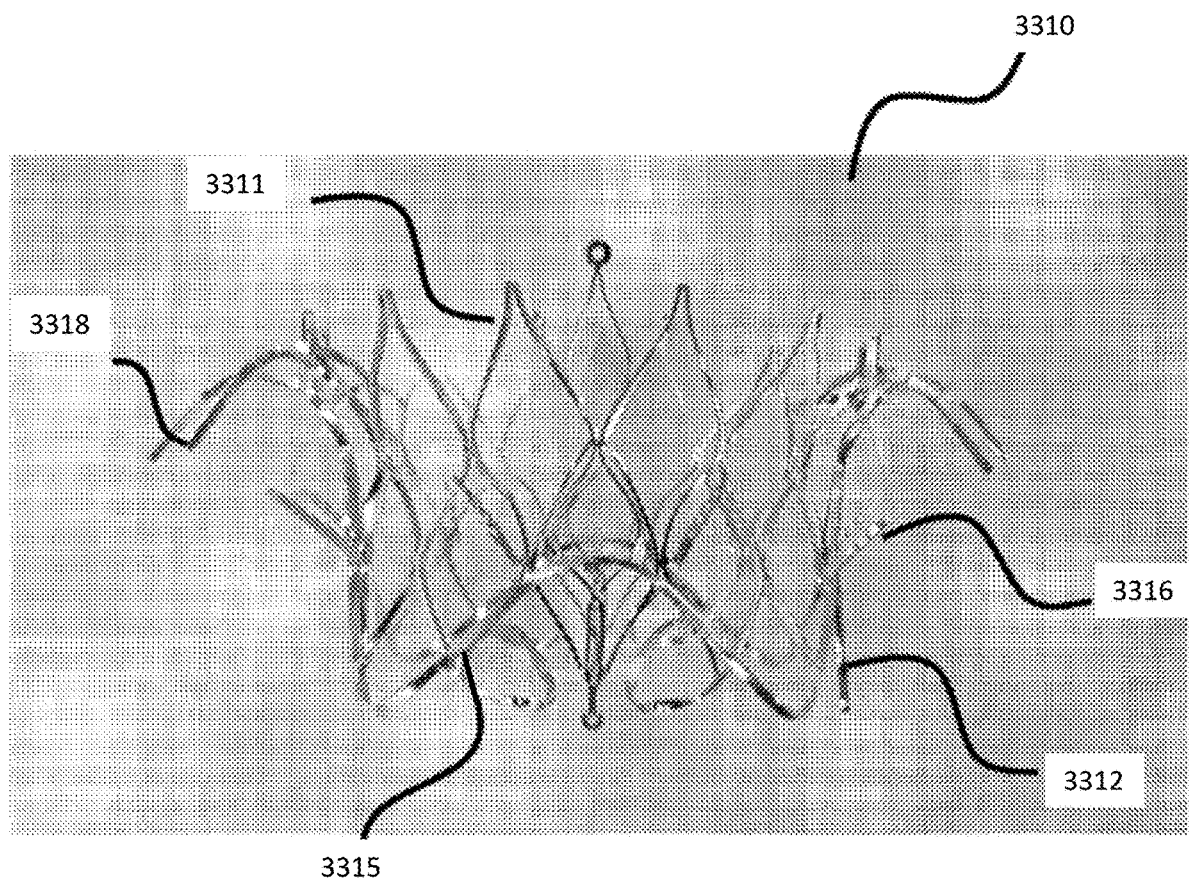
FIG. 33 depicts an isometric view of an illustrative example of a structural valve member according to an embodiment.

In a further embodiment, such as shown in FIG. 33, a valve 3310 may have an atrial locking feature 3318 in addition to the previously mentioned atrial portion 3311, ventricle portion 3312, anti-SAM mechanism 3315, and ventricle locking feature 3316. In some embodiments, and as shown in FIG. 33, the ventricle locking feature 3316 may be configured or designed to allow it to curl or curve over the top of the support structure (e.g., ring) (not shown). In a further embodiment, the ventricle locking feature 3316 may be configured or designed to allow it to create a recess or "V" within with a support member (e.g., ring) may sit or be fixed.

Thus, as discussed herein, in some embodiments, the frame 3310 may have one or more ventricle locking features 3316 and one or more atrial locking features 3318, which can be used together or individually to secure the valve 3310 to the support structure (not shown). Accordingly, in some embodiments, the valve 3310 may be secured to the support structure using one or more atrial locking features 3318 only. While in other embodiments, the valve 3310 may be secured to the support structure using one or more ventricle locking features 3316 only. In yet other embodiments, the valve may be secured using one or more ventricle locking features 3316 and one or more atrial locking feature 3318 together or in combination.

Figure 34:
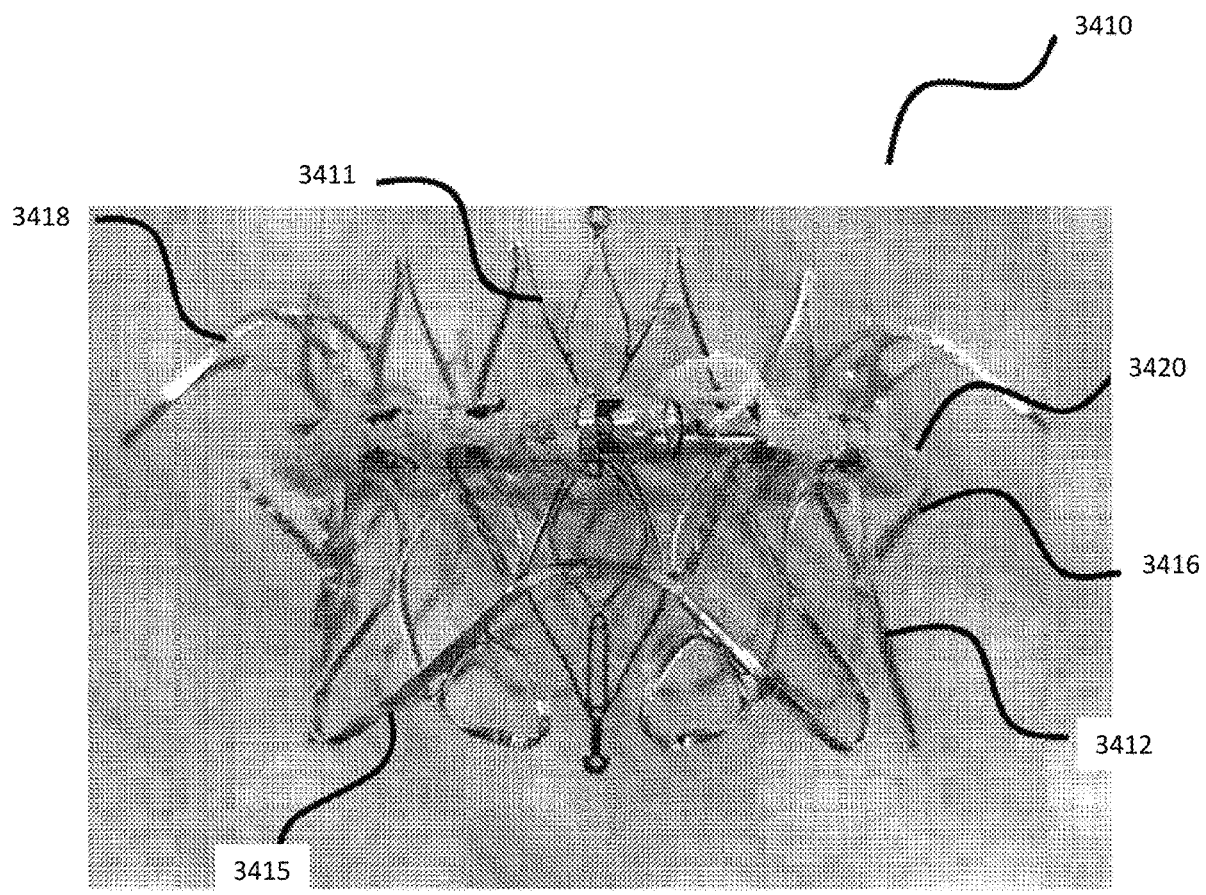
FIG. 34 depicts a front view of an illustrative example of a structural valve member and a support structure according to an embodiment.

Referring now to FIG. 34, an embodiment is shown in which the support member (e.g., ring) 3420 is present and is located between the one or more ventricle locking features 3316 and one or more atrial locking features 3318. Additionally, similar to the above referenced figures, FIG. 34 depicts an embodiment having a valve 3410, an atrial portion 3311, a ventricle portion 3312, an anti-SAM mechanism 3315, and the support structure 3420. In some embodiments, and as shown in FIGS. 33 and 34, the ventricle locking feature 3416 may be configured or designed to allow it to curl or curve over the top of the support structure (e.g., ring) (not shown). In a further embodiment, the ventricle locking feature 3416 may be configured or designed to allow it to create a recess or "V" within with a support member (e.g., ring) may sit or be fixed.

In a further embodiment, one or more anti-SAM mechanisms 3415, one or more ventricle locking features 3416, and one or more atrial locking features 3418 may be used to assist in various actions. For example, in some embodiments, the positioning of the valve 3410 in relation to the support ring 3420 may be altered or modified via activation or manipulation of the one or more anti-SAM mechanisms 3415, the one or more ventricle locking features 3416, and the one or more atrial locking features 3418.

In another embodiment, the one or more anti-SAM mechanisms 3415, one or more ventricle locking features 3416, and one or more atrial locking features 3418 may also assist in locking the valve 3410 to the support ring 3420, as well as ensuring the distance between the valve and native tissue remains small to improve sealing, as discussed herein. In yet another embodiment, the one or more anti-SAM mechanisms 3415, one or more ventricle locking features 3416, and one or more atrial locking features 3418 may also assist in reducing the load of the valves/leaflets 3410 on the support ring 3420. Additionally, in some embodiments, the one or more anti-SAM mechanisms 3415, one or more ventricle locking features 3416, and one or more atrial locking features 3418 may prevent free motion of one or more native leaflets, which could create hemodynamic problems though the left ventricular outflow tract and/or the bio prosthesis (e.g., valve 3410).

As shown and discussed herein, specifically with reference to FIGS. 25 and 28-34, the atrial portion and ventricle portion may, if needed, angle away, or bend outwards to distance the structural member (e.g., valve, valve frame) from the leaflets (e.g., native or artificial (bio prosthesis)). In a further embodiment, a seal may be created between the support structure 3420, the structural member 3410, and/or the leaflets (not shown). It should be understood, that the seal may be a complete seal or only seal a portion of the area. The bio prosthesis leaflets, as discussed herein, may be of varying shape and number (e.g., 1, 2, 3, or 4 leaflets). In some embodiments, the seal may be achieved using a polymeric material, such as, for example, PET (e.g., Dacron, polyester, etc.). In a further embodiment, the seal may be configured to both seal and encourage tissue ingrowth and encapsulation of the structural member (e.g., valve or valve frame).

Various types and styles of leaflets are disclosed in International Application Number PCT/US2020/37294, which is assigned to Valcare Inc. and is entitled "ANNULOPLASTY RING WITH POSTERIOR LEAFLET FOR MINIMALLY INVASIVE TREATMENT," the subject matter of which is incorporated herein by reference.

Figure 35:
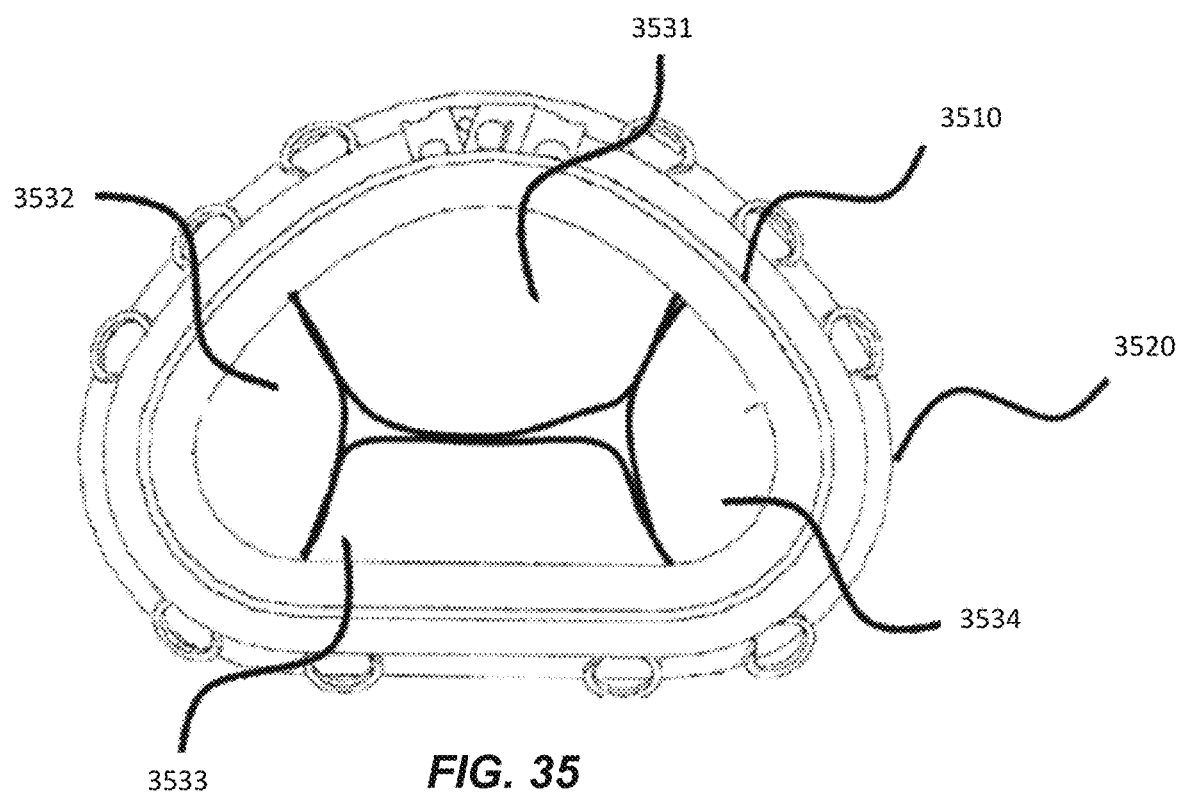
FIG. 35 depicts a top view of an illustrative example of a structural valve member having leaflets and a support structure according to an embodiment.
Figure 36:
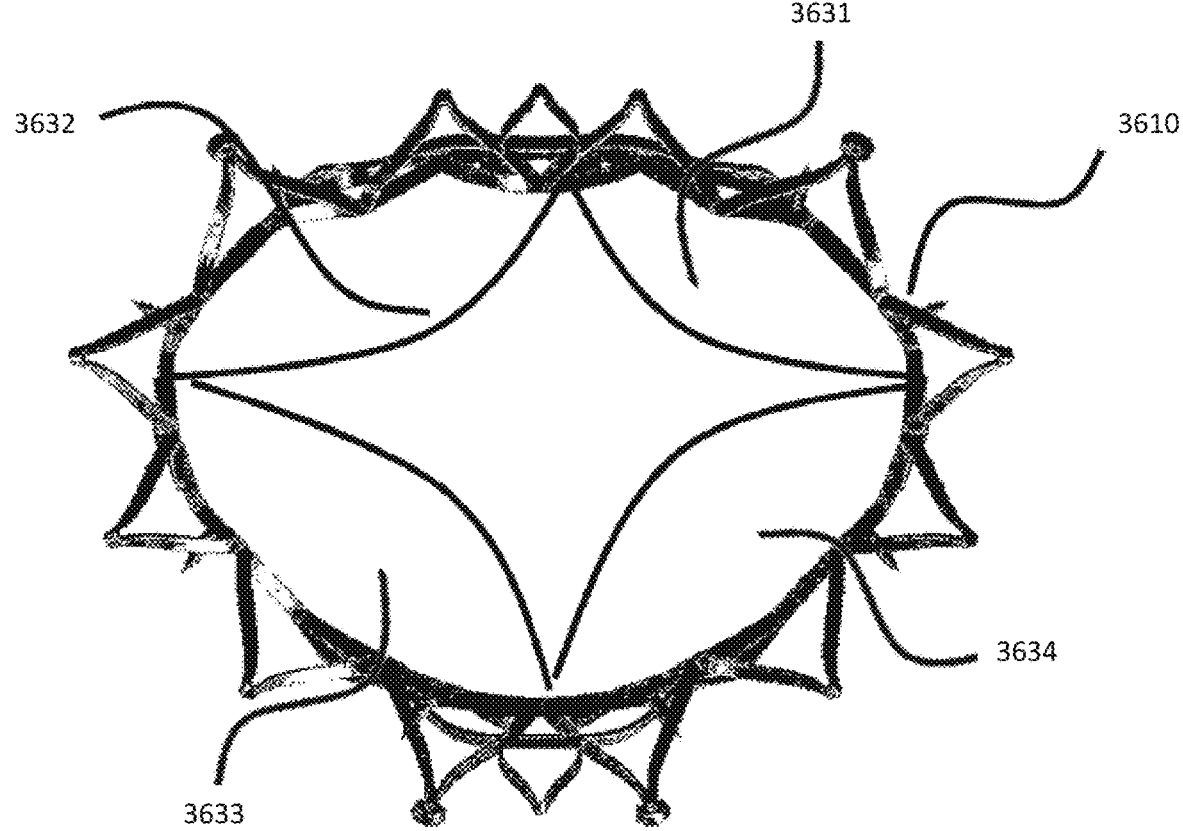
FIG. 36 depicts a top view of an illustrative example of a structural valve member having leaflets according to an embodiment.

Referring now to FIGS. 35 and 36, a top view of a support structure 3520 and a structural member 3510 are shown according to various embodiments. As shown, and discussed herein, the structural member 3510 may comprise various numbers of leaflets (e.g., 1, 2, 3, 4, etc.). Moreover, in some embodiments, the arrangement or "pattern" of the leaflets may vary. The leaflet arrangement may vary for multiple reasons, such as, for example, patient physiology, support member or ring shape, native valve being replicated, etc. This is clearly shown when comparing FIGS. 35 and 36.

In FIG. 35, leaflet 3531 is located almost entirely in the curve of the D-shaped ring 3510, whereas leaflets 3532 and 3534 are located in the opposing curves of the ring as shown. Finally, leaflet 3533 is located along the primarily flat/ straight portion of the support member 3520. Thus, in some embodiments, and as shown in FIG. 35, the leaflets may be sized very differently (e.g., leaflet 3531 being much larger than the remaining leaflets). In an alternative embodiment, the leaflets may be arranged as shown in FIG. 36, such that all four leaflets 3631, 3632, 3633, and 3634 are primarily located in a corner, such that each leaflet is roughly the same size and shape.

Figure 37:
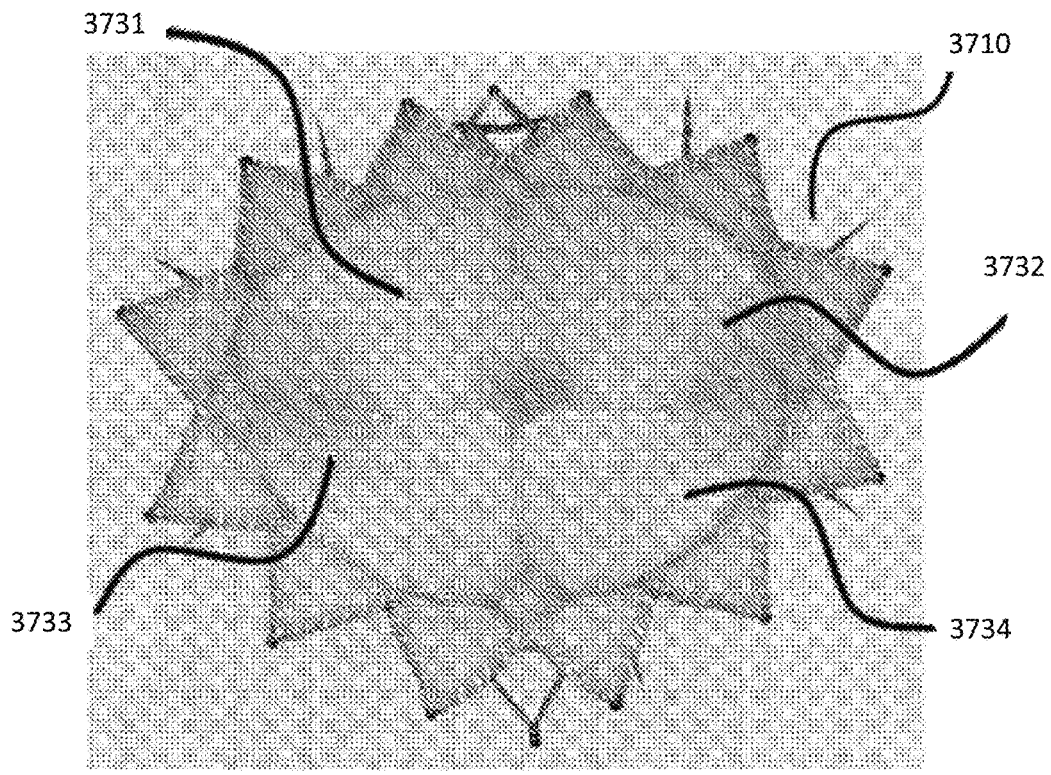
FIG. 37 depicts a top view of an illustrative example of a structural valve member having leaflets according to an embodiment.
Figure 38:
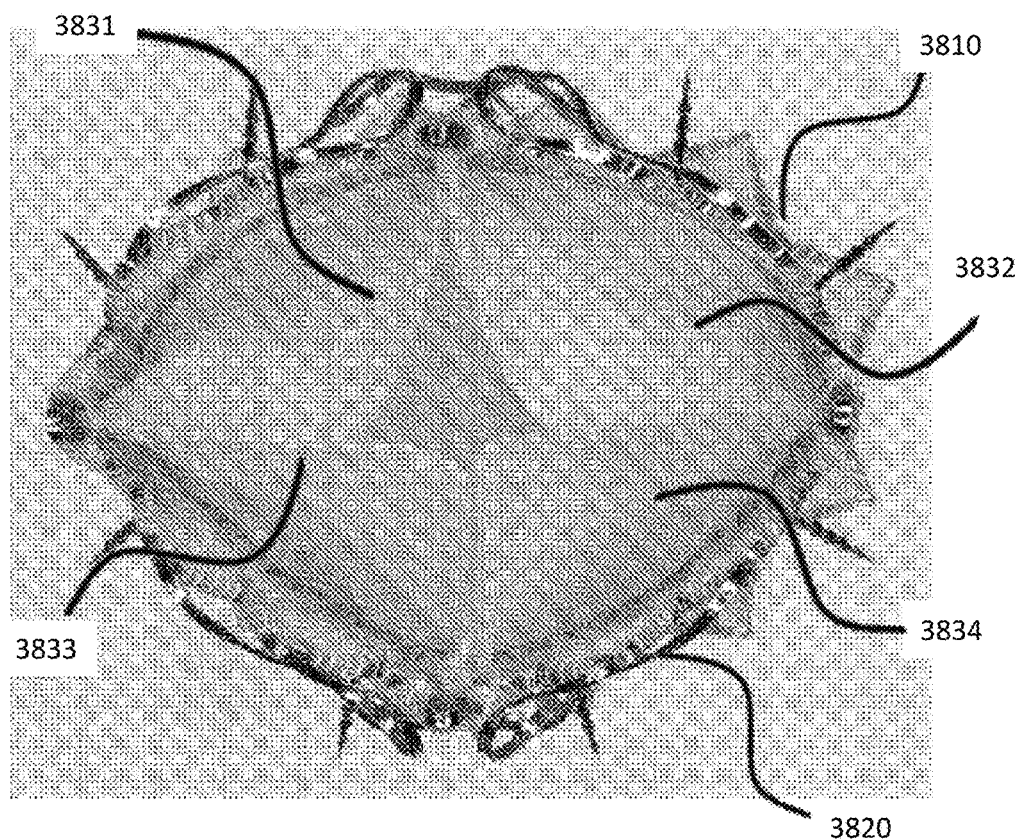
FIG. 38 depicts a top view of an illustrative example of a structural valve member having leaflets and a support structure according to an embodiment.

In some embodiments, lateral commissure leaflets and medial commissure leaflets may be identical, but not obligatory, such as shown in FIG. 35. In a further embodiment, each leaflet may be in a two-dimensional (2D) scallop shape, to allow for optimized force distribution from teach leaflet to the valve. In a further embodiment, a commissure (e.g., the attachment of the leaflets to the valve) may be moved, tilted, or bent inwards to increase the distance between the leaflets and the structural member (e.g., valve), which can increase the durability of the leaflets. FIGS. 37 and 38 show top views of additional embodiments, specifically, FIG. 37 illustrates a top view of a valve 3710 without a support ring, having four leaflets 3731, 3732, 3733, and 3734. Alternatively, FIG. 38 illustrates a top view of a valve 3310 with a support ring in place, having four leaflets 3831, 3832, 3833, and 3834. It should be understood that FIGS. 35-38 are non-limiting illustrative examples, and that various other leaflet arrangements and/or patterns can be used, such as, four identical leaflets, two pairs of leaflets of similar size and/or shape, and those found in the aforementioned International Application Number PCT/US2020/37294.

In some embodiments, the leaflets of the bio prosthesis valve may be derived or created from a biological source (e.g., pericardium). In a further embodiment, the leaflets may be constructed from synthetic material (e.g., polymeric material, such as a thermoplastic polyurethane (TPU). In an additional embodiment, wherein the leaflets are constructed from a polymeric material, the polymeric material may be composite with other materials, such as, for example, chopped fibers, nanotubes, or any other additives known or future that allow for or improve the resistance of the material to the forces and strains applied to a leaflet during the intended use of a bio prosthesis valve. Thus, in some embodiments, the leaflet and/or valve may be derived from or constructed of materials that protect against shear forces and assist in preventing development of a potential failure (e.g., crack, leak, weak point, etc.).

In a further embodiment, the polymeric material may undergo post process after the casting and/or forming of the material/film. For example, in some embodiments, curing the material may change its material properties, either by improving the mechanical properties of the material and/or altering the geometrical properties such as surface finish or other manipulation that will assist in preventing development of a potential failure (e.g., crack, leak, weak point, etc.).

Figure 39:
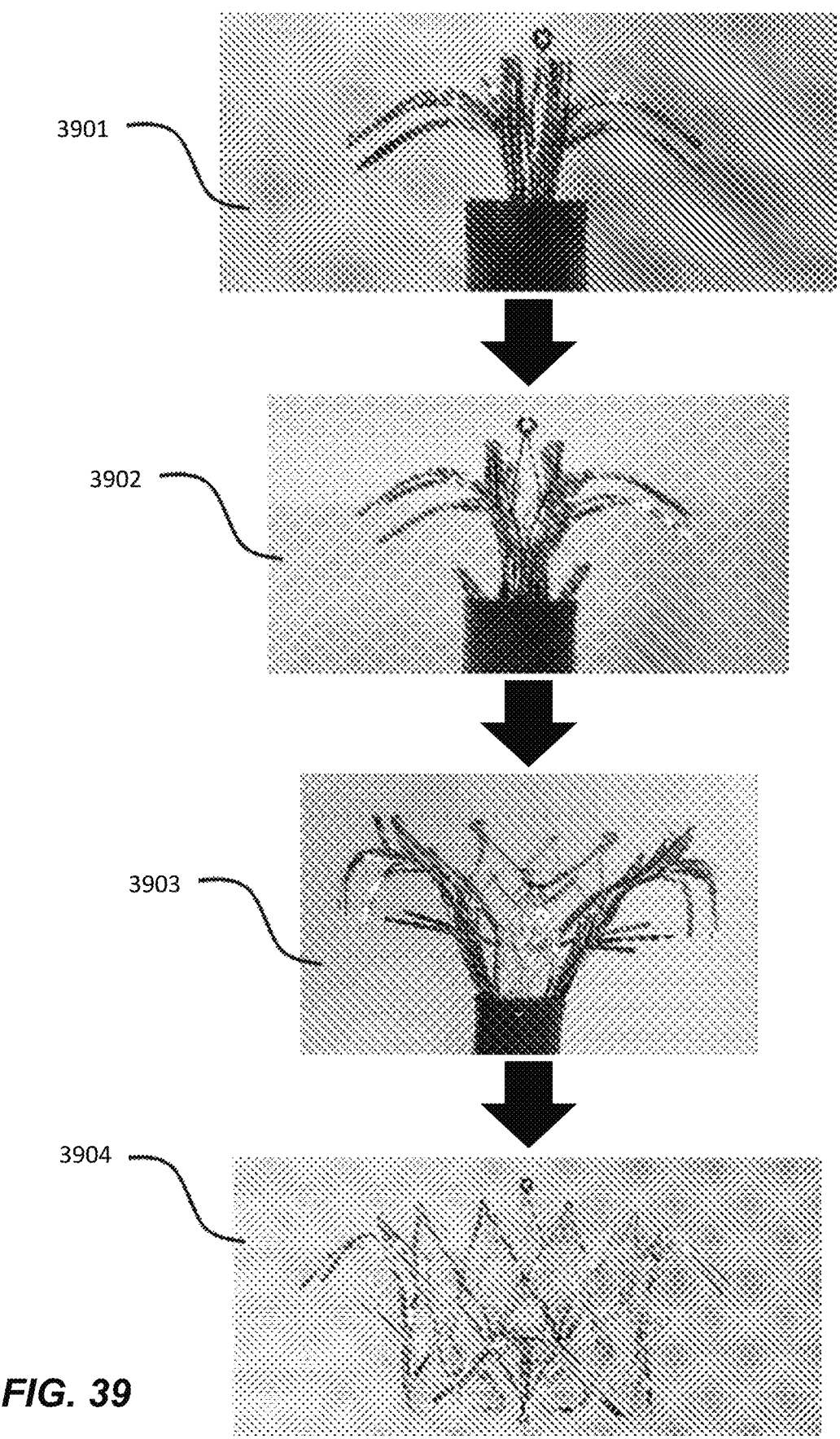
FIG. 39 depicts a flow diagram of an illustrative method of a release sequence of a structural valve according to an embodiment.

Referring now to FIGS. 34 and 39, FIG. 39 shows an illustrative example of the deployment of a valve 3410 in accordance with an embodiment. Thus, in some embodiments, and as shown at 3901, the first portion of the valve 3410 to emerge from the delivery system (e.g., a catheter) are the one or more atrial locking features 3418. Continuing to 3902, the one or more ventricle locking features 3416 follow the one or more atrial locking features 3418 out of the delivery system. As the valve 3410 continues to be released, the locking features (i.e., the one or more ventricle locking features 3416 and the one or more atrial locking features 3418) enter a pre-release position, as shown at 3903. Finally, at 3904, the valve 3410 is shown at its final configuration.

Figure 40:
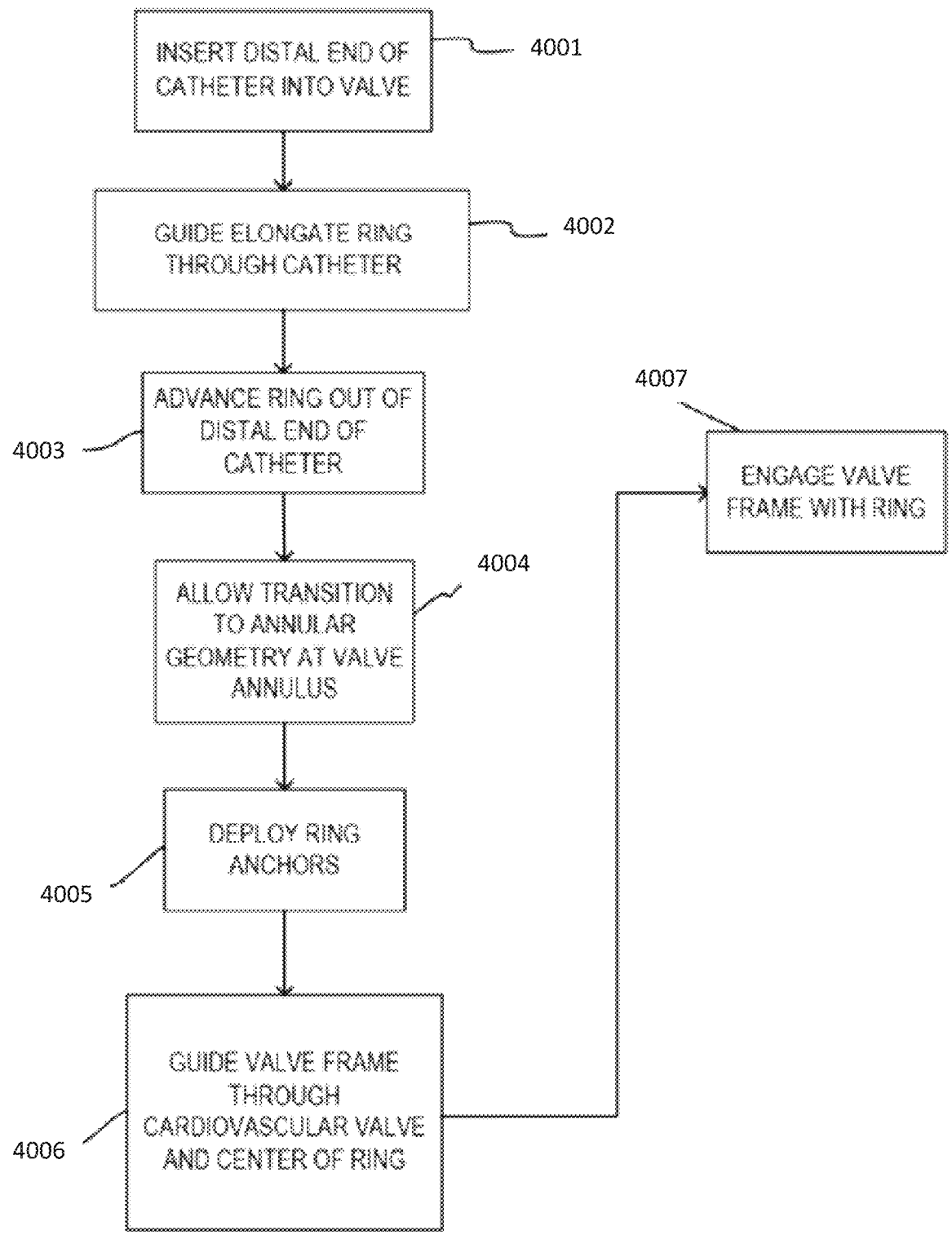
FIG. 40 depicts a flow diagram of an illustrative method of stabilizing a replacement cardiovascular valve according to an embodiment.

FIG. 40 is a flow chart of an exemplary method of stabilizing a replacement of a cardiovascular valve. The distal end of a catheter containing at least the stabilizing ring in an elongate geometry and a delivery system thereof may be inserted 4001 into a damaged or otherwise non-functioning natural valve. The delivery system may be used to guide 4002 the ring in the elongate geometry from a proximal end of the catheter to the distal end of the catheter 4003. The adjustable stabilizing ring may transition 4004 to an annular operable geometry upon exiting the distal end of the catheter proximate to the valve annulus. Once the stabilizing ring is in its operable geometry, the anchors of the ring may be deployed 4005.

It may be understood that the deployment of the stabilizing ring, including the anchors, may be sufficient to treat a malformed cardiovascular valve in the manner of an annuloplasty as disclosed above. Over time, a health care professional may determine that replacement of the natural valve may be required. Subsequent procedures may then be used to provide a replacement valve at the site of the previous annuloplasty. A catheter may be used to guide 4006 the implantable valve frame through the natural cardiovascular valve and through the center of the pre-implanted adjustable stabilizing ring. The valve frame may be engaged 4007 with the stabilizing ring, thereby stabilizing the position of the implantable valve frame with respect to the natural cardiovascular valve. In some embodiments of the method shown in FIG. 40, the stabilizing ring and the valve frame may be introduced into the cardiovascular system during the same surgical procedure. In alternative embodiments, some period of time may lapse between the placement of the stabilizing ring and the placement of the valve frame. For example, the stabilizing ring may be implanted initially to stabilize a natural cardiovascular valve, but a replacement valve may be introduced if the patient shows signs that the stabilizing ring alone is insufficient to treat the valve pathology. Alternatively, the stabilizing ring may be introduced initially and the patient's vascular system may be permitted a period of time to incorporate the stabilizing ring into the tissue before the replacement valve is introduced. In this manner, the patient's vascular tissue may grow into or around the stabilizing ring to anchor or form a seal around the ring before the replacement valve is implanted.

In some embodiments, the implantable valve frame may be engaged with the stabilizing ring by allowing or causing the implantable valve frame to expand to a functional size, thereby forming a mechanical contact between the implantable valve frame and the adjustable stabilizing ring. In some non-limiting examples, the valve frame may be allowed to self-expand. Such self-expanding valve frames may be composed of a memory material that may expand to a pre-set shape. In some alternative non-limiting examples, the valve frame may expand under the influence of an expansion device. Such an expansion device may be incorporated in the same catheter as that which delivers and emplaces the implantable valve frame. In other examples, the expansion device may be deployed from a catheter that differs from the one used to emplace the valve frame. In one non-limiting example, the expansion device may be a balloon-type device or a balloon.

Figure 41:
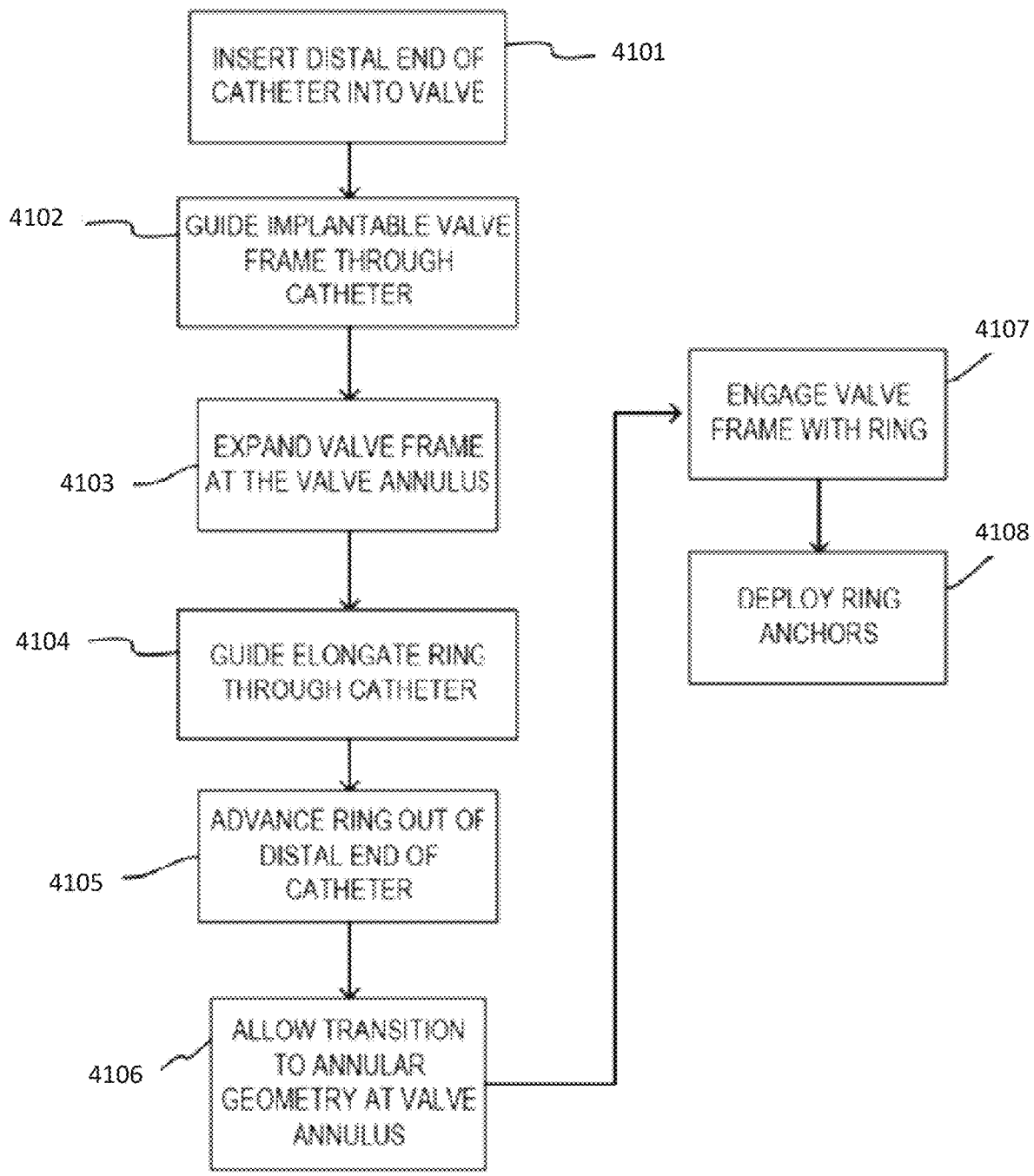
FIG. 41 depicts a flow diagram of an illustrative method of replacing a cardiovascular valve according to an embodiment.

FIG. 41 is a flow chart of an exemplary method of replacing a cardiovascular valve. The distal end of a catheter containing at least an implantable valve frame having the replacement of the cardiovascular valve and a delivery system thereof may be inserted 4101 into a damaged or otherwise non-functioning natural valve. The delivery system may be used to guide 4102 the valve frame through the catheter and through the cardiovascular valve. The valve frame may be expanded 4103, thereby deploying the replacement cardiovascular valve.

A delivery system may be used to guide 4104 a stabilizing ring in an elongate geometry through a catheter. It may be understood that the same catheter may be used to deploy and guide the stabilizing ring and the implantable valve frame. Alternatively, separate catheters may be used to deliver the implantable valve frame and the stabilizing ring. The distal end of the catheter may be positioned through the implantable valve frame and the replacement of the cardiovascular valve. In this manner, the stabilizing ring, in the elongate geometry may be advanced 4105 out of the catheter at a position distal to the replacement of the cardiovascular valve. The adjustable stabilizing ring may be allowed 4106 to transition to an annular operable geometry around an exterior surface of the implantable valve frame upon exiting the distal end of the catheter proximate to the valve annulus. The stabilizing ring in the annular operable geometry may be engaged 4107 to the valve frame. Once the stabilizing ring is in its operable geometry, the anchors of the ring may be deployed 4108.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera As a non-limiting example, each range discussed herein can be readily broken down into a lower third, middle third and upper third, et cetera As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. An implantable valve system comprising:
   an adjustable stabilizing ring comprising:
      a body member that is transitionable from an elongate insertion geometry to an annular operable geometry, and
      a plurality of anchors deployable in the annular operable geometry to engage the annulus of the cardiovascular valve; and
   an implantable valve frame comprising an atrial portion and a ventricle portion, the implantable valve frame is disposed within the body member and is in mechanical communication with an inner surface of the body member,
   wherein the elongate insertion geometry is configured to allow percutaneous passage of the stabilizing ring, via a catheter, to a position adjacent to an annulus of a cardiovascular valve,
   wherein the annular operable geometry has a closed state to conform to the annulus of the cardiovascular valve,
   wherein the implantable valve frame comprises a plurality of locking features that project from the ventricle portion of the implantable valve frame that engages with an outer circumference of the body member to secure the implantable valve frame to the body member of the adjustable stabilizing ring,
   wherein the plurality of locking features and the ventricle portion of the implantable valve frame forms a V-shape recess,
   wherein the body member of the adjustable stabilizing ring is disposed within the V-shape recess, and
   wherein the atrial portion of the implantable valve frame comprises at least one locking feature that projects from the atrial portion of the implantable valve frame and curves downward away from the adjustable stabilizing ring.

2. The implantable valve system of claim 1, wherein the implantable valve frame comprises one, two, three or four valve leaflets.

3. The implantable valve system of claim 1, wherein the adjustable stabilizing ring, the implantable valve frame, or both are coated with a pliable material.

4. The implantable valve system of claim 1, and wherein the atrial portion and the ventricle portion can be angled toward or away from a central axis of the implantable valve frame.

5. The implantable valve system of claim 1, further comprising an anti-SAM mechanism.

6. The implantable valve system of claim 1, wherein the implantable valve frame comprises a plurality of elements disposed in a crisscross arrangement.

7. The implantable valve system of claim 1, wherein the implantable valve frame is at least partially collapsible.

8. The implantable valve system of claim 7, wherein the implantable valve frame is configured to be delivered via a catheter in an at least partially collapsed state.

9. The implantable valve system of claim 7, wherein the at least partially collapsible implantable valve frame is self-expandable.

10. The implantable valve system of claim 1, wherein the adjustable stabilizing ring in the annular operable geometry is rigid or semi-rigid in the closed state.

11. A method of stabilizing a replacement of a cardiovascular valve, the method comprising:
   inserting a distal end of a catheter comprising a delivery system into a cardiovascular valve;
   guiding, via the delivery system, an adjustable stabilizing ring in an elongate geometry from a proximal end of the catheter to the distal end such that the adjustable stabilizing ring transitions to an annular operable geometry upon exiting the distal end of the catheter;
   deploying a plurality of anchors from the adjustable stabilizing ring to engage an annulus of the cardiovascular valve;
   guiding an implantable valve frame comprising the replacement of the cardiovascular valve through the cardiovascular valve and through a center of the adjustable stabilizing ring, wherein the implantable valve frame comprises an atrial portion and a ventricle portion; and
   engaging at least a portion of the implantable valve frame with the adjustable stabilizing ring, thereby stabilizing a position of the implantable valve frame with respect to the cardiovascular valve,
   wherein engaging at least the portion of the implantable valve frame with the adjustable stabilizing ring comprises expanding the implantable valve frame thereby forming a mechanical contact between the implantable valve frame and an inner surface of the adjustable stabilizing ring and extending a plurality of locking features that project from the ventricle portion of the implantable valve frame and engage with an outer circumference of the adjustable stabilizing ring to secure the implantable valve frame to the adjustable stabilizing ring,
   wherein the plurality of locking features and the ventricle portion of the implantable valve frame form a V-shape recess,
   wherein the body member of the adjustable stabilizing ring is disposed within the V-shape recess, and
   wherein the atrial portion of the implantable valve frame comprises at least one locking feature that projects from the atrial portion of the implantable valve frame and curves downward away from the adjustable stabilizing ring.

* * * * *